United States Patent
Narva et al.

(10) Patent No.: US 10,501,755 B2
(45) Date of Patent: Dec. 10, 2019

(54) FSH NUCLEIC ACID MOLECULES TO CONTROL INSECT PESTS

(71) Applicants: Dow AgroSciences LLC, Indianapolis, IN (US); Fraunhofer-Gesellschaft zur Förderung der angewandten Forschung e.V., München (DE)

(72) Inventors: Kenneth E. Narva, Zionsville, IN (US); Sarah Worden, Indianapolis, IN (US); Meghan Frey, Greenwood, IN (US); Murugesan Rangasamy, Zionsville, IN (US); Premchand Gandra, Indianapolis, IN (US); Wendy Lo, Indianapolis, IN (US); Elane Fishilevich, Indianapolis, IN (US); Rainer Fischer, Munich (DE); Andreas Vilcinskas, Giessen (DE); Eileen Knorr, Gießen (DE)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 15/478,957

(22) Filed: Apr. 4, 2017

(65) Prior Publication Data
US 2017/0283827 A1 Oct. 5, 2017

Related U.S. Application Data

(60) Provisional application No. 62/318,621, filed on Apr. 5, 2016.

(51) Int. Cl.
*C12N 15/82* (2006.01)
*C07K 14/435* (2006.01)
*A01N 57/16* (2006.01)
*C12N 15/113* (2010.01)
*C07K 14/325* (2006.01)

(52) U.S. Cl.
CPC ......... *C12N 15/8286* (2013.01); *A01N 57/16* (2013.01); *C07K 14/325* (2013.01); *C07K 14/43563* (2013.01); *C12N 15/113* (2013.01); *C12N 15/8218* (2013.01); *C12N 2310/14* (2013.01); *Y02A 40/162* (2018.01)

(58) Field of Classification Search
CPC .................................................. C12N 15/8286
USPC .......................................................... 800/279
See application file for complete search history.

(56) References Cited

U.S. PATENT DOCUMENTS

| | | | |
|---|---|---|---|
| 2009/0285784 A1* | 11/2009 | Raemaekers | A01N 57/16 424/93.2 |
| 2010/0192265 A1 | 7/2010 | Anderson et al. | |
| 2011/0154545 A1 | 6/2011 | Anderson et al. | |
| 2016/0230186 A1* | 8/2016 | Baum | C12N 15/8286 |

FOREIGN PATENT DOCUMENTS

| | | |
|---|---|---|
| WO | 2011025860 | 3/2011 |
| WO | 2014153254 | 9/2014 |

OTHER PUBLICATIONS

Yibrah et al. 1993, Hereditas 118:273-2890.*
Thomas et al. 2001, The Plant Journal 25(4):417-425.*
Fourgoux-Nicol et al 1999, Plant Molecular Biology 40 :857-872.*
In re: Stepan Company; 2016-1811; Appeal from Patent Trail and Appeal Board in U.S. Appl. No. 12/456,567; Decided: Aug. 25, 2017; 15 pgs.

* cited by examiner

*Primary Examiner* — Li Zheng
(74) *Attorney, Agent, or Firm* — Magleby Cataxinos & Greenwood

(57) ABSTRACT

This disclosure concerns nucleic acid molecules and methods of use thereof for control of insect pests through RNA interference-mediated inhibition of target coding and transcribed non-coding sequences in insect pests, including coleopteran and/or hemipteran pests. The disclosure also concerns methods for making transgenic plants that express nucleic acid molecules useful for the control of insect pests, and the plant cells and plants obtained thereby.

33 Claims, 2 Drawing Sheets
Specification includes a Sequence Listing.

SEQUENCE LISTING

<160> NUMBER OF SEQ ID NOS: 101

<210> SEQ ID NO 1
<211> LENGTH: 4901
<212> TYPE: DNA
<213> ORGANISM: Diabrotica virgifera

<400> SEQUENCE: 1

```
cgtatgtcgg cgatgtgcgc gaaaatcatt ttcttcactt ttctctatga tttttatata       60
attgtggaaa atcataattt cgccatatta tgcaacattt tttgtttttg aataaagtgc      120
aaggctctca cacgtccgcc atcacgacag tttgtggcaa gcttggccag cgggtatgtg      180
ttaggtgagt gagagtggtg tagctccgta ttttcacga ttctaatgtg gattatcact       240
caaaagacgc agatccaagc tatgatggct tttatctact aagaaaccat ttgtaaaatg      300
gaatgtgatt tgtatcggct gaagattata accagctgat tggtaggccc aggtcattat      360
taaccaaaac tatttgcgga ggaaaaatgg aacgcccacc ccgaaacgaa cccactgtgg      420
acccagtgaa tggagtggtc caaccactag tccagccacc tccagagagt ccgggccgcg      480
tcaccaatca acttcagttt ttacagaaaa ctgtgttaaa ggctgtctgg aagcaccaat      540
tcgcttggcc cttccagcaa cccgtcgatg ctagaaaact caacttgccc gactatcata      600
ggataattaa acagccaatg gacctgggaa caattaagaa aagactagac aacaattact      660
actggtcggg caaagagtgc atccaagact tcaacacgat gtttacaaac tgctatgtct      720
acaacaagcc tggagaggat gttgttgtca tggctcaaac gttagaaaag gtatttttga      780
caaaagtggc ggatatgcca aaggaggaat ttgttgttga atcgcccggt aaagcggag       840 cggcaaaagg aaagaagggg cggaccagta cagcgggcgc tgtcagtgca cccccaacac      900
caactacagc caccgctggt tcgggaggca ggggtaggcc tcccgccact gtctcttcta      960
caagcgccac tccagttgct accactacag gatcttcagg gttacctta ggcactcaag     1020 caccggctac agtacctggc agcaccgcaa ctaccaccat agcggcggcc agcaccaaca     1080
acagctctct gtcgaatcag caactgaact cttcttccag ttccattcac ggaagcggct     1140
ccagtttagg aaattcctta gattccagca gcgtcatgcc tgccaacgtt atacctccgg     1200
cacaaccagc caaggtaaaa aagggcgtga aagaaaggc cgatactacg acgcctgcta     1260
cagcctacga ttatccgcca actttggagt cgaagtctgc aaagatatcg acgcgccgag     1320
```

```
agtccggtag gcaaatcaaa aagcccacca ggccagaact ggacggtcat ccgccacaac    1380
cccctccact taaaccaaaa gaaaaactac cagaatcact gaaagcctgc aatgaaatcc    1440
tcctagaatt gttctctaag aaacattcta gttacgcctg gccttttttat caacccgtag    1500 acgcagaatt actcggtctg cacgactacc acgacatcat aaagaaaccg atggatttta    1560
gtactgtaaa aaataaaatg gaaaaccgag agtatcgcac tcctcaagac tttgccgccg    1620
acgttagact gatttttagt aattgttaca agtacaaccc ttctgaccac gatgtggttg    1680
ctatggcgag gaagttgcag gatgtgtttg aagtgaaata tgcaaagatt cccgatgaac    1740
ctgtcaatag ggtaggagcc cctgccgtta ataatatacc tgccaaatca gaaacgagta    1800
catccggttc cagttcggat tcttctagcg acacggaaga ttcggaggaa gaaaggcgaa    1860
acaaacaact gaagctgcta gaaaaagagt tgacggcaat gcaagaaaaa atgcgtaaat    1920
tggtagacga gagctcgaaa aagaaaaaag aaaagaaaaa ggacaaagtg aaaaagaaac    1980
cgacatcagg tgggtctctg gcgaacgcct cactatcaac tctaccgaac agcagcagcg    2040
cgggcttggg taagccgggt gccggtggtc acggggctct aaacaagtca acaacaaca    2100 actcaatagc ggcggacagc gttgacgaca gcatcgccag tgttgtgtcg ggggccgatc    2160
taaagatggc cgagtcgcac catccgcaaa ctggaacagg cgctcaccat ccgccggcag    2220
gcaaatccct gaacatgcat cacaacatga cggctaacgc tggcgccaac gcttccgcgc    2280
aggctaaaac acctaaaagt aaaggactcc gcggcaataa acccgctgca gctaccaacg    2340
cggctcccaa caagagggtc aaagccaaca acaaagctgg tgcgggtagg aagaagaacg    2400
cagcacaacc accacctatg cagttcgatt ctgaggacga agacaacgcc aaaccgatgt    2460
cttacgacga gaaacggcag ttgtctttgg atattaataa attaccaggt gacaaattgg    2520
gtagagttgt acatataatc caatccaggg aaccgtcgtt gagggattcc aatcctgacg    2580
aaatcgagat cgatttcgaa acgctgaaac cctcaacact cagagaatta gagagttacg    2640
ttgcgtcgtg tcttcgcaaa aagccacata aaaaagtagc gggcaaatct aaggacgaac    2700
aaatagcgga gaagaagcaa gagttagaga aaagactaat agacgtaaac gataaaatcg    2760
gcaactccaa gaaggccccc aaaaaagatg aagccaacaa ggtagaccca acgggcgcgg    2820
gaggtccctc aggccgccta tcctctagtt ccagcagttc ggactccgac agcagtagta    2880
gcagtttgtc ctctagttct agcgactcca gtgacgtga agcaggtggg acggcgaacc    2940
ggcaggccaa aaagaaagcg aataaaaaat cacccaatcc ttctctaggc agttccacca    3000
ccactacgac tataaaagtg ccgccgcctc aaacgacggc aacacctgca ccgccgtcac    3060
aagccgcacc agctatcacg acagcagcaa ccgctaattt aaccacaact gtaaccgtac    3120
caccacttac taccacaacg acaaatacga tagctccaac aatcgggaca tcccagaaca    3180
atattccggg cagcagcagt aagcaacgag ttatggacag ttttaagcat tccagaatag    3240
gaacgaaaaa gaaaaataac gacaaaccac atcataacgt caaaaacact aagccttgct    3300
cgagcttggc caaagggaaa tcaccacaga acaatatccc aggcggcagc agtaaacaaa    3360
ctaaagaaaa ggccgataga gagaaacaaa ggctggagaa cttagaaatg aagcggcaac    3420
agagggaaca agcggagagg gagaggttac gggcggaaaa cgaaaggcga agggaacggg    3480
aagaagaaga tgcgctcgag aaagcaagga aggctgtagc ggagcagcaa cagcctatag    3540
caagccaaag ggtggaagaa ctgaggtcgt cgcctggtga aggaagtaca tctccaggtt    3600
ccttaagttc tggttccgaa aggatatcgg agcgagaaag gcagaggttg caggagcagg    3660
```

-continued

```
aaaggcgaag aagagaagtg atggccaata agatagatat gaacatgcag agtgatctaa    3720
tggctgcttt cgaaggttcg ttatgaacgg tgatagtcgt gtgcgtttga ctgaatatta    3780
aagataatag aaaaagagac tccacgagcc aattttttgt gtatttatgt atttatatga    3840
caattttaat aggtgttaaa taaaatgtta gacgctcaaa aattttttgaa aaatgcttcc   3900
attatgatga gtttcgcttc ggatatatac ctctgatttc tttgagttga tcattttttt    3960
gtgttcgtgg cttgactcga ttttaaatat ttttttatata taatatataa gttggacatt   4020
ttcaacatgg tttgtatata taacactata aattgattat aaagttgtac ataatgatgt    4080
tgggttgatt attgtgttag tttttatttt attgtctatt cctccttgtc attgttttat    4140
tttaaagcat cttttgactt tcacggctac aggacggtcc taatatgcgg cccaatccac    4200
ttgcagatca tttcaattat aatattaata ttattttaaa atatttgtac aaaacgaaga    4260
ggaatgtgtt aaattcaagt gatcagcatt ggattgtaca cctgtgcaca cctttaaatt    4320
attggcgtca atgttaggat gactctttca cataaacctt gtcctacaca ttgacttaca    4380
gtgggtattt aaattattaa agccacacag agaagatttt tgtctaaaag ggatttgtat    4440
atgaattcca aggtatattg aatgtttatt cacattttgt ttcatgatca cactttagga    4500
tttaaaaagg ataggaagaa attggacttt ttcatgaaaa tatttaaaat tttaccatat    4560
gcataatatt tgacgatacc acccatttct tgttgcttta agctcgacac taattgattt    4620
gatatttcct tttttcatca actttcaaga ttttcaaatg catcaaaatc tggctagttt    4680
gcgggccagt cgaatatttt acatatagat aacgtatgca gtaagcgaca cgctactaga    4740
caaatggtag gtacctaatt gctatgcttt tgggctaatc cggtccgttc tcatgtgact    4800
ttcatgtcta tcgtgtcatg tgactctaag ccgcacatca agaaacatg aaatgtaaat    4860
cacgtttcat ggaagtgaaa caccgctaaa caaatagacg t                         4901
```

<210> SEQ ID NO 2
<211> LENGTH: 1119
<212> TYPE: PRT
<213> ORGANISM: Diabrotica virgifera

<400> SEQUENCE: 2

```
Met Glu Arg Pro Pro Arg Asn Glu Pro Thr Val Asp Pro Val Asn Gly
1               5                   10                  15

Val Val Gln Pro Leu Val Gln Pro Pro Glu Ser Pro Gly Arg Val
            20                  25                  30

Thr Asn Gln Leu Gln Phe Leu Gln Lys Thr Val Leu Lys Ala Val Trp
        35                  40                  45

Lys His Gln Phe Ala Trp Pro Phe Gln Gln Pro Val Asp Ala Arg Lys
    50                  55                  60

Leu Asn Leu Pro Asp Tyr His Arg Ile Ile Lys Gln Pro Met Asp Leu
65                  70                  75                  80

Gly Thr Ile Lys Lys Arg Leu Asp Asn Asn Tyr Tyr Trp Ser Gly Lys
                85                  90                  95

Glu Cys Ile Gln Asp Phe Asn Thr Met Phe Thr Asn Cys Tyr Val Tyr
            100                 105                 110

Asn Lys Pro Gly Glu Asp Val Val Met Ala Gln Thr Leu Glu Lys
        115                 120                 125

Val Phe Leu Thr Lys Val Ala Asp Met Pro Lys Glu Glu Phe Val Val
    130                 135                 140

Glu Ser Pro Gly Lys Ala Gly Ala Ala Lys Gly Lys Lys Gly Arg Thr
145                 150                 155                 160
```

-continued

```
Ser Thr Ala Gly Ala Val Ser Ala Pro Pro Thr Pro Thr Thr Ala Thr
                165                 170                 175

Ala Gly Ser Gly Gly Arg Gly Arg Pro Pro Ala Thr Val Ser Ser Thr
            180                 185                 190

Ser Ala Thr Pro Val Ala Thr Thr Thr Gly Ser Ser Gly Leu Pro Leu
            195                 200                 205

Gly Thr Gln Ala Pro Ala Thr Val Pro Gly Ser Thr Ala Thr Thr Thr
        210                 215                 220

Ile Ala Ala Ala Ser Thr Asn Asn Ser Ser Leu Ser Asn Gln Gln Leu
225                 230                 235                 240

Asn Ser Ser Ser Ser Ile His Gly Ser Gly Ser Ser Leu Gly Asn
                245                 250                 255

Ser Leu Asp Ser Ser Ser Val Met Pro Ala Asn Val Ile Pro Pro Ala
                260                 265                 270

Gln Pro Ala Lys Val Lys Lys Gly Val Lys Arg Lys Ala Asp Thr Thr
            275                 280                 285

Thr Pro Ala Thr Ala Tyr Asp Tyr Pro Pro Thr Leu Glu Ser Lys Ser
        290                 295                 300

Ala Lys Ile Ser Thr Arg Arg Glu Ser Gly Arg Gln Ile Lys Lys Pro
305                 310                 315                 320

Thr Arg Pro Glu Leu Asp Gly His Pro Pro Gln Pro Pro Leu Lys
                325                 330                 335

Pro Lys Glu Lys Leu Pro Glu Ser Leu Lys Ala Cys Asn Glu Ile Leu
                340                 345                 350

Leu Glu Leu Phe Ser Lys Lys His Ser Ser Tyr Ala Trp Pro Phe Tyr
                355                 360                 365

Gln Pro Val Asp Ala Glu Leu Leu Gly Leu His Asp Tyr His Asp Ile
        370                 375                 380

Ile Lys Lys Pro Met Asp Phe Ser Thr Val Lys Asn Lys Met Glu Asn
385                 390                 395                 400

Arg Glu Tyr Arg Thr Pro Gln Asp Phe Ala Ala Asp Val Arg Leu Ile
                405                 410                 415

Phe Ser Asn Cys Tyr Lys Tyr Asn Pro Ser Asp His Asp Val Val Ala
                420                 425                 430

Met Ala Arg Lys Leu Gln Asp Val Phe Glu Val Lys Tyr Ala Lys Ile
            435                 440                 445

Pro Asp Glu Pro Val Asn Arg Val Gly Ala Pro Ala Val Asn Asn Ile
        450                 455                 460

Pro Ala Lys Ser Glu Thr Ser Thr Ser Gly Ser Ser Ser Asp Ser Ser
465                 470                 475                 480

Ser Asp Thr Glu Asp Ser Glu Glu Arg Arg Asn Lys Gln Leu Lys
                485                 490                 495

Leu Leu Glu Lys Glu Leu Thr Ala Met Gln Glu Lys Met Arg Lys Leu
                500                 505                 510

Val Asp Glu Ser Ser Lys Lys Lys Glu Lys Lys Lys Asp Lys Val
            515                 520                 525

Lys Lys Lys Pro Thr Ser Gly Gly Ser Leu Ala Asn Ala Ser Leu Ser
530                 535                 540

Thr Leu Pro Asn Ser Ser Ser Ala Gly Leu Gly Lys Pro Gly Ala Gly
545                 550                 555                 560

Gly His Gly Ala Leu Asn Lys Ser Asn Asn Asn Ser Ile Ala Ala
                565                 570                 575
```

```
Asp Ser Val Asp Asp Ser Ile Ala Ser Val Val Ser Gly Ala Asp Leu
            580                 585                 590

Lys Met Ala Glu Ser His His Pro Gln Thr Gly Thr Gly Ala His His
            595                 600                 605

Pro Pro Ala Gly Lys Ser Leu Asn Met His His Asn Met Thr Ala Asn
            610                 615                 620

Ala Gly Ala Asn Ala Ser Ala Gln Ala Lys Thr Pro Lys Ser Lys Gly
625                 630                 635                 640

Leu Arg Gly Asn Lys Pro Ala Ala Thr Asn Ala Ala Pro Asn Lys
            645                 650                 655

Arg Val Lys Ala Asn Asn Lys Ala Gly Ala Gly Arg Lys Lys Asn Ala
            660                 665                 670

Ala Gln Pro Pro Pro Met Gln Phe Asp Ser Glu Asp Glu Asn Ala
            675                 680                 685

Lys Pro Met Ser Tyr Asp Glu Lys Arg Gln Leu Ser Leu Asp Ile Asn
            690                 695                 700

Lys Leu Pro Gly Asp Lys Leu Gly Arg Val Val His Ile Ile Gln Ser
705                 710                 715                 720

Arg Glu Pro Ser Leu Arg Asp Ser Asn Pro Asp Glu Ile Glu Ile Asp
            725                 730                 735

Phe Glu Thr Leu Lys Pro Ser Thr Leu Arg Glu Leu Glu Ser Tyr Val
            740                 745                 750

Ala Ser Cys Leu Arg Lys Lys Pro His Lys Lys Val Ala Gly Lys Ser
            755                 760                 765

Lys Asp Glu Gln Ile Ala Glu Lys Lys Gln Leu Glu Lys Arg Leu
770                 775                 780

Ile Asp Val Asn Asp Lys Ile Gly Asn Ser Lys Lys Ala Pro Lys Lys
785                 790                 795                 800

Asp Glu Ala Asn Lys Val Asp Pro Thr Gly Ala Gly Pro Ser Gly
            805                 810                 815

Arg Leu Ser Ser Ser Ser Ser Ser Asp Ser Asp Ser Ser Ser
            820                 825                 830

Ser Leu Ser Ser Ser Ser Asp Ser Ser Asp Ser Glu Ala Gly Gly
            835                 840                 845

Thr Ala Asn Arg Gln Ala Lys Lys Lys Ala Asn Lys Lys Ser Pro Asn
850                 855                 860

Pro Ser Leu Gly Ser Ser Thr Thr Thr Thr Ile Lys Val Pro Pro
865                 870                 875                 880

Pro Gln Thr Thr Ala Thr Pro Ala Pro Pro Ser Gln Ala Ala Pro Ala
            885                 890                 895

Ile Thr Thr Ala Ala Thr Ala Asn Leu Thr Thr Thr Val Thr Val Pro
            900                 905                 910

Pro Leu Thr Thr Thr Thr Thr Asn Thr Ile Ala Pro Thr Ile Gly Thr
            915                 920                 925

Ser Gln Asn Asn Ile Pro Gly Ser Ser Ser Lys Gln Arg Val Met Asp
930                 935                 940

Ser Phe Lys His Ser Arg Ile Gly Thr Lys Lys Asn Asn Asp Lys
945                 950                 955                 960

Pro His His Asn Val Lys Asn Thr Lys Pro Cys Ser Ser Leu Ala Lys
            965                 970                 975

Gly Lys Ser Pro Gln Asn Asn Ile Pro Gly Gly Ser Lys Gln Thr
            980                 985                 990

Lys Glu Lys Ala Asp Arg Glu Lys  Gln Arg Leu Glu Asn  Leu Glu Met
```

-continued

```
              995            1000            1005
Lys  Arg  Gln  Gln  Arg  Glu  Gln  Ala  Glu  Arg  Glu  Arg  Leu  Arg  Ala
    1010                1015                1020

Glu  Asn  Glu  Arg  Arg  Arg  Glu  Arg  Glu  Glu  Asp  Ala  Leu  Glu
    1025                1030                1035

Lys  Ala  Arg  Lys  Ala  Val  Ala  Glu  Gln  Gln  Pro  Ile  Ala  Ser
    1040                1045                1050

Gln  Arg  Val  Glu  Glu  Leu  Arg  Ser  Ser  Pro  Gly  Glu  Gly  Ser  Thr
    1055                1060                1065

Ser  Pro  Gly  Ser  Leu  Ser  Ser  Gly  Ser  Glu  Arg  Ile  Ser  Glu  Arg
    1070                1075                1080

Glu  Arg  Gln  Arg  Leu  Gln  Glu  Gln  Glu  Arg  Arg  Arg  Arg  Glu  Val
    1085                1090                1095

Met  Ala  Asn  Lys  Ile  Asp  Met  Asn  Met  Gln  Ser  Asp  Leu  Met  Ala
    1100                1105                1110

Ala  Phe  Glu  Gly  Ser  Leu
    1115
```

<210> SEQ ID NO 3
<211> LENGTH: 4656
<212> TYPE: DNA
<213> ORGANISM: Diabrotica virgifera

<400> SEQUENCE: 3

```
agagaagcca tttgtatgac ctcaaaaagt aaatctataa tcctttgaca tcgtaacgga      60
acttgtaaaa tcagcaaata ttttgaagta tttaatagca caatcgtatt taaatccaat     120
atttacagt attttgata tatttaactc ttttataag gcaatatcag taatgaagat         180
tatttgttca gtgcaaggct ctcacacgtc cgccatcacg acagtttgtg gcaagcttgg      240
ccagcgggta tgtgttaggt gagtgagagt ggtgtagctc cgtatttttc acgattctaa     300
tgtggattat cactcaaaag acgcagatcc aagctatgat ggcttttatc tactaagaaa     360
ccatttgtaa aatggaatgt gatttgtatc ggctgaagat tataaccagc tgattggtag     420
gcccaggtca ttattaacca aaactatttg cggaggaaaa atggaacgcc caccccgaaa     480
cgaacccact gtggacccag tgaatggagt ggtccaacca ctagtccagc cacctccaga     540
gagtccgggc gcgtcacca atcaacttca gttttttacag aaaactgtgt taaaggctgt     600
ctggaagcac caattcgctt ggcccttcca gcaacccgtc gatgctagaa aactcaactt      660
gcccgactat cataggataa ttaaacagcc aatggacctg gaacaatta agaaaagact       720
agacaacaat tactactggt cgggcaaaga gtgcatccaa gacttcaaca cgatgtttac     780
aaactgctat gtctacaaca agcctggaga ggatgttgtt gtcatggctc aaacgttaga     840
aaggtatttt ttgacaaaag tggcggatat gccaaaggag gaatttgttg ttgaatcgcc     900
cggtaaagcg ggagcggcaa aaggaaagaa ggggcggacc agtacagcgg gcgctgtcag    960
tgcacccca acaccaacta cagccaccgc tggttcggga ggcagggta ggcctccgc       1020
cactgtctct tctacaagcg ccactccagt tgctaccact acaggatctt cagggttacc    1080
tttaggcact caagcaccgg ctacagtacc tggcagcacc gcaactacca ccatagcggc    1140
ggccagcacc aacaacagct ctctgtcgaa tcagcaactg aactcttctt ccagttccat    1200
tcacggaagc ggctccagtt taggaaaatt cttagattcc agcagcgtca tgcctgccaa    1260
cgttatacct ccggcacaac cagccaaggt aaaaaagggc gtgaaaagaa aggccgatac    1320
tacgacgcct gctacagcct acgattatcc gccaactttg gagtcgaagt ctgcaaagat    1380
```

```
atcgacgcgc cgagagtccg gtaggcaaat caaaaagccc accaggccag aactggacgg    1440
tcatccgcca caacccctc cacttaaacc aaaagaaaaa ctaccagaat cactgaaagc     1500
ctgcaatgaa atcctcctag aattgttctc taagaaacat tctagttacg cctggccttt    1560
ttatcaaccc gtagacgcag aattactcgg tctgcacgac taccacgaca tcataaagaa    1620
accgatggat tttagtactg taaaaaataa aatggaaaac cgagagtatc gcactcctca    1680
agactttgcc gccgacgtta gactgatttt tagtaattgt tacaagtaca acccttctga    1740
ccacgatgtg gttgctatgg cgaggaagtt gcaggatgtg tttgaagtga aatatgcaaa    1800
gattcccgat gaacctgtca atagggtagg agcccctgcc gttaataata tacctgccaa    1860
atcagaaacg agtacatccg gttccagttc ggattcttct agcgacacgg aagattcgga    1920
ggaagaaagg cgaaacaaac aactgaagct gctagaaaaa gagttgacgg caatgcaaga    1980
aaaaatgcgt aaattggtag acgagagctc gaaaagaaa aagaaaaga aaaggacaa      2040 agtgaaaaag aaaccgacat caggtgggtc tctggcgaac gcctcactat caactctacc    2100
gaacagcagc agcgcgggct tgggactccg cggcaataaa cccgctgcag ctaccaacgc    2160
ggctcccaac aagagggtca aagccaacaa caaagctggt gcgggtagga agaagaacgc    2220
agcacaacca ccacctatgc agttcgattc tgaggacgaa gacaacgcca aaccgatgtc    2280
ttacgacgag aaacggcagt tgtctttgga tattaataaa ttaccaggtg acaaattggg    2340
tagagttgta catataatcc aatccaggga accgtcgttg agggattcca atcctgacga    2400
aatcgagatc gatttcgaaa cgctgaaacc ctcaacactc agagaattag agagttacgt    2460
tgcgtcgtgt cttcgcaaaa agccacgtaa gccatactat aaaaaagtag cgggcaaatc    2520
taaggacgaa caaatagcgg agaagaagca agagttagag aaaagactaa tagacgtaaa    2580
cgataaaatc ggcaactcca agaaggcccc caaaaaagat gaagccaaca aggtagaccc    2640
aacgggcgcg ggaggtccct caggccgcct atcctctagt tccagcagtt cggactccga    2700
cagcagtagt agcagtttgt cctctagttc tagcgactcc agtgacagtg aagcaggtgg    2760
gacggcgaac cggcaggcca aaagaaaagc gaataaaaaa tcacccaatc cttctctagg    2820
cagttccacc accactacga ctataaaagt gccgccgcct caaacgacgg caacacctgc    2880
accgccgtca caagccgcac cagctatcac gacagcagca accgctaatt taaccacaac    2940
tgtaaccgta ccaccactta ctaccacaac gacaaatacg atagctccac caattcaacc    3000
ggcgccagtt ccaaacgtcg cagttcccgc gcaaacgacg ccagccgcac ccgccttcac    3060
gccgagcata accatcaaac catcactaca ggccgcccct atcgctccga cggtgccgcc    3120
tcttatcaag tcaatcgaga aactgcctgt cacaactctc ttacctccta ccgttcctac    3180
gataacgcct ccaacagtac ctcaagctcc caaatcggta gcgctaccga ctccttctcc    3240
tgataaacct aaacctaaca ttatttctcc cattggtacc tttaccgacc ctatcgaaca    3300
atcattggct agtcttgaac acgatattaa gcagaatgat cctatggacg tcattacggc    3360
gtctactatg atgcaaatgc ctactacact aaccaatcct atcgtgtcac atccacatcc    3420
taacttaaac ttaaatccca ccattaacca tcctatttta cagcctagca cacttagtat    3480
ggacttaaaa gcgcctatta tgggcactat ggcgccgagc aataccatgt tgcatcacgg    3540
attgcaacaa gcaatggaaa cggatatcag tatacctcca ccccccacca acatgctgca    3600
tggacagaac aacggttttg gcatgaaaca caatttgat ctgactacaa acaacaacgg    3660
tctttcctcg atgggtctgc ccatggaaat gtcgatatcg tcaatgtttg atccaattcc    3720
```

```
acaaaatatt aatcccatga tgaagaacga ttcccaactc aagatggacg atcgcatgga    3780
taccttaggt ggacttttga acgacaagaa gtccaatctc ctcatacaaa agccgatgtc    3840
gcagtcgttt ggtttcaaga atgacaaacc agatcataac gtcaaaaacg ctagttcctg    3900
gtcgagtttg gccaaaggaa aatcaccaca aaacaatatt ccgggcggca gcagtaaaca    3960
acaagttatg gatagtttta aggcattcca aaataaagct aaagaaaagg ccgatagaga    4020
gaaacaaagg ctggagaact tagaaatgaa gcggcaacag agggaacaag cggagaggga    4080
gaggttacgg gcggaaaacg aaaggcgaag ggaacgggaa gaagaagatg cgctcgagaa    4140
agcaaggaag gctgtagcgg agcagcaaca gcctatagca agccaaaggg tggaagaact    4200
gaggtcgtcg cctggtgaag gaagtacatc tccaggttcc ttaagttctg gttccgaaag    4260
gatatcggag cgagaaaggc agaggttgca ggagcaggaa aggcgaagaa gagaagtgat    4320
ggccaataag atagatatga acatgcagag tgatctaatg gctgctttcg aaggttcgtt    4380
atgaacggtg atagtcgtgt gcgtttgact gaatattaaa gataatagaa aaagagactc    4440
cacgagccaa ttttttgtgt atttatgtat ttatatgaca attttaatag gtgttaaata    4500
aaatgttaga cgctcaaaaa ttttttgaaaa atgcttccat tatgatgagt ttcgcttcgg    4560
atatatacct ctgatttctt tgagttgatc attttttttgt gttcgtggct tgactcgatt    4620
ttaaatattt tttatatata atatataagt tggaca                             4656
```

<210> SEQ ID NO 4
<211> LENGTH: 1307
<212> TYPE: PRT
<213> ORGANISM: Diabrotica virgifera

<400> SEQUENCE: 4

```
Met Glu Arg Pro Pro Arg Asn Glu Pro Thr Val Asp Pro Val Asn Gly
1               5                   10                  15

Val Val Gln Pro Leu Val Gln Pro Pro Glu Ser Pro Gly Arg Val
            20                  25                  30

Thr Asn Gln Leu Gln Phe Leu Gln Lys Thr Val Leu Lys Ala Val Trp
        35                  40                  45

Lys His Gln Phe Ala Trp Pro Phe Gln Gln Pro Val Asp Ala Arg Lys
    50                  55                  60

Leu Asn Leu Pro Asp Tyr His Arg Ile Ile Lys Gln Pro Met Asp Leu
65                  70                  75                  80

Gly Thr Ile Lys Lys Arg Leu Asp Asn Asn Tyr Tyr Trp Ser Gly Lys
                85                  90                  95

Glu Cys Ile Gln Asp Phe Asn Thr Met Phe Thr Asn Cys Tyr Val Tyr
            100                 105                 110

Asn Lys Pro Gly Glu Asp Val Val Met Ala Gln Thr Leu Glu Lys
        115                 120                 125

Val Phe Leu Thr Lys Val Ala Asp Met Pro Lys Glu Glu Phe Val Val
    130                 135                 140

Glu Ser Pro Gly Lys Ala Gly Ala Ala Lys Lys Lys Gly Arg Thr
145                 150                 155                 160

Ser Thr Ala Gly Ala Val Ser Ala Pro Pro Thr Pro Thr Thr Ala Thr
                165                 170                 175

Ala Gly Ser Gly Gly Arg Gly Arg Pro Pro Ala Thr Val Ser Ser Thr
            180                 185                 190

Ser Ala Thr Pro Val Ala Thr Thr Thr Gly Ser Ser Gly Leu Pro Leu
        195                 200                 205
```

```
Gly Thr Gln Ala Pro Ala Thr Val Pro Gly Ser Thr Ala Thr Thr Thr
210                 215                 220

Ile Ala Ala Ala Ser Thr Asn Asn Ser Ser Leu Ser Asn Gln Gln Leu
225                 230                 235                 240

Asn Ser Ser Ser Ser Ile His Gly Ser Gly Ser Ser Leu Gly Asn
                245                 250                 255

Ser Leu Asp Ser Ser Ser Val Met Pro Ala Asn Val Ile Pro Pro Ala
                260                 265                 270

Gln Pro Ala Lys Val Lys Lys Gly Val Lys Arg Lys Ala Asp Thr Thr
                275                 280                 285

Thr Pro Ala Thr Ala Tyr Asp Tyr Pro Pro Thr Leu Glu Ser Lys Ser
290                 295                 300

Ala Lys Ile Ser Thr Arg Arg Glu Ser Gly Arg Gln Ile Lys Lys Pro
305                 310                 315                 320

Thr Arg Pro Glu Leu Asp Gly His Pro Pro Gln Pro Pro Leu Lys
                325                 330                 335

Pro Lys Glu Lys Leu Pro Glu Ser Leu Lys Ala Cys Asn Glu Ile Leu
                340                 345                 350

Leu Glu Leu Phe Ser Lys Lys His Ser Ser Tyr Ala Trp Pro Phe Tyr
                355                 360                 365

Gln Pro Val Asp Ala Glu Leu Leu Gly Leu His Asp Tyr His Asp Ile
370                 375                 380

Ile Lys Lys Pro Met Asp Phe Ser Thr Val Lys Asn Lys Met Glu Asn
385                 390                 395                 400

Arg Glu Tyr Arg Thr Pro Gln Asp Phe Ala Ala Asp Val Arg Leu Ile
                405                 410                 415

Phe Ser Asn Cys Tyr Lys Tyr Asn Pro Ser Asp His Asp Val Val Ala
                420                 425                 430

Met Ala Arg Lys Leu Gln Asp Val Phe Glu Val Lys Tyr Ala Lys Ile
                435                 440                 445

Pro Asp Glu Pro Val Asn Arg Val Gly Ala Pro Ala Val Asn Asn Ile
                450                 455                 460

Pro Ala Lys Ser Glu Thr Ser Thr Ser Gly Ser Ser Ser Asp Ser Ser
465                 470                 475                 480

Ser Asp Thr Glu Asp Ser Glu Glu Arg Arg Asn Lys Gln Leu Lys
                485                 490                 495

Leu Leu Glu Lys Glu Leu Thr Ala Met Gln Glu Lys Met Arg Lys Leu
                500                 505                 510

Val Asp Glu Ser Lys Lys Lys Glu Lys Lys Lys Asp Lys Val
                515                 520                 525

Lys Lys Lys Pro Thr Ser Gly Gly Ser Leu Ala Asn Ala Ser Leu Ser
530                 535                 540

Thr Leu Pro Asn Ser Ser Ala Gly Leu Gly Leu Arg Gly Asn Lys
545                 550                 555                 560

Pro Ala Ala Ala Thr Asn Ala Pro Asn Lys Arg Val Lys Ala Asn
                565                 570                 575

Asn Lys Ala Gly Ala Gly Arg Lys Lys Asn Ala Ala Gln Pro Pro Pro
                580                 585                 590

Met Gln Phe Asp Ser Glu Asp Glu Asp Asn Ala Lys Pro Met Ser Tyr
                595                 600                 605

Asp Glu Lys Arg Gln Leu Ser Leu Asp Ile Asn Lys Leu Pro Gly Asp
                610                 615                 620

Lys Leu Gly Arg Val Val His Ile Ile Gln Ser Arg Glu Pro Ser Leu
```

```
                    625               630                635               640
Arg Asp Ser Asn Pro Asp Glu Ile Glu Ile Asp Phe Glu Thr Leu Lys
                        645                650               655

Pro Ser Thr Leu Arg Glu Leu Glu Ser Tyr Val Ala Ser Cys Leu Arg
                660               665                670

Lys Lys Pro Arg Lys Pro Tyr Tyr Lys Lys Val Ala Gly Lys Ser Lys
                    675               680                685

Asp Glu Gln Ile Ala Glu Lys Lys Gln Glu Leu Glu Lys Arg Leu Ile
    690               695                700

Asp Val Asn Asp Lys Ile Gly Asn Ser Lys Lys Ala Pro Lys Lys Asp
705               710                715                720

Glu Ala Asn Lys Val Asp Pro Thr Gly Ala Gly Pro Ser Gly Arg
                725                730                735

Leu Ser Ser Ser Ser Ser Ser Asp Ser Asp Ser Ser Ser Ser
                740                745                750

Leu Ser Ser Ser Ser Asp Ser Ser Asp Ser Glu Ala Gly Gly Thr
                755                760                765

Ala Asn Arg Gln Ala Lys Lys Lys Ala Asn Lys Lys Ser Pro Asn Pro
770                775                780

Ser Leu Gly Ser Ser Thr Thr Thr Thr Ile Lys Val Pro Pro Pro
785                790                795                800

Gln Thr Thr Ala Thr Pro Ala Pro Pro Ser Gln Ala Ala Pro Ala Ile
                    805                810                815

Thr Thr Ala Ala Thr Ala Asn Leu Thr Thr Val Thr Val Pro Pro
                820                825                830

Leu Thr Thr Thr Thr Thr Asn Thr Ile Ala Pro Pro Ile Gln Pro Ala
                835                840                845

Pro Val Pro Asn Val Ala Val Pro Ala Gln Thr Thr Pro Ala Ala Pro
    850                855                860

Ala Phe Thr Pro Ser Ile Thr Ile Lys Pro Ser Leu Gln Ala Ala Pro
865                870                875                880

Ile Ala Pro Thr Val Pro Pro Leu Ile Lys Ser Ile Glu Lys Leu Pro
                885                890                895

Val Thr Thr Leu Leu Pro Pro Thr Val Pro Thr Ile Thr Pro Pro Thr
                900                905                910

Val Pro Gln Ala Pro Lys Ser Val Ala Leu Pro Thr Pro Ser Pro Asp
                915                920                925

Lys Pro Lys Pro Asn Ile Ile Ser Pro Ile Gly Thr Phe Thr Asp Pro
930                935                940

Ile Glu Gln Ser Leu Ala Ser Leu Glu His Asp Ile Lys Gln Asn Asp
945                950                955                960

Pro Met Asp Val Ile Thr Ala Ser Thr Met Met Gln Met Pro Thr Thr
                965                970                975

Leu Thr Asn Pro Ile Val Ser His Pro His Pro Asn Leu Asn Leu Asn
                980                985                990

Pro Thr Ile Asn His Pro Ile Leu  Gln Pro Ser Thr Leu  Ser Met Asp
            995                1000               1005

Leu Lys  Ala Pro Ile Met Gly  Thr Met Ala Pro Ser  Asn Thr Met
    1010               1015               1020

Leu His  His Gly Leu Gln Gln  Ala Met Glu Thr Asp  Ile Ser Ile
    1025               1030               1035

Pro Pro  Pro Pro Thr Asn Met  Leu His Gly Gln Asn  Asn Gly Phe
    1040               1045               1050
```

Gly Met Lys His Asn Phe Asp Leu Thr Thr Asn Asn Asn Gly Leu
    1055                1060                1065

Ser Ser Met Gly Leu Pro Met Glu Met Ser Ile Ser Ser Met Phe
    1070                1075                1080

Asp Pro Ile Pro Gln Asn Ile Asn Pro Met Met Lys Asn Asp Ser
    1085                1090                1095

Gln Leu Lys Met Asp Asp Arg Met Asp Thr Leu Gly Gly Leu Leu
    1100                1105                1110

Asn Asp Lys Lys Ser Asn Leu Leu Ile Gln Lys Pro Met Ser Gln
    1115                1120                1125

Ser Phe Gly Phe Lys Asn Asp Lys Pro Asp His Asn Val Lys Asn
    1130                1135                1140

Ala Ser Ser Trp Ser Ser Leu Ala Lys Gly Lys Ser Pro Gln Asn
    1145                1150                1155

Asn Ile Pro Gly Gly Ser Ser Lys Gln Gln Val Met Asp Ser Phe
    1160                1165                1170

Lys Ala Phe Gln Asn Lys Ala Lys Glu Lys Ala Asp Arg Glu Lys
    1175                1180                1185

Gln Arg Leu Glu Asn Leu Glu Met Lys Arg Gln Gln Arg Glu Gln
    1190                1195                1200

Ala Glu Arg Glu Arg Leu Arg Ala Glu Asn Glu Arg Arg Arg Glu
    1205                1210                1215

Arg Glu Glu Glu Asp Ala Leu Glu Lys Ala Arg Lys Ala Val Ala
    1220                1225                1230

Glu Gln Gln Gln Pro Ile Ala Ser Gln Arg Val Glu Glu Leu Arg
    1235                1240                1245

Ser Ser Pro Gly Glu Gly Ser Thr Ser Pro Gly Ser Leu Ser Ser
    1250                1255                1260

Gly Ser Glu Arg Ile Ser Glu Arg Glu Arg Gln Arg Leu Gln Glu
    1265                1270                1275

Gln Glu Arg Arg Arg Arg Glu Val Met Ala Asn Lys Ile Asp Met
    1280                1285                1290

Asn Met Gln Ser Asp Leu Met Ala Ala Phe Glu Gly Ser Leu
    1295                1300                1305

<210> SEQ ID NO 5
<211> LENGTH: 445
<212> TYPE: DNA
<213> ORGANISM: Diabrotica virgifera

<400> SEQUENCE: 5
tcttccgtgt cgctagaaga atccgaactg gaaccggatg tactcgtttc tgatttggca      60
ggtatattat taacggcagg ggctcctacc ctattgacag gttcatcggg aatctttgca     120
tatttcactt caaacacatc ctgcaacttc ctcgccatag caaccacatc gtggtcagaa     180
gggttgtact tgtaacaatt actaaaaatc agtctaacgt cggcggcaaa gtcttgagga     240
gtgcgatact ctcggttttc cattttattt tttacagtac taaaatccat cggtttcttt     300
atgatgtcgt ggtagtcgtg cagaccgagt aattctgcgt ctacggggttg ataaaaaggc    360 caggcgtaac tagaatgttt cttagagaac aattctagga ggatttcatt gcaggctttc     420
agtgattctg gtagttttc ttttg                                            445

<210> SEQ ID NO 6
<211> LENGTH: 482

<212> TYPE: DNA
<213> ORGANISM: Diabrotica virgifera

<400> SEQUENCE: 6

```
acttcctcgc catagcaacc acatcgtggt cagaagggtt gtacttgtaa caattactaa        60
aaatcagtct aacgtcggcg gcaaagtctt gaggagtgcg atactctcgg ttttccattt       120
tattttttac agtactaaaa tccatcggtt tctttatgat gtcgtggtag tcgtgcagac       180
cgagtaattc tgcgtctacg ggttgataaa aaggccaggc gtaactagaa tgtttcttag       240
agaacaattc taggaggatt tcattgcagg ctttcagtga ttctggtagt ttttcttttg       300
gtttaagtgg aggggttgt ggcggatgac cgtccagttc tggcctggtg ggcttttga        360
tttgcctacc ggactctcgg cgcgtcgata tctttgcaga cttcgactcc aaagttggcg       420
gataatcgta ggctgtagca ggcgtcgtag tatcggcctt tcttttcacg ccctttttta       480
cc                                                                     482
```

<210> SEQ ID NO 7
<211> LENGTH: 143
<212> TYPE: DNA
<213> ORGANISM: Diabrotica virgifera

<400> SEQUENCE: 7

```
gttcatcggg aatctttgca tatttcactt caaacacatc ctgcaacttc ctcgccatag        60
caaccacatc gtggtcagaa gggttgtact tgtaacaatt actaaaaatc agtctaacgt       120
cggcggcaaa gtcttgagga gtg                                              143
```

<210> SEQ ID NO 8
<211> LENGTH: 164
<212> TYPE: DNA
<213> ORGANISM: Diabrotica virgifera

<400> SEQUENCE: 8

```
acttcctcgc catagcaacc acatcgtggt cagaagggtt gtacttgtaa caattactaa        60
aaatcagtct aacgtcggcg gcaaagtctt gaggagtgcg atactctcgg ttttccattt       120
tattttttac agtactaaaa tccatcggtt tctttatgat gtcg                       164
```

<210> SEQ ID NO 9
<211> LENGTH: 24
<212> TYPE: DNA
<213> ORGANISM: Artificial Sequence
<220> FEATURE:
<223> OTHER INFORMATION: T7 promoter oligonucleotide

<400> SEQUENCE: 9

```
ttaatacgac tcactatagg gaga                                              24
```

<210> SEQ ID NO 10
<211> LENGTH: 503
<212> TYPE: DNA
<213> ORGANISM: Artificial Sequence
<220> FEATURE:
<223> OTHER INFORMATION: Partial YFP coding region

<400> SEQUENCE: 10

```
caccatgggc tccagcggcg ccctgctgtt ccacggcaag atcccctacg tggtggagat        60
ggagggcaat gtggatggcc acaccttcag catccgcgc aagggctacg gcatgccag       120
cgtgggcaag gtggatgccc agttcatctg caccaccggc gatgtgcccg tgccctggag       180
```

-continued

```
caccctggtg accaccctga cctacggcgc ccagtgcttc gccaagtacg gccccgagct      240
gaaggatttc tacaagagct gcatgcccga tggctacgtg caggagcgca ccatcacctt      300
cgagggcgat ggcaatttca agacccgcgc cgaggtgacc ttcgagaatg cagcgtgta      360 caatcgcgtg aagctgaatg ccagggctt caagaaggat ggccacgtgc tgggcaagaa      420
tctggagttc aatttcaccc cccactgcct gtacatctgg ggcgatcagg ccaatcacgg      480
cctgaagagc gccttcaaga tct                                              503
```

<210> SEQ ID NO 11
<211> LENGTH: 47
<212> TYPE: DNA
<213> ORGANISM: Artificial Sequence
<220> FEATURE:
<223> OTHER INFORMATION: Primer Dvv-fsh-1_For

<400> SEQUENCE: 11

```
ttaatacgac tcactatagg gagatcttcc gtgtcgctag aagaatc                    47
```

<210> SEQ ID NO 12
<211> LENGTH: 50
<212> TYPE: DNA
<213> ORGANISM: Artificial Sequence
<220> FEATURE:
<223> OTHER INFORMATION: Primer Dvv-fsh-1_Rev

<400> SEQUENCE: 12

```
ttaatacgac tcactatagg gagacaaaag aaaaactacc agaatcactg                 50
```

<210> SEQ ID NO 13
<211> LENGTH: 44
<212> TYPE: DNA
<213> ORGANISM: Artificial Sequence
<220> FEATURE:
<223> OTHER INFORMATION: Primer Dvv-fsh-2_For

<400> SEQUENCE: 13

```
ttaatacgac tcactatagg gagaacttcc tcgccatagc aacc                       44
```

<210> SEQ ID NO 14
<211> LENGTH: 49
<212> TYPE: DNA
<213> ORGANISM: Artificial Sequence
<220> FEATURE:
<223> OTHER INFORMATION: Primer Dvv-fsh-2_Rev

<400> SEQUENCE: 14

```
ttaatacgac tcactatagg gagaggtaaa aaagggcgtg aaaagaaag                  49
```

<210> SEQ ID NO 15
<211> LENGTH: 43
<212> TYPE: DNA
<213> ORGANISM: Artificial Sequence
<220> FEATURE:
<223> OTHER INFORMATION: Primer Dvv-fsh-1_v1_For

<400> SEQUENCE: 15

```
ttaatacgac tcactatagg gagagttcat cgggaatctt tgc                        43
```

<210> SEQ ID NO 16
<211> LENGTH: 42
<212> TYPE: DNA
<213> ORGANISM: Artificial Sequence
<220> FEATURE:
<223> OTHER INFORMATION: Primer Dvv-fsh-1_v1_Rev

<400> SEQUENCE: 16
ttaatacgac tcactatagg gagacactcc tcaagacttt gc         42

<210> SEQ ID NO 17
<211> LENGTH: 44
<212> TYPE: DNA
<213> ORGANISM: Artificial Sequence
<220> FEATURE:
<223> OTHER INFORMATION: Primer Dvv-fsh-2_v1_For

<400> SEQUENCE: 17
ttaatacgac tcactatagg gagaacttcc tcgccatagc aacc        44

<210> SEQ ID NO 18
<211> LENGTH: 49
<212> TYPE: DNA
<213> ORGANISM: Artificial Sequence
<220> FEATURE:
<223> OTHER INFORMATION: Primer Dvv-fsh-2_v1_Rev

<400> SEQUENCE: 18
ttaatacgac tcactatagg gagacgacat cataaagaaa ccgatggat   49

<210> SEQ ID NO 19
<211> LENGTH: 705
<212> TYPE: DNA
<213> ORGANISM: Artificial Sequence
<220> FEATURE:
<223> OTHER INFORMATION: YFP gene

<400> SEQUENCE: 19
atgtcatctg gagcacttct ctttcatggg aagattcctt acgttgtgga gatggaaggg 60
aatgttgatg gccacacctt tagcatacgt gggaaaggct acggagatgc ctcagtggga 120
aaggttgatg cacagttcat ctgcacaact ggtgatgttc ctgtgccttg gagcacactt 180
gtcaccactc tcacctatgg agcacagtgc tttgccaagt atggtccaga gttgaaggac 240
ttctacaagt cctgtatgcc agatggctat gtgcaagagc gcacaatcac ctttgaagga 300
gatggcaact tcaagactag ggctgaagtc acctttgaga atgggtctgt ctacaatagg 360
gtcaaactca atggtcaagg cttcaagaaa gatggtcatg tgttgggaaa gaacttggag 420
ttcaacttca ctccccactg cctctacatc tggggtgacc aagccaacca cggtctcaag 480
tcagccttca agatctgtca tgagattact ggcagcaaag gcgacttcat agtggctgac 540
cacacccaga tgaacactcc cattggtgga ggtccagttc atgttccaga gtatcatcac 600
atgtcttacc atgtgaaact ttccaaagat gtgacagacc acagagacaa catgtccttg 660
aaagaaactg tcagagctgt tgactgtcgc aagacctacc tttga 705

<210> SEQ ID NO 20
<211> LENGTH: 218
<212> TYPE: DNA
<213> ORGANISM: Diabrotica virgifera

<400> SEQUENCE: 20
tagctctgat gacagagccc atcgagtttc aagccaaaca gttgcataaa gctatcagcg 60
gattgggaac tgatgaaagt acaatmgtmg aaattttaag tgtmcacaac aacgatgaga 120
ttataagaat ttcccaggcc tatgaaggat tgtaccaacg mtcattggaa tctgatatca 180
aaggagatac ctcaggaaca ttaaaaaaga attattag 218

<210> SEQ ID NO 21
<211> LENGTH: 424
<212> TYPE: DNA
<213> ORGANISM: Diabrotica virgifera
<220> FEATURE:
<221> NAME/KEY: misc_feature
<222> LOCATION: (393)..(395)
<223> OTHER INFORMATION: n is a, c, g, or t

<400> SEQUENCE: 21

| | | | | | |
|---|---|---|---|---|---|
| ttgttacaag | ctggagaact | tctctttgct | ggaaccgaag | agtcagtatt | taatgctgta | 60 |
| ttctgtcaaa | gaaataaacc | acaattgaat | ttgatattcg | acaaatatga | agaaattgtt | 120 |
| gggcatccca | ttgaaaaagc | cattgaaaac | gagttttcag | gaaatgctaa | acaagccatg | 180 |
| ttacacctta | tccagagcgt | aagagatcaa | gttgcatatt | tggtaaccag | gctgcatgat | 240 |
| tcaatggcag | gcgtcggtac | tgacgataga | actttaatca | gaattgttgt | ttcgagatct | 300 |
| gaaatcgatc | tagaggaaat | caaacaatgc | tatgaagaaa | tctacagtaa | aaccttggct | 360 |
| gataggatag | cggatgacac | atctggcgac | tannnaaaag | ccttattagc | cgttgttggt | 420 |
| taag | | | | | | 424 |

<210> SEQ ID NO 22
<211> LENGTH: 397
<212> TYPE: DNA
<213> ORGANISM: Diabrotica virgifera

<400> SEQUENCE: 22

| | | | | | |
|---|---|---|---|---|---|
| agatgttggc | tgcatctaga | gaattacaca | agttcttcca | tgattgcaag | gatgtactga | 60 |
| gcagaatagt | ggaaaaacag | gtatccatgt | ctgatgaatt | gggaagggac | gcaggagctg | 120 |
| tcaatgccct | tcaacgcaaa | caccagaact | tcctccaaga | cctacaaaca | ctccaatcga | 180 |
| acgtccaaca | aatccaagaa | gaatcagcta | aacttcaagc | tagctatgcc | ggtgatagag | 240 |
| ctaaagaaat | caccaacagg | gagcaggaag | tggtagcagc | ctgggcagcc | ttgcagatcg | 300 |
| cttgcgatca | gagacacgga | aaattgagcg | atactggtga | tctattcaaa | ttctttaact | 360 |
| tggtacgaac | gttgatgcag | tggatggacg | aatggac | | | 397 |

<210> SEQ ID NO 23
<211> LENGTH: 490
<212> TYPE: DNA
<213> ORGANISM: Diabrotica virgifera

<400> SEQUENCE: 23

| | | | | | |
|---|---|---|---|---|---|
| gcagatgaac | accagcgaga | aaccaagaga | tgttagtggt | gttgaattgt | tgatgaacaa | 60 |
| ccatcagaca | ctcaaggctg | agatcgaagc | cagagaagac | aactttacgg | cttgtatttc | 120 |
| tttaggaaag | gaattgttga | gccgtaatca | ctatgctagt | gctgatatta | aggataaatt | 180 |
| ggtcgcgttg | acgaatcaaa | ggaatgctgt | actacagagg | tgggaagaaa | gatgggagaa | 240 |
| cttgcaactc | atcctcgagg | tataccaatt | cgccagagat | gcggccgtcg | ccgaagcatg | 300 |
| gttgatcgca | caagaaccct | acttgatgag | ccaagaacta | ggacacacca | ttgacgacgt | 360 |
| tgaaaacttg | ataagaaac | acgaagcgtt | cgaaaaatcg | gcagcggcgc | aagaagagag | 420 |
| attcagtgct | ttggagagac | tgacgacgtt | cgaattgaga | gaaataaaga | ggaaacaaga | 480 |
| agctgcccag | | | | | | 490 |

<210> SEQ ID NO 24
<211> LENGTH: 330

```
<212> TYPE: DNA
<213> ORGANISM: Diabrotica virgifera

<400> SEQUENCE: 24
agtgaaatgt tagcaaatat aacatccaag tttcgtaatt gtacttgctc agttagaaaa    60
tattctgtag tttcactatc ttcaaccgaa aatagaataa atgtagaacc tcgcgaactt   120
gcctttcctc caaaatatca agaacctcga caagtttggt tggagagttt agatacgata   180
gacgacaaaa aattgggtat tcttgagctg catcctgatg ttttgctac taatccaaga    240 atagatatta tacatcaaaa tgttagatgg caaagtttat atagatatgt aagctatgct   300
catacaaagt caagatttga agtgagaggt                                    330

<210> SEQ ID NO 25
<211> LENGTH: 320
<212> TYPE: DNA
<213> ORGANISM: Diabrotica virgifera

<400> SEQUENCE: 25
caaagtcaag atttgaagtg agaggtggag gtcgaaaacc gtggccgcaa aagggattgg    60
gacgtgctcg acatggttca attagaagtc cactttggag aggtggagga gttgttcatg   120
gaccaaaatc tccaaccct cattttaca tgattccatt ctacacccgt tgctgggtt     180 tgactagcgc actttcagta aaatttgccc aagatgactt gcacgttgtg gatagtctag   240
atctgccaac tgacgaacaa agttatatag aagagctggt caaaagccgc ttttggggt    300 ccttcttgtt ttatttgtag                                               320

<210> SEQ ID NO 26
<211> LENGTH: 47
<212> TYPE: DNA
<213> ORGANISM: Artificial Sequence
<220> FEATURE:
<223> OTHER INFORMATION: Primer YFP-F_T7

<400> SEQUENCE: 26
ttaatacgac tcactatagg gagacaccat gggctccagc ggcgccc                 47

<210> SEQ ID NO 27
<211> LENGTH: 23
<212> TYPE: DNA
<213> ORGANISM: Artificial Sequence
<220> FEATURE:
<223> OTHER INFORMATION: Primer YFP-R

<400> SEQUENCE: 27
agatcttgaa ggcgctcttc agg                                           23

<210> SEQ ID NO 28
<211> LENGTH: 23
<212> TYPE: DNA
<213> ORGANISM: Artificial Sequence
<220> FEATURE:
<223> OTHER INFORMATION: YFP-F

<400> SEQUENCE: 28
caccatgggc tccagcggcg ccc                                           23

<210> SEQ ID NO 29
<211> LENGTH: 47
<212> TYPE: DNA
<213> ORGANISM: Artificial Sequence
<220> FEATURE:
```

<223> OTHER INFORMATION: Primer YFP-R_T7

<400> SEQUENCE: 29
ttaatacgac tcactatagg gagaagatct tgaaggcgct cttcagg                    47

<210> SEQ ID NO 30
<211> LENGTH: 46
<212> TYPE: DNA
<213> ORGANISM: Artificial Sequence
<220> FEATURE:
<223> OTHER INFORMATION: Primer Ann-F1_T7

<400> SEQUENCE: 30
ttaatacgac tcactatagg gagagctcca acagtggttc cttatc                     46

<210> SEQ ID NO 31
<211> LENGTH: 29
<212> TYPE: DNA
<213> ORGANISM: Artificial Sequence
<220> FEATURE:
<223> OTHER INFORMATION: Primer Ann-R1

<400> SEQUENCE: 31
ctaataattc tttttaatg ttcctgagg                                         29

<210> SEQ ID NO 32
<211> LENGTH: 22
<212> TYPE: DNA
<213> ORGANISM: Artificial Sequence
<220> FEATURE:
<223> OTHER INFORMATION: Primer Ann-F1

<400> SEQUENCE: 32
gctccaacag tggttcctta tc                                               22

<210> SEQ ID NO 33
<211> LENGTH: 53
<212> TYPE: DNA
<213> ORGANISM: Artificial Sequence
<220> FEATURE:
<223> OTHER INFORMATION: Primer Ann-R1_T7

<400> SEQUENCE: 33
ttaatacgac tcactatagg gagactaata attctttttt aatgttcctg agg             53

<210> SEQ ID NO 34
<211> LENGTH: 48
<212> TYPE: DNA
<213> ORGANISM: Artificial Sequence
<220> FEATURE:
<223> OTHER INFORMATION: Primer Ann-F2_T7

<400> SEQUENCE: 34
ttaatacgac tcactatagg gagattgtta caagctggag aacttctc                   48

<210> SEQ ID NO 35
<211> LENGTH: 24
<212> TYPE: DNA
<213> ORGANISM: Artificial Sequence
<220> FEATURE:
<223> OTHER INFORMATION: Primer Ann-R2

<400> SEQUENCE: 35
cttaaccaac aacggctaat aagg                                             24

```
<210> SEQ ID NO 36
<211> LENGTH: 24
<212> TYPE: DNA
<213> ORGANISM: Artificial Sequence
<220> FEATURE:
<223> OTHER INFORMATION: Primer Ann-F2

<400> SEQUENCE: 36
ttgttacaag ctggagaact tctc                                              24

<210> SEQ ID NO 37
<211> LENGTH: 48
<212> TYPE: DNA
<213> ORGANISM: Artificial Sequence
<220> FEATURE:
<223> OTHER INFORMATION: Primer Ann-R2T7

<400> SEQUENCE: 37
ttaatacgac tcactatagg gagacttaac caacaacggc taataagg                    48

<210> SEQ ID NO 38
<211> LENGTH: 47
<212> TYPE: DNA
<213> ORGANISM: Artificial Sequence
<220> FEATURE:
<223> OTHER INFORMATION: Primer Betasp2-F1_T7

<400> SEQUENCE: 38
ttaatacgac tcactatagg gagaagatgt tggctgcatc tagagaa                     47

<210> SEQ ID NO 39
<211> LENGTH: 22
<212> TYPE: DNA
<213> ORGANISM: Artificial Sequence
<220> FEATURE:
<223> OTHER INFORMATION: Primer Betasp2-R1

<400> SEQUENCE: 39
gtccattcgt ccatccactg ca                                                22

<210> SEQ ID NO 40
<211> LENGTH: 23
<212> TYPE: DNA
<213> ORGANISM: Artificial Sequence
<220> FEATURE:
<223> OTHER INFORMATION: Primer Betasp2-F1

<400> SEQUENCE: 40
agatgttggc tgcatctaga gaa                                               23

<210> SEQ ID NO 41
<211> LENGTH: 46
<212> TYPE: DNA
<213> ORGANISM: Artificial Sequence
<220> FEATURE:
<223> OTHER INFORMATION: Primer Betasp2-R1_T7

<400> SEQUENCE: 41
ttaatacgac tcactatagg gagagtccat tcgtccatcc actgca                      46

<210> SEQ ID NO 42
<211> LENGTH: 46
<212> TYPE: DNA
<213> ORGANISM: Artificial Sequence
<220> FEATURE:
<223> OTHER INFORMATION: Primer Betasp2-F2_T7
```

<400> SEQUENCE: 42
ttaatacgac tcactatagg gagagcagat gaacaccagc gagaaa        46

<210> SEQ ID NO 43
<211> LENGTH: 22
<212> TYPE: DNA
<213> ORGANISM: Artificial Sequence
<220> FEATURE:
<223> OTHER INFORMATION: Primer Betasp2-R2

<400> SEQUENCE: 43
ctgggcagct tcttgtttcc tc        22

<210> SEQ ID NO 44
<211> LENGTH: 22
<212> TYPE: DNA
<213> ORGANISM: Artificial Sequence
<220> FEATURE:
<223> OTHER INFORMATION: Primer Betasp2-F2

<400> SEQUENCE: 44
gcagatgaac accagcgaga aa        22

<210> SEQ ID NO 45
<211> LENGTH: 46
<212> TYPE: DNA
<213> ORGANISM: Artificial Sequence
<220> FEATURE:
<223> OTHER INFORMATION: Primer Betasp2-R2_T7

<400> SEQUENCE: 45
ttaatacgac tcactatagg gagactgggc agcttcttgt ttcctc        46

<210> SEQ ID NO 46
<211> LENGTH: 51
<212> TYPE: DNA
<213> ORGANISM: Artificial Sequence
<220> FEATURE:
<223> OTHER INFORMATION: Primer L4-F1_T7

<400> SEQUENCE: 46
ttaatacgac tcactatagg gagaagtgaa atgttagcaa atataacatc c        51

<210> SEQ ID NO 47
<211> LENGTH: 26
<212> TYPE: DNA
<213> ORGANISM: Artificial Sequence
<220> FEATURE:
<223> OTHER INFORMATION: Primer L4-R1

<400> SEQUENCE: 47
acctctcact tcaaatcttg actttg        26

<210> SEQ ID NO 48
<211> LENGTH: 27
<212> TYPE: DNA
<213> ORGANISM: Artificial Sequence
<220> FEATURE:
<223> OTHER INFORMATION: Primer L4-F1

<400> SEQUENCE: 48
agtgaaatgt tagcaaatat aacatcc        27

<210> SEQ ID NO 49
<211> LENGTH: 50

<212> TYPE: DNA
<213> ORGANISM: Artificial Sequence
<220> FEATURE:
<223> OTHER INFORMATION: Primer L4-R1_T7

<400> SEQUENCE: 49
ttaatacgac tcactatagg gagaacctct cacttcaaat cttgactttg          50

<210> SEQ ID NO 50
<211> LENGTH: 50
<212> TYPE: DNA
<213> ORGANISM: Artificial Sequence
<220> FEATURE:
<223> OTHER INFORMATION: Primer L4-F2_T7

<400> SEQUENCE: 50
ttaatacgac tcactatagg gagacaaagt caagatttga agtgagaggt          50

<210> SEQ ID NO 51
<211> LENGTH: 25
<212> TYPE: DNA
<213> ORGANISM: Artificial Sequence
<220> FEATURE:
<223> OTHER INFORMATION: Primer L4-R2

<400> SEQUENCE: 51
ctacaaataa aacaagaagg acccc                                     25

<210> SEQ ID NO 52
<211> LENGTH: 26
<212> TYPE: DNA
<213> ORGANISM: Artificial Sequence
<220> FEATURE:
<223> OTHER INFORMATION: Primer L4-F2

<400> SEQUENCE: 52
caaagtcaag atttgaagtg agaggt                                    26

<210> SEQ ID NO 53
<211> LENGTH: 49
<212> TYPE: DNA
<213> ORGANISM: Artificial Sequence
<220> FEATURE:
<223> OTHER INFORMATION: Primer L4-R2_T7

<400> SEQUENCE: 53
ttaatacgac tcactatagg gagactacaa ataaacaag aaggacccc             49

<210> SEQ ID NO 54
<211> LENGTH: 1150
<212> TYPE: DNA
<213> ORGANISM: Zea mays

<400> SEQUENCE: 54
caacggggca gcactgcact gcactgcaac tgcgaatttc cgtcagcttg gagcggtcca    60
agcgccctgc gaagcaaact acgccgatgg cttcggcggc ggcgtgggag ggtccgacgg   120
ccgcggagct gaagacagcg ggggcggagg tgattcccgg cggcgtgcga gtgaaggggt   180
gggtcatcca gtcccacaaa ggccctatcc tcaacgccgc ctctctgcaa cgctttgaag   240
atgaacttca acaacacat ttacctgaga tggttttgg agagagtttc ttgtcacttc    300
aacatacaca aactggcatc aaatttcatt ttaatgcgct tgatgcactc aaggcatgga   360
agaaagaggc actgccacct gttgaggttc ctgctgcagc aaaatggaag ttcagaagta   420

```
agccttctga ccaggttata cttgactacg actatacatt tacgcacacca tattgtggga    480 gtgatgctgt ggttgtgaac tctggcactc cacaaacaag tttagatgga tgcggcactt    540
tgtgttggga ggatactaat gatcggattg acattgttgc cctttcagca aaagaaccca    600
ttctttccta cgacgaggtt atcttgtatg aagatgagtt agctgacaat ggtatctcat    660
ttcttactgt gcgagtgagg gtaatgccaa ctggttggtt tctgcttttg cgttttggc     720 ttagagttga tggtgtactg atgaggttga gagacactcg gttacattgc ctgtttggaa    780
acggcgacgg agccaagcca gtggtacttc gtgagtgctg ctggagggaa gcaacatttg    840
ctactttgtc tgcgaaagga tatccttcgg actctgcagc gtacgcggac ccgaaccta    900 ttgcccataa gcttcctatt gtgacgcaga agacccaaaa gctgaaaaat cctacctgac    960
tgacacaaag gcgccctacc gcgtgtacat catgactgtc ctgtcctatc gttgcctttt   1020
gtgtttgcca catgttgtgg atgtacgttt ctatgacgaa acaccatagt ccatttcgcc   1080
tgggccgaac agagatagct gattgtcatg tcacgtttga attagaccat tccttagccc   1140
ttttcccc                                                             1150

<210> SEQ ID NO 55
<211> LENGTH: 22
<212> TYPE: DNA
<213> ORGANISM: Artificial Sequence
<220> FEATURE:
<223> OTHER INFORMATION: Oligonucleotide T20VN
<220> FEATURE:
<221> NAME/KEY: misc_feature
<222> LOCATION: (22)..(22)
<223> OTHER INFORMATION: n is a, c, g, or t

<400> SEQUENCE: 55
tttttttttt ttttttttt vn                                                22

<210> SEQ ID NO 56
<211> LENGTH: 21
<212> TYPE: DNA
<213> ORGANISM: Artificial Sequence
<220> FEATURE:
<223> OTHER INFORMATION: Primer Fsh-2v1 (F)

<400> SEQUENCE: 56
gtggtcagaa gggttgtact t                                                21

<210> SEQ ID NO 57
<211> LENGTH: 21
<212> TYPE: DNA
<213> ORGANISM: Artificial Sequence
<220> FEATURE:
<223> OTHER INFORMATION: Primer Fsh-2v1 (R)

<400> SEQUENCE: 57
gagtatcgca ctcctcaaga c                                                21

<210> SEQ ID NO 58
<211> LENGTH: 21
<212> TYPE: DNA
<213> ORGANISM: Artificial Sequence
<220> FEATURE:
<223> OTHER INFORMATION: Primer TIPmxF

<400> SEQUENCE: 58
tgagggtaat gccaactggt t                                                21
```

<210> SEQ ID NO 59
<211> LENGTH: 24
<212> TYPE: DNA
<213> ORGANISM: Artificial Sequence
<220> FEATURE:
<223> OTHER INFORMATION: Primer TIPmxR

<400> SEQUENCE: 59
gcaatgtaac cgagtgtctc tcaa                                            24

<210> SEQ ID NO 60
<211> LENGTH: 32
<212> TYPE: DNA
<213> ORGANISM: Artificial Sequence
<220> FEATURE:
<223> OTHER INFORMATION: Probe HXTIP

<400> SEQUENCE: 60
tttttggctt agagttgatg gtgtactgat ga                                   32

<210> SEQ ID NO 61
<211> LENGTH: 151
<212> TYPE: DNA
<213> ORGANISM: Escherichia coli

<400> SEQUENCE: 61
gaccgtaagg cttgatgaaa caacgcggcg agctttgatc aacgaccttt tggaaacttc     60
ggcttcccct ggagagagcg agattctccg cgctgtagaa gtcaccattg ttgtgcacga    120
cgacatcatt ccgtggcgtt atccagctaa g                                   151

<210> SEQ ID NO 62
<211> LENGTH: 69
<212> TYPE: DNA
<213> ORGANISM: Artificial Sequence
<220> FEATURE:
<223> OTHER INFORMATION: Partial AAD1 coding region

<400> SEQUENCE: 62
tgttcggttc cctctaccaa gcacagaacc gtcgcttcag caacacctca gtcaaggtga     60
tggatgttg                                                             69

<210> SEQ ID NO 63
<211> LENGTH: 4233
<212> TYPE: DNA
<213> ORGANISM: Zea mays

<400> SEQUENCE: 63
agcctggtgt tccggagga gacagacatg atccctgccg ttgctgatcc gacgacgctg      60
gacggcgggg gcgcgcgcag gccgttgctc ccggagacgg accctcgggg gcgtgctgcc    120
gccggcgccg agcagaagcg gccgccggct acgccgaccg ttctcaccgc cgtcgtctcc    180
gccgtgctcc tgctcgtcct cgtggcggtc acagtcctcg cgtcgcagca cgtcgacggg    240
caggctgggg gcgttcccgc gggcgaagat gccgtcgtcg tcgaggtggc cgcctcccgt    300
ggcgtggctg agggcgtgtc ggagaagtcc acgccccgc tcctcggctc cggcgcgctc    360
caggacttct cctggaccaa cgcgatgctg gcgtggcagc gcacggcgtt ccacttccag    420 cccccccaaga actggatgaa cggttagttg acccgtcgc catcggtgac gacgcgcgga    480
tcgttttttt cttttttcct ctcgttctgg ctctaacttg gttccgcgtt tctgtcacgg    540
acgcctcgtg cacatggcga taccgatacc gccggccgcg tatatctatc tacctcgacc    600

```
ggcttctcca gatccgaacg gtaagttgtt ggctccgata cgatcgatca catgtgagct    660
cggcatgctg cttttctgcg cgtgcatgcg gctcctagca ttccacgtcc acgggtcgtg    720
acatcaatgc acgatataat cgtatcggta cagagatatt gtcccatcag ctgctagctt    780
tcgcgtattg atgtcgtgac attttgcacg caggtccgct gtatcacaag ggctggtacc    840
acctcttcta ccagtggaac ccggactccg cggtatgggg caacatcacc tggggccacg    900
ccgtctcgcg cgacctcctc cactggctgc acctaccgct ggccatggtg cccgatcacc    960
cgtacgacgc caacggcgtc tggtccgggt cggcgacgcg cctgcccgac ggccggatcg   1020
tcatgctcta cacgggctcc acggcggagt cgtcggcgca ggtgcagaac ctcgcggagc   1080
cggccgacgc gtccgacccg ctgctgcggg agtgggtcaa gtcggacgcc aacccggtgc   1140
tggtgccgcc gccgggcatc gggccgacgg acttccgcga cccgacgacg cgtgtcgga    1200
cgccggccgg caacgacacg gcgtggcggg tcgccatcgg gtccaaggac cgggaccacg   1260
cggggctggc gctggtgtac cggacggagg acttcgtgcg gtacgacccg cgcccggcgc   1320
tgatgcacgc cgtgccgggc accggcatgt gggagtgcgt ggacttctac ccggtggccg   1380
cgggatcagg cgccgcggcg ggcagcgggg acgggctgga gacgtccgcg gcgccgggac   1440
ccggggtgaa gcacgtgctc aaggctagcc tcgacgacga caagcacgac tactacgcga   1500
tcggcaccta cgaccggcg acggacacct ggaccccccga cagcgcggag gacgacgtcg   1560
ggatcggcct ccggtacgac tatggcaagt actacgcgtc gaagaccttc tacgaccccg   1620
tccttcgccg gcgggtgctc tgggggtggg tcggcgagac cgacagcgag cgcgcggaca   1680
tcctcaaggg ctgggcatcc gtgcaggtac gtctcagggt ttgaggctag catggcttca   1740
atcttgctgg catcgaatca ttaatgggca gatattataa cttgataatc tgggttggtt   1800
gtgtgtggtg gggatggtga cacacgcgcg gtaataatgt agctaagctg gttaaggatg   1860
agtaatgggg ttgcgtataa acgacagctc tgctaccatt acttctgaca cccgattgaa   1920
ggagacaaca gtaggggtag ccggtagggt tcgtcgactt gccttttctt ttttcctttg   1980
ttttgttgtg gatcgtccaa cacaaggaaa ataggatcat ccaacaaaca tggaagtaat   2040
cccgtaaaac atttctcaag gaaccatcta gctagacgag cgtggcatga tccatgcatg   2100
cacaaacact agataggtct ctgcagctgt gatgttcctt tacatatacc accgtccaaa   2160
ctgaatccgg tctgaaaatt gttcaagcag agaggcccg atcctcacac ctgtacacgt   2220
ccctgtacgc gccgtcgtgg tctcccgtga tcctgccccg tccctccac gcggccacgc   2280
ctgctgcagc gctctgtaca agcgtgcacc acgtgagaat ttccgtctac tcgagcctag   2340
tagttagacg ggaaaacgag aggaagcgca cggtccaagc acaacacttt gcgcgggccc   2400
gtgacttgtc tccggttggc tgagggcgcg cgacagagat gtatggcgcc gcggcgtgtc   2460
ttgtgtcttg tcttgcctat acaccgtagt cagagactgt gtcaaagccg tccaacgaca   2520
atgagctagg aaacggggttg gagagctggg ttcttgcctt gcctcctgtg atgtctttgc   2580
cttgcatagg gggcgcagta tgtagctttg cgttttactt cacgccaaag gatactgctg   2640
atcgtgaatt attattatta tatatatatc gaatatcgat ttcgtcgctc tcgtggggtt   2700
ttatttccca gactcaaact tttcaaaagg cctgtgtttt agttcttttc ttccaattga   2760
gtaggcaagg cgtgtgagtg tgaccaacgc atgcatggat atcgtggtag actggtagag   2820
ctgtcgttac cagcgcgatg cttgtatatg tttgcagtat tttcaaatga atgtctcagc   2880
tagcgtacag ttgaccaagt cgacgtggag ggcgcacaac agacctctga cattattcac   2940
tttttttta ccatgccgtg cacgtgcagt caatcccag gacggtcctc ctggacacga   3000
```

```
agacgggcag caacctgctc cagtggccgg tggtggaggt ggagaacctc cggatgagcg    3060
gcaagagctt cgacggcgtc gcgctggacc gcggatccgt cgtgcccctc gacgtcggca    3120
aggcgacgca ggtgacgccg cacgcagcct gctgcagcga acgaactcgc gcgttgccgg    3180
cccgcggcca gctgacttag tttctctggc tgatcgaccg tgtgcctgcg tgcgtgcagt    3240
tggacatcga ggctgtgttc gaggtggacg cgtcggacgc ggcgggcgtc acggaggccg    3300
acgtgacgtt caactgcagc accagcgcag gcgcggcggg ccggggcctg ctcggcccgt    3360
tcggccttct cgtgctggcg gacgacgact tgtccgagca gaccgccgtg tacttctacc    3420
tgctcaaggg cacggacggc agcctccaaa ctttcttctg ccaagacgag ctcaggtatg    3480
tatgttatga cttatgacca tgcatgcatg cgcatttctt agctaggctg tgaagcttct    3540
tgttgagttg tttcacagat gcttaccgtc tgctttgttt cgtatttcga ctaggcatcc    3600
aaggcgaacg atctggttaa gagagtatac gggagcttgg tccctgtgct agatggggag    3660
aatctctcgg tcagaatact ggtaagtttt tacagcgcca gccatgcatg tgttggccag    3720
ccagctgctg gtactttgga cactcgttct tctcgcactg ctcattattg cttctgatct    3780
ggatgcacta caaattgaag gttgaccact ccatcgtgga gagctttgct caaggcggga    3840
ggacgtgcat cacgtcgcga gtgtacccca cacgagccat ctacgactcc gcccgcgtct    3900
tcctcttcaa caacgccaca catgctcacg tcaaagcaaa atccgtcaag atctggcagc    3960
tcaactccgc ctacatccgg ccatatccgg caacgacgac ttctctatga ctaaattaag    4020
tgacggacag ataggcgata ttgcatactt gcatcatgaa ctcatttgta caacagtgat    4080
tgtttaattt atttgctgcc ttccttatcc ttcttgtgaa actatatggt acacacatgt    4140
atcattaggt ctagtagtgt tgttgcaaag acacttagac accagaggtt ccaggagtat    4200
cagagataag gtataagagg gagcagggag cag                                4233

<210> SEQ ID NO 64
<211> LENGTH: 20
<212> TYPE: DNA
<213> ORGANISM: Artificial Sequence
<220> FEATURE:
<223> OTHER INFORMATION: Primer GAAD1-F

<400> SEQUENCE: 64
tgttcggttc cctctaccaa                                                20

<210> SEQ ID NO 65
<211> LENGTH: 22
<212> TYPE: DNA
<213> ORGANISM: Artificial Sequence
<220> FEATURE:
<223> OTHER INFORMATION: Primer GAAD1-R

<400> SEQUENCE: 65
caacatccat caccttgact ga                                             22

<210> SEQ ID NO 66
<211> LENGTH: 24
<212> TYPE: DNA
<213> ORGANISM: Artificial Sequence
<220> FEATURE:
<223> OTHER INFORMATION: Probe GAAD1-P (FAM)

<400> SEQUENCE: 66
cacagaaccg tcgcttcagc aaca                                           24
```

<210> SEQ ID NO 67
<211> LENGTH: 18
<212> TYPE: DNA
<213> ORGANISM: Artificial Sequence
<220> FEATURE:
<223> OTHER INFORMATION: Primer IVR1-F

<400> SEQUENCE: 67
tggcggacga cgacttgt                                            18

<210> SEQ ID NO 68
<211> LENGTH: 19
<212> TYPE: DNA
<213> ORGANISM: Artificial Sequence
<220> FEATURE:
<223> OTHER INFORMATION: Primer IVR1-R

<400> SEQUENCE: 68
aaagtttgga ggctgccgt                                           19

<210> SEQ ID NO 69
<211> LENGTH: 26
<212> TYPE: DNA
<213> ORGANISM: Artificial Sequence
<220> FEATURE:
<223> OTHER INFORMATION: Probe IVR1-P (HEX)

<400> SEQUENCE: 69
cgagcagacc gccgtgtact tctacc                                   26

<210> SEQ ID NO 70
<211> LENGTH: 19
<212> TYPE: DNA
<213> ORGANISM: Artificial Sequence
<220> FEATURE:
<223> OTHER INFORMATION: Primer SPC1A

<400> SEQUENCE: 70
cttagctgga taacgccac                                           19

<210> SEQ ID NO 71
<211> LENGTH: 19
<212> TYPE: DNA
<213> ORGANISM: Artificial Sequence
<220> FEATURE:
<223> OTHER INFORMATION: Primer SPC1S

<400> SEQUENCE: 71
gaccgtaagg cttgatgaa                                           19

<210> SEQ ID NO 72
<211> LENGTH: 21
<212> TYPE: DNA
<213> ORGANISM: Artificial Sequence
<220> FEATURE:
<223> OTHER INFORMATION: Probe TQSPEC (CY5*)

<400> SEQUENCE: 72
cgagattctc cgcgctgtag a                                        21

<210> SEQ ID NO 73
<211> LENGTH: 20
<212> TYPE: DNA
<213> ORGANISM: Artificial Sequence
<220> FEATURE:
<223> OTHER INFORMATION: Primer Loop-F

<400> SEQUENCE: 73
ggaacgagct gcttgcgtat                                              20

<210> SEQ ID NO 74
<211> LENGTH: 20
<212> TYPE: DNA
<213> ORGANISM: Artificial Sequence
<220> FEATURE:
<223> OTHER INFORMATION: Primer Loop-R

<400> SEQUENCE: 74
cacggtgcag ctgattgatg                                              20

<210> SEQ ID NO 75
<211> LENGTH: 18
<212> TYPE: DNA
<213> ORGANISM: Artificial Sequence
<220> FEATURE:
<223> OTHER INFORMATION: Probe Loop-P (FAM)

<400> SEQUENCE: 75
tcccttccgt agtcagag                                                18

<210> SEQ ID NO 76
<211> LENGTH: 805
<212> TYPE: DNA
<213> ORGANISM: Euschistus heros

<400> SEQUENCE: 76
agaatacaaa acagcaactg aatttgctgc tgatgtgaga ctaattttta caaattgtta    60
caagtataat cccccggacc atgatgttgt tgcaatgggc cgaaaattgc aggatgtttt   120
tgaagtgagt taagaatcat gcaggaagag atgagaaaac tcgtcgaaga aggaactgtt   180
aaaaagaaga agaaaaagaa agaaggttca ggttctggtg aagttcttc tagtaagaaa    240 cggaaatctg ctgataggac attaggtaaa acagccgatg gtgggcttat agctggtgcc   300
ggagcacccg ctatcatgga aataaaggct actgatggcg taaaggctgt ccctcctcca   360
ggcaggaatg cagtcccttc accccaggtc aaaccaaaca agggcaaagc ccctggaagg   420
gcaccaggaa aaaccaattc tcagggtaag aggccaaagc cgaactccag gtctactaac   480
tctaagaaga gaatcctgt tgtcacttca gagtttaact cggaagatga ggataatgca    540
aagcctatgt cttatgatga aaagagacaa cttagcttgg atattaacaa gctaccaggt   600
gataaacttg gaagagtagt ccatatcatt caggccagag agccctcttt gagggattca   660
aaccctgatg aaattgaaat agactttgag acattgaagc catcaaccct gagggagctc   720
gagtcctacg ttgcatcatg tctcaggaaa aagccacata agaaaaatgt atcagacaaa   780
aatcaaaaag atgaagcgat ggccg                                        805

<210> SEQ ID NO 77
<211> LENGTH: 227
<212> TYPE: PRT
<213> ORGANISM: Euschistus heros

<400> SEQUENCE: 77

Ser Glu Leu Arg Ile Met Gln Glu Glu Met Arg Lys Leu Val Glu Glu
1               5                   10                  15

Gly Thr Val Lys Lys Lys Lys Lys Lys Glu Gly Ser Gly Ser Gly
            20                  25                  30

```
Gly Ser Ser Ser Ser Lys Lys Arg Lys Ser Ala Asp Arg Thr Leu Gly
            35                  40                  45
Lys Thr Ala Asp Gly Gly Leu Ile Ala Gly Ala Gly Ala Pro Ala Ile
 50                  55                  60
Met Glu Ile Lys Ala Thr Asp Gly Val Lys Ala Val Pro Pro Gly
 65                  70                  75                  80
Arg Asn Ala Val Pro Ser Pro Gln Val Lys Pro Asn Lys Gly Lys Ala
                85                  90                  95
Pro Gly Arg Ala Pro Gly Lys Thr Asn Ser Gln Gly Lys Arg Pro Lys
            100                 105                 110
Pro Asn Ser Arg Ser Thr Asn Ser Lys Lys Asn Pro Val Val Thr
            115                 120                 125
Ser Glu Phe Asn Ser Glu Asp Glu Asn Ala Lys Pro Met Ser Tyr
130                 135                 140
Asp Glu Lys Arg Gln Leu Ser Leu Asp Ile Asn Lys Leu Pro Gly Asp
145                 150                 155                 160
Lys Leu Gly Arg Val Val His Ile Ile Gln Ala Arg Glu Pro Ser Leu
                165                 170                 175
Arg Asp Ser Asn Pro Asp Glu Ile Glu Ile Asp Phe Glu Thr Leu Lys
            180                 185                 190
Pro Ser Thr Leu Arg Glu Leu Glu Ser Tyr Val Ala Ser Cys Leu Arg
            195                 200                 205
Lys Lys Pro His Lys Lys Asn Val Ser Asp Lys Asn Gln Lys Asp Glu
            210                 215                 220
Ala Met Ala
225

<210> SEQ ID NO 78
<211> LENGTH: 4607
<212> TYPE: DNA
<213> ORGANISM: Euschistus heros

<400> SEQUENCE: 78
tgtaaatgtt cccatccatt atttcggtat attgatgtat accgttttag gctcagcctt      60
attggcttct tcccgagtgg ggagcccgcc atgttgacca actaagcgcc aaaagaggag     120
cttttttggt attttttctc tttgtttagg taaaaaaata gttaagtatt gttaaattga     180
tgttagggtt acgttacgaa tgatcttgaa gtggtgatgt ggttactccc cctttcgagt     240
acagtagctt aaccaagctt gtgttgggct tgagcttctc tcgtcttctg tagctttact     300
ttacgtttat tactggataa agtgaaaaat aagtgttaaa tacaagtgtg tggactccag     360
gaagggattt tgtgctaaat gaaatagttt tttgtttaat aacagtgatt ttggatcgtt     420
tttaaaggta gtgtgaaatg cggtttgtta ttctcaggag tatccccgag ccacatcca      480
aaattcaatt ttttcttca agtttcccc ttgaaggttc tgttatgact aatatactca      540
agtaaattgt tatcttgttg ttccttaaat taggactaat gatatgggga gtagttttaa     600
ctaagcattt ctgtatgcca tttttatgag taaagcaatg taaggttatt gagatttaaa     660
tgttcctgta agatcatgat ttcatcttat tgtcttactc agatgcgtct gcattgggct     720
ttttttacagt actaatgaaa acctcagtga caatcgatcc ttggaaagga gtgtggccaa     780
aatgcaacaa atggactcct tgcaacctaa caacgcaaca ggactggtga aaagcggact     840
agaggcgggg gccggtagcg gcatgaagga gccccgcca cgagaggagc cggtcctaga     900
cccaatcaat ggtgttgtcc agcctccggt catacctcct ccccacaggc ctggccgagt     960
```

```
aaccaaccaa ttgcaatata ttcagaaaaa tgtccttaaa gcagtctgga aacatcaata    1020
tgcttggcct ctacagcaac ctgtcgatgc taataaactc aatcttcctg attaccataa    1080
agttattaaa catccaatgg atcttggtac tatcaaaaaa cgactggaaa acaattatta    1140
ttggtgtggt gctgagtgta ttcaagattt caacacaatg tttaacaatt gttatgttta    1200
taacaaacca ggagaagatg ttgttgttat ggctcaaacg ctggaaaaac tttatttgca    1260
aaagctggaa acaatgccca aagaggaaat tgagcttgag cctccaccac ctaaaggttc    1320
taagccagtt aagaagcgac tggagttat aggtccaggt agaggggcg ggaccactgg    1380
```

```
tgccactggt actattgtaa ataaaaatgc tggggctcca cagcccgtag taccgttagc   3420
aagcaccaac aaacctactg tacctccggt ctctgcagtg acacagcctg aacctgtgaa   3480
acctgttgta gcatcacata gcttgcctcc ccaacctgcg aggcctaccg caacggctgc   3540
ccctctgaca actgctaaga gggcgtcaat ccccacgcca gcgacatcga tgggcatacc   3600
tccgcctgct ccgactggtc ttgaaacagg tcctattgag atcaaacagg aattggatgt   3660
tcctgttcca ctagcacccg ttccagatca tttggatttc aaaaacccttt tggaggtgaa   3720 gcccgagcta atgatatcg ttactgggat gccttctgta tttgatcctt tgcctgactc   3780
acctcccatc attaaggaag aaaagcatcc tatactcccc catcacacag atggacactt   3840
gaacaattct cttcccccctg tcagcaacgt acctggtccg ccaatcatac cgagtgctgc   3900
acttccaact acaccacatc acttagatat gaataagaat tcccagcctc ctcagcttcc   3960
ccagacgcca actttacaac accccttcaa acctaagaat tttggcttca acattgatgg   4020
ctgcttaagg atttcaaaga ctgttgagca gaacttgaaa aatgccagtt catggtcttc   4080
acttgcccag tccccaacac cagctctcac cccaactcca ccgactgcgg ctctgaagtc   4140
ctccatggct gacagctttc aagcttttaa gaaacaagct aaagaaaatg ccaagaagca   4200
acgagccctg attgaacagc aagaaatgag gcgacatcaa aaagaacagg ctgaaaggga   4260
aagattacgt gttgaaaccg aaaagaggag agaaagagaa gaagaagaag ctctggagaa   4320
ggctagaaat agttatgtcg ggaacaggaa ggctgctgta gtggcttctg gaagagttga   4380
agaggttaaa aatgctgcta tcgaggaagg taccagccca ggttcggcag acaaagctgc   4440
tgcagagcga gaacgtctaa ggcaacgaga gcaagagagg cggcgaagag aagcattggc   4500
tgggcaaatt gatatgaaca ggcaaagtga tttaatggct gcttttgaac agaccttgta   4560
attcttcaag ggcagttttt gtgttttctt ttctttcttt tttttaa              4607
```

<210> SEQ ID NO 79
<211> LENGTH: 1262
<212> TYPE: PRT
<213> ORGANISM: Euschistus heros

<400> SEQUENCE: 79

```
Val Ala Lys Met Gln Gln Met Asp Ser Leu Gln Pro Asn Asn Ala Thr
1               5                   10                  15

Gly Leu Val Lys Ser Gly Leu Glu Ala Gly Ala Gly Ser Gly Met Lys
            20                  25                  30

Glu Pro Pro Pro Arg Glu Glu Pro Val Leu Asp Pro Ile Asn Gly Val
        35                  40                  45

Val Gln Pro Pro Val Ile Pro Pro His Arg Pro Gly Arg Val Thr
    50                  55                  60

Asn Gln Leu Gln Tyr Ile Gln Lys Asn Val Leu Lys Ala Val Trp Lys
65                  70                  75                  80

His Gln Tyr Ala Trp Pro Leu Gln Gln Pro Val Asp Ala Asn Lys Leu
                85                  90                  95

Asn Leu Pro Asp Tyr His Lys Val Ile Lys His Pro Met Asp Leu Gly
            100                 105                 110

Thr Ile Lys Lys Arg Leu Glu Asn Tyr Tyr Trp Cys Gly Ala Glu
        115                 120                 125

Cys Ile Gln Asp Phe Asn Thr Met Phe Asn Asn Cys Tyr Val Tyr Asn
    130                 135                 140

Lys Pro Gly Glu Asp Val Val Val Met Ala Gln Thr Leu Glu Lys Leu
```

```
            145                 150                 155                 160

Tyr Leu Gln Lys Leu Glu Thr Met Pro Lys Glu Glu Ile Glu Leu Glu
                        165                 170                 175

Pro Pro Pro Pro Lys Gly Ser Lys Pro Val Lys Lys Arg Pro Gly Val
                        180                 185                 190

Ile Gly Pro Gly Arg Gly Gly Thr Thr Gly Ala Gly Arg Gly Arg
                        195                 200                 205

Pro Ser Asn Ser Thr Pro Ala Ala Ala Val Val Thr Thr Pro Val
        210                 215                 220

Pro Pro Val Thr Pro Ser His Leu Pro Ala Thr Ile Pro Gly Ser
        225                 230                 235                 240

Thr Ala Thr Thr Thr Val Pro Thr Thr His His Asn Ser Leu Pro Pro
                        245                 250                 255

Gln Val Gly Gln Pro Ala Ala Val Pro Ser Asn Phe Ser Thr Thr Thr
                        260                 265                 270

Val Asp Pro Leu Leu Thr Pro Gly Leu Ala Pro Gly Val Gly Pro Lys
                        275                 280                 285

Gly Gly Lys Gly Ala Val Val Gln Thr Pro Thr Ala Pro Lys Pro Lys
                        290                 295                 300

Lys Gly Val Lys Arg Lys Ala Asp Leu Ala Asn Asp Ser Pro Ala Ser
        305                 310                 315                 320

Phe Asp Pro Thr Tyr Thr Pro Gly Asp Ser Lys Ala Ala Lys Val Gly
                        325                 330                 335

Thr Arg Arg Glu Ser Gly Arg Gln Ile Lys Lys Pro Gln Arg Gln Ser
                        340                 345                 350

Asp Asp Gly Met Pro Phe Ser Gln Ser Pro Met Ala Pro Tyr Ser Leu
                        355                 360                 365

Ser Asn Ser Thr Gln Ala Ala His Glu Lys Pro Lys Glu Lys Leu Ser
                        370                 375                 380

Glu Thr Leu Lys Ala Cys Asn Glu Ile Leu Lys Glu Leu Phe Ser Lys
        385                 390                 395                 400

Lys His Phe Asn Tyr Ala Trp Pro Phe Tyr Lys Pro Val Asp Ala Glu
                        405                 410                 415

Trp Leu Gly Leu His Asp Tyr His Asp Ile Ile Lys Lys Pro Met Asp
                        420                 425                 430

Leu Gly Thr Val Lys Gln Lys Met Asp Asn Arg Glu Tyr Lys Thr Ala
                        435                 440                 445

Thr Glu Phe Ala Ala Asp Val Arg Leu Ile Phe Thr Asn Cys Tyr Lys
        450                 455                 460

Tyr Asn Pro Pro Asp His Asp Val Val Ala Met Gly Arg Lys Leu Gln
        465                 470                 475                 480

Asp Val Phe Glu Val Arg Phe Ala Gln Val Pro Glu Asp Ser Pro Ile
                        485                 490                 495

Ser Thr Val Pro Glu Lys Glu Glu Ser Thr Ser Gly Ser Ser Ser
                        500                 505                 510

Gly Ser Glu Ser Glu Thr Asp Asn Ser Asp Asp Glu Arg Ala Arg Lys
                        515                 520                 525

Leu Ser Gln Leu Gln Glu Gln Leu Arg Ile Met Gln Glu Glu Met Arg
                        530                 535                 540

Lys Leu Val Glu Glu Gly Thr Val Lys Lys Lys Lys Lys Lys Glu
        545                 550                 555                 560

Gly Ser Gly Ser Gly Gly Ser Ser Ser Ser Lys Lys Arg Lys Ser Ala
                        565                 570                 575
```

```
Asp Arg Thr Leu Gly Lys Thr Ala Asp Gly Leu Ile Ala Gly Ala
            580                 585                 590

Gly Ala Pro Ala Ile Met Glu Ile Lys Ala Thr Asp Gly Val Lys Ala
        595                 600                 605

Val Pro Pro Gly Arg Asn Ala Val Pro Ser Pro Gln Val Lys Pro
    610                 615                 620

Asn Lys Gly Lys Ala Pro Gly Arg Ala Pro Gly Lys Thr Asn Ser Gln
625                 630                 635                 640

Gly Lys Arg Pro Lys Pro Asn Ser Arg Ser Thr Asn Ser Lys Lys Lys
                645                 650                 655

Asn Pro Val Val Thr Ser Glu Phe Asn Ser Glu Asp Glu Asn Ala
            660                 665                 670

Lys Pro Met Ser Tyr Asp Glu Lys Arg Gln Leu Ser Leu Asp Ile Asn
        675                 680                 685

Lys Leu Pro Gly Asp Lys Leu Gly Arg Val Val His Ile Ile Gln Ala
    690                 695                 700

Arg Glu Pro Ser Leu Arg Asp Ser Asn Pro Asp Glu Ile Glu Ile Asp
705                 710                 715                 720

Phe Glu Thr Leu Lys Pro Ser Thr Leu Arg Glu Leu Glu Ser Tyr Val
                725                 730                 735

Ala Ser Cys Leu Arg Lys Lys Pro Arg Lys Pro Tyr Asn Lys Lys Asn
            740                 745                 750

Val Ser Ala Lys Ser Lys Asp Glu Ala Met Ala Glu Lys Lys Gln Glu
        755                 760                 765

Leu Glu Lys Arg Leu Gln Asp Val Thr Gly Gln Leu Gly Gly Ser Ala
    770                 775                 780

Lys Lys Thr Ala Lys Lys Gln Gly Gln Gly Arg Leu Ser Ala Ser Ser
785                 790                 795                 800

Ser Ser Ser Ser Asp Ser Asp Thr Ser Ser Ser Ser Leu Ser Ser Ser
                805                 810                 815

Ser Ser Asp Ser Ser Asp Ser Glu Ala Gly Lys Ala Gly Arg Pro Pro
            820                 825                 830

Arg Lys Lys Asn Lys Lys Asn His Gln Ile Ala Thr Thr Ala Ala Thr
        835                 840                 845

Thr Val Gln Gln Asn Gln Thr Val Pro Ser Leu Thr Met Thr Thr Ala
    850                 855                 860

Thr Gly Thr Ile Val Asn Lys Asn Ala Gly Ala Pro Gln Pro Val Val
865                 870                 875                 880

Pro Leu Ala Ser Thr Asn Lys Pro Thr Val Pro Val Ser Ala Val
                885                 890                 895

Thr Gln Pro Glu Pro Val Lys Pro Val Val Ala Ser His Ser Leu Pro
            900                 905                 910

Pro Gln Pro Ala Arg Pro Thr Ala Thr Ala Ala Pro Leu Thr Thr Ala
        915                 920                 925

Lys Arg Ala Ser Ile Pro Thr Pro Ala Thr Ser Met Gly Ile Pro Pro
    930                 935                 940

Pro Ala Pro Thr Gly Leu Glu Thr Gly Pro Ile Glu Ile Lys Gln Glu
945                 950                 955                 960

Leu Asp Val Pro Val Pro Leu Ala Pro Val Pro Asp His Leu Asp Phe
                965                 970                 975

Lys Asn Leu Leu Glu Val Lys Pro Glu Leu Asn Asp Ile Val Thr Gly
            980                 985                 990
```

Met Pro Ser Val Phe Asp Pro Leu Pro Asp Ser Pro Pro Ile Ile Lys
995                 1000                1005

Glu Glu Lys His Pro Ile Leu Pro His Thr Asp Gly His Leu
1010                1015                1020

Asn Asn Ser Leu Pro Pro Val Ser Asn Val Pro Gly Pro Pro Ile
1025                1030                1035

Ile Pro Ser Ala Ala Leu Pro Thr Thr Pro His His Leu Asp Met
1040                1045                1050

Asn Lys Asn Ser Gln Pro Pro Gln Leu Pro Gln Thr Pro Thr Leu
1055                1060                1065

Gln His Pro Phe Lys Pro Lys Asn Phe Gly Phe Asn Ile Asp Gly
1070                1075                1080

Cys Leu Arg Ile Ser Lys Thr Val Glu Gln Asn Leu Lys Asn Ala
1085                1090                1095

Ser Ser Trp Ser Ser Leu Ala Gln Ser Pro Thr Pro Ala Leu Thr
1100                1105                1110

Pro Thr Pro Pro Thr Ala Ala Leu Lys Ser Ser Met Ala Asp Ser
1115                1120                1125

Phe Gln Ala Phe Lys Lys Gln Ala Lys Glu Asn Ala Lys Lys Gln
1130                1135                1140

Arg Ala Leu Ile Glu Gln Gln Glu Met Arg Arg His Gln Lys Glu
1145                1150                1155

Gln Ala Glu Arg Glu Arg Leu Arg Val Glu Thr Glu Lys Arg Arg
1160                1165                1170

Glu Arg Glu Glu Glu Ala Leu Glu Lys Ala Arg Asn Ser Tyr
1175                1180                1185

Val Gly Asn Arg Lys Ala Ala Val Val Ala Ser Gly Arg Val Glu
1190                1195                1200

Glu Val Lys Asn Ala Ala Ile Glu Glu Gly Thr Ser Pro Gly Ser
1205                1210                1215

Ala Asp Lys Ala Ala Ala Glu Arg Glu Arg Leu Arg Gln Arg Glu
1220                1225                1230

Gln Glu Arg Arg Arg Arg Glu Ala Leu Ala Gly Gln Ile Asp Met
1235                1240                1245

Asn Arg Gln Ser Asp Leu Met Ala Ala Phe Glu Gln Thr Leu
1250                1255                1260

<210> SEQ ID NO 80
<211> LENGTH: 367
<212> TYPE: DNA
<213> ORGANISM: Euschistus heros

<400> SEQUENCE: 80
gcccctggaa gggcaccagg aaaaaccaat tctcagggta agaggccaaa gccgaactcc    60
aggtctacta actctaagaa gaagaatcct gttgtcactt cagagtttaa ctcggaagat   120
gaggataatg caaagcctat gtcttatgat gaaaagagac aacttagctt ggatattaac   180
aagctaccag gtgataaact tggaagagta gtccatatca ttcaggccag agagccctct   240
ttgagggatt caaccctga tgaaattgaa atagactttg agacattgaa gccatcaacc   300
ctgagggagc tcgagtccta cgttgcatca tgtctcagga aaaagccaca taagaaaaat   360
gtatcag                                                             367

<210> SEQ ID NO 81
<211> LENGTH: 164

```
<212> TYPE: DNA
<213> ORGANISM: Euschistus heros

<400> SEQUENCE: 81
acttcctcgc catagcaacc acatcgtggt cagaagggtt gtacttgtaa caattactaa      60
aaatcagtct aacgtcggcg gcaaagtctt gaggagtgcg atactctcgg ttttccattt     120
tattttttac agtactaaaa tccatcggtt tctttatgat gtcg                     164

<210> SEQ ID NO 82
<211> LENGTH: 56
<212> TYPE: DNA
<213> ORGANISM: Artificial Sequence
<220> FEATURE:
<223> OTHER INFORMATION: Primer BSB_fsh-1_For

<400> SEQUENCE: 82
ttaatacgac tcactatagg gagagccccct ggaagggcac caggaaaaac caattc         56

<210> SEQ ID NO 83
<211> LENGTH: 58
<212> TYPE: DNA
<213> ORGANISM: Artificial Sequence
<220> FEATURE:
<223> OTHER INFORMATION: Primer BSB_fsh-1_Rev

<400> SEQUENCE: 83
ttaatacgac tcactatagg gagactgata cattttcctt atgtggcttt ttcctgag       58

<210> SEQ ID NO 84
<211> LENGTH: 53
<212> TYPE: DNA
<213> ORGANISM: Artificial Sequence
<220> FEATURE:
<223> OTHER INFORMATION: Primer BSB_fsh-2_For

<400> SEQUENCE: 84
ttaatacgac tcactatagg gagaacagtc agacgatggt atgccatttt ctc             53

<210> SEQ ID NO 85
<211> LENGTH: 54
<212> TYPE: DNA
<213> ORGANISM: Artificial Sequence
<220> FEATURE:
<223> OTHER INFORMATION: Primer BSB_fsh-2_Rev

<400> SEQUENCE: 85
ttaatacgac tcactatagg gagagtcttc aggtacttga gcgaatctca cttc            54

<210> SEQ ID NO 86
<211> LENGTH: 301
<212> TYPE: DNA
<213> ORGANISM: Artificial Sequence
<220> FEATURE:
<223> OTHER INFORMATION: Sense strand of YFPv2 dsRNA

<400> SEQUENCE: 86
catctggagc acttctcttt catgggaaga ttccttacgt tgtggagatg gaagggaatg      60
ttgatggcca cacctttagc atacgtggga aaggctacgg agatgcctca gtgggaaagg    120
ttgatgcaca gttcatctgc acaactggtg atgttcctgt gccttggagc acacttgtca    180
ccactctcac ctatggagca cagtgctttg ccaagtatgg tccagagttg aaggacttct    240
acaagtcctg tatgccagat ggctatgtgc aagagcgcac aatcaccttt gaaggagatg    300
```

<210> SEQ ID NO 87
<211> LENGTH: 47
<212> TYPE: DNA
<213> ORGANISM: Artificial Sequence
<220> FEATURE:
<223> OTHER INFORMATION: Primer YFPv2-F

<400> SEQUENCE: 87
ttaatacgac tcactatagg gagagcatct ggagcacttc tctttca         47

<210> SEQ ID NO 88
<211> LENGTH: 46
<212> TYPE: DNA
<213> ORGANISM: Artificial Sequence
<220> FEATURE:
<223> OTHER INFORMATION: Primer YFPv2-R

<400> SEQUENCE: 88
ttaatacgac tcactatagg gagaccatct ccttcaaagg tgattg          46

<210> SEQ ID NO 89
<211> LENGTH: 4901
<212> TYPE: RNA
<213> ORGANISM: Diabrotica virgifera

<400> SEQUENCE: 89
cguaugucgg cgaugugcgc gaaaaucauu ucuucacuu uucucauga uuuuuauaua       60
auugguggaaa aucauaauuu cgccauauua ugcaacauuu uuuguuuuug aauaaagugc   120
aaggcucuca cacgucccgcc aucacgacag uuuguggcaa gcuuggccag cggguaugug   180
uuaggugagu gagaguggug uagcuccgua uuuuucacga uucuaaugug gauuaucacu   240
caaaagacgc agauccaagc uaugauggcu uuuaucuacu aagaaaccau uuguaaaaug   300
gaaugugauu uguaucggcu gaagauuaua accagcugau gguaggccc aggucauuau    360
uaaccaaaac uauuugcgga ggaaaaaugg aacgcccacc ccgaaacgaa cccacugugg   420
acccagugaa uggaguggguc caaccacuag uccagccacc uccagagagu ccgggccgcg   480
ucaccaauca acuucaguuu uuacagaaaa cuguguuaaa ggcugucugg aagcaccaau   540
ucgcuuggcc cuuccagcaa cccgucgaug cuagaaaacu caacuugccc gacuaucaua   600
ggauaauuaa acagccaaug gaccugggaa caauuaagaa aagacuagac aacaauuacu   660
acuggucggg caaagagugc auccaagacu ucaacacgau guuuacaaac ugcuaugucu   720
acaacaagcc uggagaggau guuguuguca uggcucaaac guuagaaaag guauuuuuga   780
caaaagugggc ggauaugcca aaggaggaau uguuguuga aucgcccggu aaagcgggag   840
cggcaaaagg aaagaagggg cggaccagua cagcggggcgc ugucagugca ccccaacac     900
caacuacagc caccgcuggu ucggggaggca gggguaggcc uccgccacu gucucuucua     960
caagcgccac uccaguugcu accacuacag gaucuucagg guuaccuuua ggcacucaag  1020
caccggcuac aguaccuggc agcaccgcaa cuaccaccau agcggcggcc agcaccaaca  1080
acagcucucu gucgaaucag caacugaacu cuucuuccag uuccauucac ggaagcggcu  1140
ccaguuuagg aaauuccuua gauccagca gcgucaugcc ugccaacguu auaccuccgg   1200
cacaaccagc caagguaaaa aagggcguga aagaaaaggc cgauacuacg acgccugcua  1260
cagccuacga uuuccgcca acuuggagu cgaagcucgc aaagauaucg acgcgccgag   1320
aguccgguag gcaaaucaaa aagcccacca ggccagaacu ggacggucau ccgccacaac  1380

```
ccccuccacu uaaaccaaaa gaaaaacuac cagaaucacu gaaagccugc aaugaaaucc   1440
uccuagaauu guucucuaag aaacauucua guuacgccug gccuuuuuau caacccguag   1500
acgcagaauu acucggucug cacgacuacc acgacaucau aaagaaaccg auggauuuua   1560
guacuguaaa aaauaaaaug gaaaaccgag aguaucgcac uccucaagac uuugccgccg   1620
acguuagacu gauuuuuagu aauuguuaca aguacaaccc uucugaccac gaugugguug   1680
cuauggcgag gaaguugcag gauguguuug aagugaaaua ugcaaagauu cccgaugaac   1740
cugucaauag gguaggagcc ccugccguua auaauauacc ugccaaauca gaaacgagua   1800
cauccgguuc caguucggau ucuucuagcg acacggaaga uucggaggaa gaaaggcgaa   1860
acaaacaacu gaagcugcua gaaaagagu ugacggcaau gcaagaaaaa augcguaaau   1920
ugguagacga gagcucgaaa aagaaaaaag aaaagaaaaa ggacaaagug aaaaagaaac   1980
cgacaucagg ugggucucug gcgaacgccu cacuaucaac ucuaccgaac agcagcagcg   2040
cgggcuuggg uaagccgggu gccggugguc acggggcucu aaacaaguca aacaacaaca   2100
acucaauagc ggcggacagc guugacgaca gcaucgccag uuugugucg ggggccgauc   2160
uaaagauggc cgagucgcac cauccgcaaa cuggaacagg cgcucaccau ccgccggcag   2220
gcaaauccu gaacaugcau cacaacauga cggcuaacgc uggcgccaac gcuuccgcgc   2280
aggcuaaaac accuaaaagu aaaggacucc gcggcaauaa acccgcugca gcuaccaacg   2340
cggcucccaa caagaggguc aaagccaaca acaaagcugg ugcggguagg aagaagaacg   2400
cagcacaacc accaccuaug caguucgauu cugaggacga agacaacgcc aaaccgaugu   2460
cuuacgacga gaaacggcag uugucuuugg auauuaauaa auuaccaggu gacaaauugg   2520
guagaguugu acauauaauc caauccaggg aaccgucguu gagggauucc aauccgacg    2580
aaaucgagau cgauuucgaa acgcugaaac ccucaacacu cagagaauua gagaguuacg   2640
uugcgucgug ucuucgcaaa aagccacaua aaaaaguagc gggcaaaucu aaggacgaac   2700
aaauagcgga gaagaagcaa gaguuagaga aagacuaau agacguaaac gauaaaaucg   2760
gcaacuccaa gaaggccccc aaaaaagaug aagccaacaa gguagaccca acgggcgcgg   2820
gaggucccuc aggccgccua uccucuaguu ccagcaguuc ggacuccgac agcaguagua   2880
gcaguuuguc cucuaguucu agcgacucca gugacaguga agcaggugggg acggcgaacc   2940
ggcaggccaa aaagaaagcg aauaaaaaau caccaauc uucucuaggc aguccacca    3000
ccacuacgac uauaaaagug ccgccgccuc aaacgacggc aacaccugca ccgccgucac   3060
aagccgcacc agcaucacg acagcagcaa ccgcuaauuu aaccacaacu guaaccuac    3120
caccacuuac uaccacaacg acaaauacga uagcuccaac aaucgggaca ucccagaaca   3180
auauuccggg cagcagcagu aagcaacgag uuauggacag uuuuaagcau uccagaauag   3240
gaacgaaaaa gaaaauaac gacaaaccac aucauaacgu caaaaacacu aagccuugcu    3300
cgagcuuggc caagggaaa ucaccacaga acaauauccc aggcggcagc aguaaacaaa    3360
cuaaagaaaa ggccgauaga gagaaacaaa ggcuggagaa cuuagaaaug aagcggcaac   3420
agagggaaca agcggagagg gagagguuac gggcggaaaa cgaaaggcga agggaacggg   3480
aagaagaaga ugcgcucgag aaagcaagga aggcuguagc ggagcagcaa cagccuauag   3540
caagccaaag gguggaagaa cugaggucgu cgccgggaa aggaaguaca ucuccagguu   3600
ccuuaaguuc ugguuccgaa aggauaucgg agcgagaaag gcagagguug caggagcagg   3660
aaaggcgaag aagagaagug auggccaaua agauagauau gaacaugcag agugaucuaa   3720
```

```
uggcugcuuu cgaagguucg uuaugaacgg ugauagucgu gugcguuuga cugaauauua    3780
aagauaauag aaaaagagac uccacgagcc aauuuuuugu guauuuaugu auuuauauga    3840
caauuuuaau aggguguuaaa uaaaauguua gacgcucaaa aauuuuugaa aaaugcuucc   3900
auuaugauga guuucgcuuc ggauauauac cucugauuuc uuugaguuga ucauuuuuuu    3960
guguucgugg cuugacucga uuuuaaauau uuuuuauaua uaauauauaa guuggacauu    4020
uucaacaugg uuuguauaua uaacacuaua aauugauuau aaaguguguac auaaugaugu   4080 ugggguugauu auuguguuag uuuuuauuuu auugucuauu ccuccuuguc auuguuuau    4140 uuuaaagcau cuuuugacuu ucacggcuac aggacggucc uaauaugcgg cccaauccac    4200
uugcagauca uuucaauuau aauauuaaua uuauuuuaaa auauuuguac aaaacgaaga    4260
ggaauguguu aaauucaagu gaucagcauu ggauuguaca ccugugcaca ccuuuaaauu    4320
auuggcguca auguuaggau gacucuuuca cauaaaccuu guccuacaca uugacuuaca    4380
guggguauuu aaauuauuaa agccacacag agaagauuuu ugucuaaaag ggauuuguau    4440
augaauucca agguauauug aauguuuauu cacauuuugu uucaugauca cacuuuagga    4500
uuuaaaaagg auaggaagaa auuggacuuu ucaugaaaaa uauuuaaaau uuuaccauau    4560
gcauaauauu ugacgauacc acccauuucu uguugcuuua agcucgacac uaauugauuu    4620
gauauuuccu uuuuucauca acuuucaaga uuuucaaaug caucaaaauc uggcuaguuu    4680
gcgggccagu cgaauauuuu acauauagau aacguaugca guaagcgaca cgcuacuaga    4740
caaaugguag guaccuaauu gcuaugcuuu uggggcuaauc cgguccguuc ucaugugacu   4800
uucaugucua ucgugucaug ugacucuaag ccgcacauca aagaaacaug aaauguaaau    4860
cacguuucau ggaagugaaa caccgcuaaa caaauagacg u                       4901
```

<210> SEQ ID NO 90
<211> LENGTH: 4656
<212> TYPE: RNA
<213> ORGANISM: Diabrotica virgifera

<400> SEQUENCE: 90

```
agagaagcca uuuguaugac cucaaaaagu aaaucuauaa uccuuugaca ucguaacgga      60
acuuguaaaa ucagcaaaua uuuugaagua uuuaauagca caaucguauu uaaauccaau    120
auuuuacagu auuuugauau auuuaacuc uuuuuauaag gcauaucag uaaugaagau     180 uauuuguuca gugcaaggcu cucacacguc cgccaucacg acaguuugug gcaagcuugg    240
ccagcgggua uguuuaggu gagugagagu gguguagcuc cguauuuuuc acgauucuaa     300
uguggauuau cacucaaaag acgcagaucc aagcuaugau ggcuuuuauc uacuaagaaa    360
ccauuuguaa aauggaaugu gauuuguauc ggcugaagau auaaccagc ugauuggguag    420 gcccagguca uuauuaacca aaacuauuug cggaggaaaa auggaacgcc caccccgaaa    480
cgaacccacu guggacccag ugauggagu gguccaacca cuagccagc caccuccaga     540 gaguccgggc cgcgucacca aucaacuuca guuuuuacag aaaacugugu uaaaggcugu    600
cuggaagcac caauucgcuu ggcccuucca gcaacccguc gaugcuagaa aacucaacuu    660
gcccgacuau cauaggauaa uuuaaacagcc aauggaccug gaacaauua agaaaagacu    720 agacaacaau uacuacuggu cgggcaaaga gugcauccaa gacuucaaca cgauguuuac    780
aaacugcuau gucuacaaca agccuggaga ggauguuguu gucauggcuc aaacguuaga    840
aaagguauuu uugacaaaag uggcggauau gccaaaggag gaauuguug uugaaucgcc    900 cgguaaagcg ggagcggcaa aaggaaagaa ggggcggacc aguacagcgg gcgcugucag    960
```

```
ugcacccca  acaccaacua  cagccaccgc  ugguucggga  ggcaggggua  ggccucccgc   1020
cacugucucu  ucuacaagcg  ccacuccagu  ugcuaccacu  acaggaucuu  caggguuacc   1080
uuuaggcacu  caagcaccgg  cuacaguacc  uggcagcacc  gcaacuacca  ccauagcggc   1140
ggccagcacc  aacaacagcu  cucugucgaa  ucagcaacug  aacucuucuu  ccaguuccau   1200
ucacggaagc  ggcuccaguu  uaggaaauuc  cuuagauucc  agcagcguca  ugccugccaa   1260
cguuauaccu  ccggcacaac  cagccaaggu  aaaaagggc   gugaaagaa   aggccgauac   1320 uacgacgccu  gcuacagccu  acgauuaucc  gccaacuuug  gagucgaagu  cugcaaagau   1380
aucgacgcgc  cgagaguccg  guaggcaaau  caaaagccc   accaggccag  aacuggacgg   1440
ucauccgcca  caacccccuc  cacuuaaacc  aaagaaaaa   cuaccagaau  cacugaaagc   1500
cugcaaugaa  auuccccuag  aauuguucuc  uaagaaacau  ucuaguuacg  ccuggccuuu   1560
uuaucaaccc  guagacgcag  aauuacucgg  ucugcacgac  uaccacgaca  ucauaaagaa   1620
accgauggau  uuuaguacug  uaaaaaauaa  aauggaaaac  cgagaguauc  gcacccucca   1680
agacuuugcc  gccgacguua  gacugauuuu  uaguaauugu  uacaaguaca  acccuucuga   1740
ccacgaugug  guugcuaugg  cgaggaaguu  gcaggaugug  uuugaaguga  aauaugcaaa   1800
gauucccgau  gaaccuguca  auagggguagg  agccccugcc  guuaauaaua  uaccugccaa   1860
aucagaaacg  aguacauccg  guuccaguuc  ggauucuucu  agcgacacgg  aagauucgga   1920
ggaagaaagg  cgaaacaaac  aacugaagcu  gcuagaaaaa  gaguugacgg  caaugcaaga   1980 aaaaugcgu   aaauuggaug  acgagagcuc  gaaaaagaaa  aagaaaaga   aaaggacaa   2040 agugaaaaag  aaaccgacau  caggugggc   ucuggcgaac  gccucacuau  caacucuacc   2100
gaacagcagc  agcgcgggcu  ugggacuccg  cggcaauaaa  cccgcugcag  cuaccaacgc   2160
ggcucccaac  aagaggguca  aagccaacaa  caaagcuggu  gcgguagga   agaagaacgc   2220 agcacaacca  ccaccuaugc  aguucgauuc  ugaggacgaa  gacaacgcca  aaccgauguc   2280
uuacgacgag  aaacggcagu  ugucuuugga  uauuaauaaa  uuaccaggug  acaaauuggg   2340
uagaguugua  cauauaaucc  aauccaggga  accgucguug  agggauucca  auccugacga   2400
aaucgagauc  gauuucgaaa  cgcugaaacc  cucaacacuc  agaaauuag   agaguuacgu   2460 ugcgucgugu  cuucgcaaaa  agccacguaa  gccauacuau  aaaaaaguag  cgggcaaauc   2520
uaaggacgaa  caaauagcgg  agaagaagca  agaguuagaa  aaaagacuaa  uagacguaaa   2580
cgauaaaauc  ggcaacucca  agaaggcccc  caaaaaagau  gaagccaaca  agguagaccc   2640
aacgggcgcg  ggagguccu   caggccgccu  auccucuagu  ccagcaguu   cggacuccga   2700 cagcaguagu  agcaguuugu  ccucuaguuc  uagcgacucc  agugacagug  aagcaggugg   2760
gacggcgaac  cggcaggcca  aaaagaaagc  gaauaaaaa   ucacccaauc  cuucucuagg   2820
caguuccacc  accacuacga  cuauaaaagu  gccgccgccu  caaacgacgg  caacaccugc   2880
accgccguca  caagccgcac  cagcuaucac  gacagcagca  accgcuaauu  uaaccacaac   2940
uguaaccgua  ccaccacuua  cuaccacaac  gacaaauacg  auagcuccac  caauucaacc   3000
ggcgccaguu  ccaaacgucg  caguucccgc  gcaaacgacg  ccagccgcac  ccgccuucac   3060
gccgagcaua  accaucaaac  caucacuaca  ggccgccccu  aucgucccga  cggugccgcc   3120
ucuuaucaag  ucaaucgaga  aacugccugu  cacaacucuc  uuaccuccua  ccguuccuac   3180
gauaacgccu  ccaacaguac  cucaagcccc  caaaucggua  gcgcuaccga  cucccuucuccc  3240 ugauaaaccu  aaaccuaaca  uuauuucucc  cauugguacc  uuuaccgacc  cuaucgaaca   3300
```

| | |
|---|---|
| aucauuggcu agucuugaac acgauauuaa gcagaaugau ccuaggacg ucauuacggc | 3360 |
| gucuacuaug augcaaaugc cuacuacacu aaccaauccu aucgugucac auccacaucc | 3420 |
| uaacuuaaac uuaaauccca ccauuaacca uccuauuuua cagccuagca cacuuaguau | 3480 |
| ggacuuaaaa gcgccuauua ugggcacuau ggcgccgagc aauaccaugu ugcaucacgg | 3540 |
| auugcaacaa gcaauggaaa cggauaucag uauaccucca ccccccacca acaugcugca | 3600 |
| uggacagaac aacgguuuug gcaugaaaca caauuuugau cugacuacaa acaacaacgg | 3660 |
| ucuuccucg augggucugc ccauggaaau gucgauaucg ucaauguuug auccaauucc | 3720 |
| acaaaauauu aaucccauga ugaagaacga uucccaacuc aagauggacg aucgcaugga | 3780 |
| uaccuuaggu ggacuuuuga acgacaagaa guccaaucuc cucauacaaa agccgauguc | 3840 |
| gcagucguuu gguuucaaga augacaaacc agaucauaac gucaaaaacg cuaguuccug | 3900 |
| gucgaguuug gccaaaggaa aaucaccaca aaacaauauu ccggcggca gcaguaaaca | 3960 |
| acaaguuaug gauaguuuua aggcauucca aaauaaagcu aaagaaaagg ccgauagaga | 4020 |
| gaaacaaagg cuggagaacu uagaaaugaa gcggcaacag agggaacaag cggagaggga | 4080 |
| gagguuacgg gcggaaaacg aaaggcgaag ggaacgggaa gaagaagaug cgcucgagaa | 4140 |
| agcaaggaag gcuguagcgg agcagcaaca gccauagca agccaaaggg uggaagaacu | 4200 |
| gaggucgucg ccuggugaag gaaguacauc uccagguucc uuaaguucug guuccgaaag | 4260 |
| gauaucggag cgagaaaggc agagguugca ggagcaggaa aggcgaagaa gagaagugau | 4320 |
| ggccaauaag auagauauga acaugcagag ugaucaaaug gcugcuuucg aagguucguu | 4380 |
| augaacgugu auagucgugu gcguuugacu gaauauaaa gauaauagaa aaagagacuc | 4440 |
| cacgagccaa uuuuugugu auuuauguau uauaugaca auuuaauag uguuuaaaua | 4500 |
| aaaguuaga cgcucaaaaa uuuugaaaa augcuuccau uaugaugagu uucgcuucgg | 4560 |
| auauauaccu cugauuucuu ugaguugauc auuuuuuugu guucguggcu ugacucgauu | 4620 |
| uuaaauauuu uuuauauaua auauauaagu uggaca | 4656 |

<210> SEQ ID NO 91
<211> LENGTH: 445
<212> TYPE: RNA
<213> ORGANISM: Diabrotica virgifera

<400> SEQUENCE: 91

| | |
|---|---|
| ucuuccgugu cgcuagaaga auccgaacug gaaccggaug uacucguuuc ugauuuggca | 60 |
| gguauauuau uaacggcagg ggcuccuacc cuauugacag guucaucggg aaucuuugca | 120 |
| uauuucacuu caaacacauc cugcaacuuc cucgccauag caaccacauc ugggucagaa | 180 |
| ggguugacu uguaacaauu acuaaaaauc agucuaacgu cggcggcaaa gucuugagga | 240 |
| gugcgauacu cucgguuuuc cauuuauuu uuuacaguac uaaaauccau cgguuucuuu | 300 |
| augaugucgu gguagucgug cagaccgagu aauucgcgu cuacggguug auaaaaaggc | 360 |
| caggcguaac uagaauguuu cuuagagaac aauucuagga ggauuucauu gcaggcuuuc | 420 |
| agugauucug guaguuuuc uuuug | 445 |

<210> SEQ ID NO 92
<211> LENGTH: 482
<212> TYPE: RNA
<213> ORGANISM: Diabrotica virgifera

<400> SEQUENCE: 92

| | |
|---|---|
| acuuccucgc cauagcaacc acaucguggu cagaaggguu guacuuguaa caauuacuaa | 60 |

```
aaaucagucu aacgucggcg gcaaagucuu gaggagugcg auacucucgg uuuuccauuu    120
uauuuuuuac aguacuaaaa uccaucgguu ucuuuaugau gucgggguag ucgugcagac    180
cgaguaauuc ugcgucuacg gguugauaaa aaggccaggc guaacuagaa uguuucuuag    240
agaacaauuc uaggaggauu ucaugcagg cuucaguga uucgguagu uuucuuug        300 guuuaagugg agggguugu ggcggaugac cguccaguuc uggccuggug ggcuuuuga      360 uuugccuacc ggacucucgg cgcgucgaua ucuuugcaga cuucgacucc aaaguuggcg   420
gauaaucgua ggcuguagca ggcgucguag uaucggccuu ucuuucacg cccuuuuua     480 cc                                                                    482

<210> SEQ ID NO 93
<211> LENGTH: 143
<212> TYPE: RNA
<213> ORGANISM: Diabrotica virgifera

<400> SEQUENCE: 93
guucaucggg aaucuuugca uauuucacuu caaacacauc cugcaacuuc cucgccauag    60
caaccacauc guggucagaa ggguuguacu uguaacaauu acuaaaaauc agucuaacgu   120
cggcggcaaa gucuugagga gug                                            143

<210> SEQ ID NO 94
<211> LENGTH: 164
<212> TYPE: RNA
<213> ORGANISM: Diabrotica virgifera

<400> SEQUENCE: 94
acuuccucgc cauagcaacc acaucguggu cagaaggguu guacuuguaa caauuacuaa    60
aaaucagucu aacgucggcg gcaaagucuu gaggagugcg auacucucgg uuuuccauuu   120
uauuuuuuac aguacuaaaa uccaucgguu ucuuuaugau gucg                     164

<210> SEQ ID NO 95
<211> LENGTH: 805
<212> TYPE: RNA
<213> ORGANISM: Euschistus heros

<400> SEQUENCE: 95
agaauacaaa acagcaacug aauuugcugc ugaugugaga cuaauuuuua caaauuguua    60
caaguauaau cccccggacc augauguugu ugcaaugggc cgaaaauugc aggauguuuu   120
ugaagugagu uaagaaucau gcaggaagag augagaaaac ucgucgaaga aggaacuguu   180
aaaaagaaga agaaaaagaa agaagguuca gguucggug gaaguucuuc uaguaagaaa   240
cggaaaucug cugauaggac auuagguaaa acagccgaug ggggcuuau agcuggugcc   300 ggagcacccg cuaucaugga aauaaaggcu acugauggcg uaaaggcugu cccuccucca   360
ggcaggaaug cagucccuuc accccagguc aaaccaaaca agggcaaagc cccuggaagg   420
gcaccaggaa aaaccaauuc ucagggguaag aggccaaagc cgaacuccag gucuacuaac   480
ucuaagaaga agaauccugu ugucacuuca gauuuaacu cggaagauga ggauaaugca   540
aagccuaugu cuuaugauga aaagagacaa cuuagcuugg auauuaacaa gcuaccaggu   600
gauaaacuug gaagaguagu ccauaucauu caggccagag agcccucuuu gagggauuca   660
aacccugaug aaauugaaau agacuuugag acauugaagc caucaacccu gagggagcuc   720
gaguccuacg uugcaucaug ucucaggaaa aagccacaua agaaaaaugu aucagacaaa   780
```
aaucaaaaag augaagcgau ggccg                                        805

<210> SEQ ID NO 96
<211> LENGTH: 4607
<212> TYPE: RNA
<213> ORGANISM: Euschistus heros

<400> SEQUENCE: 96
uguaaauguu cccauccauu auuucgguau auugauguau accguuuuag gcucagccuu      60
auuggcuucu ucccgagugg ggagcccgcc auguugacca acuaagcgcc aaaagaggag     120
cuuuuuggu auuuuuucuc uuuguuuagg uaaaaaaaua guuaaguauu guuaaauuga     180
uguuagggu acguuacgaa ugaucuugaa guggugaugu gguuacuccc ccuuucgagu     240
acaguagcuu aaccaagcuu guguggggcu ugagcuucuc ucgucuucug uagcuuuacu     300
uuacguuuau uacuggauaa agugaaaaau aaguguuaaa uacaagugug uggacuccag     360
gaagggauuu ugugcuaaau gaaauaguuu uuuguuuaau aacagugauu uggaucguu     420
uuuaaaggua gugugaaaug cgguuuguua uucucaggag uaccccgag gccacaucca     480
aaauucaauu uuuuucuuca aguuucccc ugaagguuc uguuaugacu aauauacuca     540
aguaaauugu uaucuuguug uuccuuaaau uaggacuaaa gauauggga guaguuuuaa     600
cuaagcauuu cuguaugcca uuuuuauag aaagcaaug uaagguuauu gagauuuaaa     660
uguuccugua agaucaugau uucaucuuau gucuuacuc agaugcgucu gcauugggcu     720
uuuuuacagu acuaaugaaa accucaguga caaucgaucc uuggaaagga guguggccaa     780
aaugcaacaa auggacuccu ugcaaccuaa caacgcaaca ggacuggguga aaagcggacu     840
agaggcgggg gccgguagcg gcaugaagga gccccgcca cgagaggagc cgguccuaga     900
cccaaucaau gguguugucc agccuccggu cauaccuccu ccccacaggc cuggccgagu     960
aaccaaccaa uugcaauaua uucagaaaaa uguccuuaaa gcagucugga aacaucaaua    1020
ugcuuggccu cuacagcaac cugucgaugc uaauaaacuc aaucuuccug auuaccauaa    1080
aguuauuaaa cauccaaugg aucuugguac uaucaaaaaa cgacuggaaa acaauuauua    1140
uuggguggu gcuagaugua uucaagauuu caacacaaug uuuaacaauu guuauguuua    1200
uaacaaacca ggagaagaug uuguuguauu ggcucaaacg cuggaaaaac uuuauuugca    1260
aaagcuggaa acaaugccca agaggaaau ugagcuugag ccuccaccac cuaaaggnuc    1320
uaagccaguu aagaagcgac cuggaguuau aggucaggu agaggggcg ggaccacugg    1380
cgcaggaaga gggaggccuu ccaauucaac gccagcagcu gcggcaguag ucaccacucc    1440
uguaccuccu gucacucccc caucacaccu uccagcaacc auaccugguu cgacugcuac    1500
uaccacugua ccuacuacuc accauaacuc ucccccccu cagguuggc agccagcagc    1560
uguacccucc aacuucagua caacuacugu ugaucccuu uuaacaccug gauuggcucc    1620
ugguguggu ccaaaaggug gcaaggggc cgucguccag accccaacgg cgcccaaacc    1680
gaaaaaaggg gucaaaagaa aggcugaucu agcgaaugau agccccgcua guuuugaccc    1740
aacauacacc ccaggugacu ccaaagcugc caagguuggc acuaggagag aaucuggaag    1800
gcaaauuaaa aagccucaaa gacagucaga cgaugguaug ccauuuucuc aaagcccaau    1860
ggcaccuuau ucacuuucaa auucaacgca ggcugcccau gaaaagccga agaaaaacu    1920
cucugaaaca uuaaagcau guaaugaaau auugaaggag uuauuucua aaaacauuu    1980
uaauuaugcu uggcccuucu auaaaccugu ugaugccgaa uggcuagguu uacaugacua    2040
ccaugauauu auuaagaaac cuauggaucu cggaacugua aagcaaaaaa uggacaaucg    2100

```
agaauacaaa acagcaacug aauuugcugc ugaugugaga cuaauuuuua caaauuguua    2160
caaguauaau cccccggacc augauguugu ugcaaugggc cgaaaauugc aggauguuuu    2220
ugaagugaga uucgcucaag uaccugaaga cuccccuaua ucgacuguuc cugaaaagga    2280
agaagaaucc accucugggu caucgucugg cucugaaucc gaaacagaua auucagauga    2340
cgaaagggcc cguaaacuua gucaauuaca agagcaguua agaaucaugc aggaagagau    2400
gagaaaacuc gucgaagaag gaacuguuaa aagaagaag aaaagaaag aagguucagg     2460 uucggugga aguucuucua guaagaaacg gaaaucugcu gauaggacau uagguaaaac     2520
agccgauggu gggcuuauag cuggugccgg agcacccgcu aucauggaaa uaaaggcuac    2580
ugauggcgua aaggcugucc cuccuccagg caggaaugca gucccuucac cccaggucaa    2640
accaaacaag ggcaaagccc cuggaagggc accaggaaaa accaauucuc agguaagag    2700 gccaaagccg aacuccaggu cuacuaacuc uaagaagaag aauccuguug ucacuucaga    2760
guuuaacucg gaagaugagg auaaugcaaa gccuaugucu uaugaugaaa agagacaacu    2820
uagcuuggau auuaacaagc uaccagguga uaaacuugga agaguagucc auaucauuca    2880
ggccagagag cccucuuuga gggauucaaa cccugaugaa auugaaauag acuuugagac    2940
auugaagcca ucaaccccuga gggagcucga guccuacguu gcaucaugauc ucaggaaaaa    3000 gccacguaag cccuacaaua agaaaaaugu aucagcaaaa ucaaagaug aagcgauggc    3060 cgagaagaaa caagagcuag aaaaaaggcu ucaggauguu acuggucaau ugggaggauc    3120
agcuaagaaa acagcuaaaa aacaagguca gggaaggcuu ucagcgucau cgucaucaag    3180
cucagauucu gauacaagua guucaagucu cucuagcagu ucuuccgacu caucugauag    3240
cgaagcaggg aaggcagggc guccaccgag gaagaaaaau aagaaaaauc accaaauagc    3300
aacaacugcu gcaacaacug uccaacagaa ucaaacugua ccaagcuuga ccaugacaac    3360
ugccacuggu acuauuguaa auaaaaaugc uggggcucca cagcccguag uaccguuagc    3420
aagcaccaac aaaccuacug uaccuccggu cucugcagug acacagccug aaccugugaa    3480
accuguugua gcaucacaua gcuugccucc ccaaccugcg aggccuaccg caacggcugc    3540
cccucugaca acugcuaaga gggcgucaau ccccacgcca gcgacaucga ugggcauacc    3600
uccgccugcu ccgacugguc uugaaacagg uccuauugag aucaaacagg aauuggaugu    3660
uccuguucca cuagcacccg uuccagauca uuuggauuuc aaaaaccuuu uggaggugaa    3720
gcccgagcua aaugauaucg uuacgggau gccuucugua uuugauccuu gccugacuc     3780 accucccauc auuaaggaag aaaagcaucc uauacucccc caucacacag auggacacuu    3840
gaacaauucu cuuccccug ucagcaacgu accgguccg ccaaucauac cgagugcugc     3900
acuuccaacu acaccacauc acuuagauau gaauaagaau ucccagccuc ucagcuuc     3960 ccagacgcca acuuuacaac accccuucaa accuaagaau uuuggcuuca cauugaugg    4020 cugcuuaagg auucaaagaa cuguugagca gaacuugaaa aaugccaguu caugggcuuc    4080
acuugcccag uccccaacac cagcucucac cccaacucca ccgacugcgg cucugaaguc    4140
cucaaugcgu gacagcuuuc aagcuuuuaa gaaacaagcu aaagaaaaug ccaagaagca    4200
acgagcccug auugaacagc aagaaaugag gcgacaucaa aaagaacagg cugaaaggga    4260
aagauuacgu guugaaaccg aaaagagag agaaagagaa gaagaagaag cucuggagaa    4320 ggcuagaaaau aguuaugucg ggaacaggaa ggcugcugua guggcuucug gaagaguuga    4380
agagguuaaa aaugcugcua ucgaggaagg uaccagccca gguucggcag acaaagcugc    4440
```
ugcagagcga gaacgucuaa ggcaacgaga gcaagagagg cggcgaagag aagcauuggc 4500
ugggcaaauu gauaugaaca ggcaaaguga uuuaauggcu gcuuuugaac agaccuugua 4560
auucuucaag ggcaguuuuu guguuuucuu uucuuucuuu uuuuuaa 4607

<210> SEQ ID NO 97
<211> LENGTH: 367
<212> TYPE: RNA
<213> ORGANISM: Euschistus heros

<400> SEQUENCE: 97
gccccuggaa gggcaccagg aaaaaccaau ucucagggua agaggccaaa gccgaacucc 60
aggucuacua acucuaagaa gaagaauccu guugucacuu cagaguuuaa cucggaagau 120
gaggauaaug caaagccuau gucuuaugau gaaaagagac aacuuagcuu ggauauuaac 180
aagcuaccag gugauaaacu uggaagagua guccauauca uucaggccag agagcccucu 240
uugagggauu caaacccuga ugaaauugaa auagacuuug agacauugaa gccaucaacc 300
cugagggagc ucgaguccua cguugcauca ugucucagga aaaagccaca uaagaaaaau 360
guaucag 367

<210> SEQ ID NO 98
<211> LENGTH: 430
<212> TYPE: RNA
<213> ORGANISM: Euschistus heros

<400> SEQUENCE: 98
acagucagac gaugguaugc cauuuucuca aagcccaaug gcaccuuauu cacuuucaaa 60
uucaacgcag gcugcccaug aaaagccgaa agaaaaacuc ucugaaacau uaaaagcaug 120
uaaugaaaua uugaaggagu uauuuucuaa aaaacauuuu aauuaugcuu ggcccuucua 180
uaaaccuguu gaugccgaau ggcuagguuu acaugacuac caugauauua uuaagaaacc 240
uauggaucuc ggaacuguaa agcaaaaaau ggacaaucga gaauacaaaa cagcaacuga 300
auuugcugcu gaugugagac uaauuuuuac aaauuguuac aaguauaauc ccccggacca 360
ugauguuguu gcaaugggcc gaaaauugca ggauguuuuu gaagugagau ucgcucaagu 420
accugaagac 430

<210> SEQ ID NO 99
<211> LENGTH: 24
<212> TYPE: DNA
<213> ORGANISM: Artificial Sequence
<220> FEATURE:
<223> OTHER INFORMATION: Probe Fsh-2v1 PRB Set 1

<400> SEQUENCE: 99
aatcagtcta acgtcggcgg caaa 24

<210> SEQ ID NO 100
<211> LENGTH: 153
<212> TYPE: DNA
<213> ORGANISM: Artificial Sequence
<220> FEATURE:
<223> OTHER INFORMATION: Linker polynucleotide

<400> SEQUENCE: 100
agtcatcacg ctggagcgca catataggcc ctccatcaga aagtcattgt gtatatctct 60
catagggaac gagctgcttg cgtatttccc ttccgtagtc agagtcatca atcagctgca 120
ccgtgtcgta aagcgggacg ttcgcaagct cgt 153

```
<210> SEQ ID NO 101
<211> LENGTH: 153
<212> TYPE: RNA
<213> ORGANISM: Artificial Sequence
<220> FEATURE:
<223> OTHER INFORMATION: hpRNA molecule loop polyribonucleotide

<400> SEQUENCE: 101
agucaucacg cuggagcgca cauauaggcc cuccaucaga aagucauugu guauaucucu        60
cauagggaac gagcugcuug cguauuuccc uuccguaguc agagucauca aucagcugca       120
ccgugucgua aagcgggacg uucgcaagcu cgu                                    153
```

FSH NUCLEIC ACID MOLECULES TO CONTROL INSECT PESTS

CROSS-REFERENCE TO RELATED APPLICATIONS

This application claims the benefit under 35 U.S.C. § 119(e) to U.S. Provisional Patent Application Ser. No. 62/318,621 filed Apr. 5, 2016, the disclosure of which is hereby incorporated by this reference in its entirety.

TECHNICAL FIELD

The present invention relates generally to genetic control of plant damage caused by insect pests (e.g., coleopteran pests and hemipteran pests). In particular embodiments, the present invention relates to identification of target coding and non-coding polynucleotides, and the use of recombinant DNA technologies for post-transcriptionally repressing or inhibiting expression of target coding and non-coding polynucleotides in the cells of an insect pest to provide a plant protective effect.

STATEMENT ACCORDING TO 37 C.F.R § 1.821(c) or (e)-SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in the Americas: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; *D. speciosa* Germar; and *D. u. undecimpunctata* Mannerheim. The United States Department of Agriculture has estimated that corn rootworms cause $1 billion in lost revenue each year, including $800 million in yield loss and $200 million in treatment costs.

Both WCR and NCR eggs are deposited in the soil during the summer. The insects remain in the egg stage throughout the winter. The eggs are oblong, white, and less than 0.004 inches in length. The larvae hatch in late May or early June, with the precise timing of egg hatching varying from year to year due to temperature differences and location. The newly hatched larvae are white worms that are less than 0.125 inches in length. Once hatched, the larvae begin to feed on corn roots. Corn rootworms go through three larval instars. After feeding for several weeks, the larvae molt into the pupal stage. They pupate in the soil, and then emerge from the soil as adults in July and August. Adult rootworms are about 0.25 inches in length.

Corn rootworm larvae complete development on corn and several other species of grasses. Larvae reared on yellow foxtail emerge later and have a smaller head capsule size as adults than larvae reared on corn. Ellsbury et al. (2005) Environ. Entomol. 34:627-34. WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by, for example, crop rotation; chemical insecticides; biopesticides (e.g., the spore-forming gram-positive bacterium, *Bacillus thuringiensis*); transgenic plants that express Bt toxins, PIP polypeptides (See, e.g., PCT International Patent Publication No. WO 2015/038734), and/or AfIP polypeptides (See, e.g., U.S. Patent Publication No. US 2104/0033361 Al); or a combination thereof. Crop rotation suffers from the disadvantage of placing unwanted restrictions upon the use of farmland. Moreover, oviposition of some rootworm species may occur in soybean fields, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity to non-target species.

Stink bugs and other hemipteran insects (heteroptera) are another important agricultural pest complex. Worldwide over 50 closely related species of stink bugs are known to cause crop damage. McPherson & McPherson (2000) *Stink bugs of economic importance in America north of Mexico*, CRC Press. These insects are present in a large number of important crops including maize, soybean, fruit, vegetables, and cereals.

Stink bugs go through multiple nymph stages before reaching the adult stage. The time to develop from eggs to adults is about 30-40 days. Both nymphs and adults feed on sap from soft tissues into which they also inject digestive enzymes causing extra-oral tissue digestion and necrosis. Digested plant material and nutrients are then ingested. Depletion of water and nutrients from the plant vascular system results in plant tissue damage. Damage to developing grain and seeds is the most significant as yield and germination are significantly reduced. Multiple generations occur in warm climates resulting in significant insect pressure. Current management of stink bugs relies on insecticide treatment on an individual field basis. Therefore, alternative management strategies are urgently needed to minimize ongoing crop losses.

RNA interference (RNAi) is a process utilizing endogenous cellular pathways, whereby an interfering RNA (iRNA) molecule (e.g., a dsRNA molecule) that is specific for all, or any portion of adequate size, of a target gene results in the degradation of the mRNA encoded thereby. RNAi has been used to perform gene "knockdown" in a number of species and experimental systems; for example, *Caenorhabditis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Post-transcriptional gene silencing occurs when the guide strand binds specifically to a complementary mRNA molecule and induces cleavage by Argonaute, the catalytic component of the RISC complex. This process is known to spread systemically throughout the organism despite initially limited concentrations of siRNA and/or miRNA in some eukaryotes such as plants, nematodes, and some insects.

U.S. Pat. No. 7,612,194 and U.S. Patent Publication Nos. 2007/0050860, 2010/0192265, and 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. 2007/0050860 to operably link to a promoter a nucleic acid molecule that is complementary to one of several particular partial sequences of *D. v. virgifera* vacuolar-type H+-ATPase (V-ATPase) disclosed therein for the expression of anti-sense RNA in plant cells. U.S. Patent Publication No. 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midguts, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. 2007/0050860, 2010/0192265, and 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. 2007/0050860, 2010/0192265, and 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA. U.S. Patent Application Publication No. U.S. 2013/040173 and PCT Application Publication No. WO 2013/169923 describe the use of a sequence derived from a *Diabrotica virgifera* Snf7 gene for RNA interference in maize.

The overwhelming majority of sequences complementary to corn rootworm DNAs (such as the foregoing) do not provide a plant protective effect from species of corn rootworm when used as dsRNA or siRNA. For example, Baum et al. (2007) Nature Biotechnology 25:1322-1326, describe the effects of inhibiting several WCR gene targets by RNAi. These authors reported that 8 of the 26 target genes they tested were not able to provide experimentally significant coleopteran pest mortality at a very high iRNA (e.g., dsRNA) concentration of more than 520 ng/cm$^2$.

The authors of U.S. Pat. No. 7,612,194 and U.S. Patent Publication No. 2007/0050860 made the first report of in planta RNAi in corn plants targeting the western corn rootworm. Baum et al. (2007) Nat. Biotechnol. 25(11):1322-6. These authors describe a high-throughput in vivo dietary RNAi system to screen potential target genes for developing transgenic RNAi maize. Of an initial gene pool of 290 targets, only 14 exhibited larval control potential. One of the most effective double-stranded RNAs (dsRNA) targeted a gene encoding vacuolar ATPase subunit A (V-ATPase), resulting in a rapid suppression of corresponding endogenous mRNA and triggering a specific RNAi response with low concentrations of dsRNA. Thus, these authors documented for the first time the potential for in planta RNAi as a possible pest management tool, while simultaneously demonstrating that effective targets could not be accurately identified a priori, even from a relatively small set of candidate genes.

SUMMARY OF THE DISCLOSURE

Disclosed herein are nucleic acid molecules (e.g., target genes, DNAs, dsRNAs, siRNAs, miRNAs, shRNAs, and hpRNAs), and methods of use thereof, for the control of insect pests, including, for example, coleopteran pests, such as *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; *D. u. undecimpunctata* Mannerheim; and *D. speciosa* Germar, and hemipteran pests, such as *Euschistus heros* (Fabr.) (Neotropical Brown Stink Bug, "BSB"); *E. servus* (Say) (Brown Stink Bug); *Nezara viridula* (L.) (Southern Green Stink Bug); *Piezodorus guildinii* (Westwood) (Red-banded Stink Bug); *Halyomorpha halys* (Stål) (Brown Marmorated Stink Bug); *Chinavia hilare* (Say) (Green Stink Bug); *C. marginatum* (Palisot de Beauvois); *Dichelops melacanthus* (Dallas); *D. furcatus* (F.); *Edessa*

*meditabunda* (F.); *Thyanta perditor* (F.) (Neotropical Red Shouldered Stink Bug); *Horcias nobilellus* (Berg) (Cotton Bug); *Taedia stigmosa* (Berg); *Dysdercus peruvianus* (Guérin-Méneville); *Neomegalotomus parvus* (Westwood); *Leptoglossus zonatus* (Dallas); *Niesthrea sidae* (F.); *Lygus hesperus* (Knight) (Western Tarnished Plant Bug); and *L. lineolaris* (Palisot de Beauvois). In particular examples, exemplary nucleic acid molecules are disclosed that may be homologous to at least a portion of one or more native nucleic acids in an insect pest.

In these and further examples, the native nucleic acid sequence may be a target gene, the product of which may be, for example and without limitation: involved in a metabolic process or involved in larval/nymph development. In some examples, post-transcriptional inhibition of the expression of a target gene by a nucleic acid molecule comprising a polynucleotide homologous thereto may be lethal to an insect pest or result in reduced growth and/or viability of an insect pest. In specific examples, a gene encoding a chromatin-binding protein involved in activation of homeotic genes (female sterile (1) homeotic fs(1)h, referred to herein as fsh), or an fsh homolog or ortholog, may be selected as a target gene for post-transcriptional silencing. In particular examples, a target gene useful for post-transcriptional inhibition is afsh gene selected from the group consisting of SEQ ID NO:1; SEQ ID NO:3; SEQ ID NO:76; and SEQ ID NO:78. An isolated nucleic acid molecule comprising the polynucleotide of SEQ ID NO:1; the complement and/or reverse complement of SEQ ID NO:1; SEQ ID NO:3; the complement and/or reverse complement of SEQ ID NO:3; SEQ ID NO:76; the complement and/or reverse complement of SEQ ID NO:76; SEQ ID NO:78; the complement and/or reverse complement of SEQ ID NO:78; and/or fragments comprising at least 15 contiguous nucleotides of any of the foregoing (e.g., SEQ ID NOs:5-8, 80, and 81) is therefore disclosed herein.

Also disclosed are nucleic acid molecules comprising a polynucleotide that encodes a polypeptide that is at least about 85% identical to an amino acid sequence within a target gene product (for example, the product of an fsh gene). For example, a nucleic acid molecule may comprise a polynucleotide encoding a polypeptide that is at least 85% identical to SEQ ID NO:2 (*D. virgifera* FSH-1), SEQ ID NO:4 (*D. virgifera* FSH-2), SEQ ID NO:77 (E. heros FSH-1), SEQ ID NO:79 (E. heros FSH-2); and/or an amino acid sequence within a product of an fsh gene. Further disclosed are nucleic acid molecules comprising a polynucleotide that is the complement or reverse complement of a polynucleotide that encodes a polypeptide at least 85% identical to an amino acid sequence within a target gene product.

Also disclosed are cDNA polynucleotides that may be used for the production of iRNA (e.g., dsRNA, siRNA, shRNA, miRNA, and hpRNA) molecules that are complementary to all or part of an insect pest target gene, for example, an fsh gene. In particular embodiments, dsRNAs, siRNAs, shRNAs, miRNAs, and/or hpRNAs may be produced in vitro or in vivo by a genetically-modified organism, such as a plant or bacterium. In particular examples, cDNA molecules are disclosed that may be used to produce iRNA molecules that are complementary to all or part of an fsh gene (e.g., SEQ ID NO:1; SEQ ID NO:3; SEQ ID NO:76; and SEQ ID NO:78).

Further disclosed are fsh means for inhibiting expression of an essential gene in a coleopteran pest, and fsh means for providing coleopteran pest protection to a plant. Afsh means for inhibiting expression of an essential gene in a coleopteran pest includes a single-stranded RNA molecule consisting of a polynucleotide selected from the group consisting of SEQ ID NOs:91-94; and the complements and reverse complements thereof. Functional equivalents of fsh means for inhibiting expression of an essential gene in a coleopteran pest include single- or double-stranded RNA molecules that are substantially homologous to all or part of an RNA transcribed from a coleopteran fsh gene comprising any of SEQ ID NOs:5-8. A fsh means for providing coleopteran pest protection to a plant includes a DNA molecule comprising a polynucleotide encoding afsh means for inhibiting expression of an essential gene in a coleopteran pest operably linked to a promoter, wherein the DNA molecule is capable of being integrated into the genome of a plant.

Also disclosed are fsh means for inhibiting expression of an essential gene in a hemipteran pest, and fsh means for providing hemipteran pest protection to a plant. A fsh means for inhibiting expression of an essential gene in a hemipteran pest includes a single-stranded RNA molecule consisting of a polynucleotide selected from the group consisting of SEQ ID NO:97; SEQ ID NO:98; and the complements and reverse complements thereof. Functional equivalents of fsh means for inhibiting expression of an essential gene in a hemipteran pest include single- or double-stranded RNA molecules that are substantially homologous to all or part of an RNA transcribed from a hemipteran fsh gene comprising SEQ ID NO:80 or SEQ ID NO:81. A fsh means for providing hemipteran pest protection to a plant includes a DNA molecule comprising a polynucleotide encoding a fsh means for inhibiting expression of an essential gene in a hemipteran pest operably linked to a promoter, wherein the DNA molecule is capable of being integrated into the genome of a plant.

Additionally disclosed are methods for controlling a population of an insect pest (e.g., a coleopteran or hemipteran pest), comprising providing to an insect pest (e.g., a coleopteran or hemipteran pest) an iRNA (e.g., dsRNA, siRNA, shRNA, miRNA, and hpRNA) molecule that functions upon being taken up by the pest to inhibit a biological function within the pest.

In some embodiments, methods for controlling a population of a coleopteran pest comprises providing to the coleopteran pest an iRNA molecule that comprises all or a fragment comprising at least 15 contiguous nucleotides of a polynucleotide selected from the group consisting of: SEQ ID NO:89; the complement or reverse complement of SEQ ID NO:89; SEQ ID NO:90; the complement or reverse complement of SEQ ID NO:90; SEQ ID NO:91; the complement or reverse complement of SEQ ID NO:91; SEQ ID NO:92; the complement or reverse complement of SEQ ID NO:92; SEQ ID NO:93; the complement or reverse complement of SEQ ID NO:93; SEQ ID NO:94; the complement or reverse complement of SEQ ID NO:94; a polynucleotide that hybridizes to a fragment comprising at least 15 contiguous nucleotides of a native fsh polynucleotide of a coleopteran pest (e.g., WCR); the complement or reverse complement of a polynucleotide that hybridizes to a fragment comprising at least 15 contiguous nucleotides of a native fsh polynucleotide of a coleopteran pest; a polynucleotide that hybridizes to a fragment comprising at least 15 contiguous nucleotides of a native coding polynucleotide of a *Diabrotica* organism (e.g., WCR) comprising all or part of any of SEQ ID NOs:1, 3, and 5-8; the complement or reverse complement of a polynucleotide that hybridizes to a fragment comprising at least 15 contiguous nucleotides of a native coding polynucleotide of a *Diabrotica* organism comprising all or part of any of SEQ ID NOs:1, 3, and 5-8.

In some embodiments, methods for controlling a population of a hemipteran pest comprises providing to the hemipteran pest an iRNA molecule that comprises all or a fragment comprising at least 15 contiguous nucleotides of a polynucleotide selected from the group consisting of: SEQ ID NO:95; the complement or reverse complement of SEQ ID NO:95; SEQ ID NO:96; the complement or reverse complement of SEQ ID NO:96; SEQ ID NO:97; the complement or reverse complement of SEQ ID NO:97; SEQ ID NO:98; the complement or reverse complement of SEQ ID NO:98; a polynucleotide that hybridizes to a fragment comprising at least 15 contiguous nucleotides of a native fsh polynucleotide of a hemipteran pest (e.g., BSB); the complement or reverse complement of a polynucleotide that hybridizes to a fragment comprising at least 15 contiguous nucleotides of a native fsh polynucleotide of a hemipteran pest; a polynucleotide that hybridizes to a fragment comprising at least 15 contiguous nucleotides of a native coding polynucleotide of a hemipteran organism (e.g., BSB) comprising all or part of any of SEQ ID NOs:76, 78, 80, and 81; and the complement or reverse complement of a polynucleotide that hybridizes to a fragment comprising at least 15 contiguous nucleotides of a native coding polynucleotide of a hemipteran organism comprising all or part of any of SEQ ID NOs:76, 78, 80, and 81.

In particular embodiments, an iRNA that functions upon being taken up by an insect pest to inhibit a biological function within the pest is transcribed from a DNA comprising all or a fragment comprising at least 15 contiguous nucleotides of a polynucleotide selected from the group consisting of: SEQ ID NO:1; the complement or reverse complement of SEQ ID NO:1; SEQ ID NO:3; the complement or reverse complement of SEQ ID NO:3; SEQ ID NO:5; the complement or reverse complement of SEQ ID NO:5; SEQ ID NO:6; the complement or reverse complement of SEQ ID NO:6; SEQ ID NO:7; the complement or reverse complement of SEQ ID NO:7; SEQ ID NO:8; the complement or reverse complement of SEQ ID NO:8; SEQ ID NO:76; the complement or reverse complement of SEQ ID NO:76; SEQ ID NO:78; the complement or reverse complement of SEQ ID NO:78; SEQ ID NO:80; the complement or reverse complement of SEQ ID NO:80; SEQ ID NO:81; the complement or reverse complement of SEQ ID NO:81; a native coding polynucleotide of a *Diabrotica* organism (e.g., WCR) comprising all or part of any of SEQ ID NOs:1, 3, and 5-8; the complement or reverse complement of a native coding polynucleotide of a *Diabrotica* organism comprising all or part of any of SEQ ID NOs:1, 3, and 5-8; a native coding polynucleotide of a hemipteran organism (e.g., BSB) comprising all or part of any of SEQ ID NOs:76, 78, 80, and 81; and the complement or reverse complement of a native coding polynucleotide of a hemipteran organism comprising all or part of any of SEQ ID NOs:76, 78, 80, and 81.

Also disclosed herein are methods wherein dsRNAs, siRNAs, shRNAs, miRNAs, and/or hpRNAs may be provided to an insect pest in a diet-based assay, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by the pest. Ingestion of dsRNAs, siRNA, shRNAs, miRNAs, and/or hpRNAs of the invention may then result in RNAi in the pest, which in turn may result in silencing of a gene essential for viability of the pest and leading ultimately to mortality. Thus, methods are disclosed wherein nucleic acid molecules comprising exemplary polynucleotide(s) useful for control of insect pests are provided to an insect pest. In particular examples, a coleopteran and/or hemipteran pest controlled by use of nucleic acid molecules of the invention may be WCR, NCR, SCR, MCR, BSB, *D. balteata, D. u. tenella, D. speciosa, D. u. undecimpunctata, E. servus, Piezodorus guildinii, Halyomorpha halys, Nezara viridula, Chinavia hilare, C. marginatum, Dichelops melacanthus, D. furcatus, Edessa meditabunda, Thyanta perditor, Horcias nobilellus, Taedia stigmosa, Dysdercus peruvianus, Neomegalotomus parvus, Leptoglossus zonatus, Niesthrea sidae, Lygus hesperus,* and/or *Lygus lineolaris.*

The foregoing and other features will become more apparent from the following Detailed Description of several embodiments, which proceeds with reference to the accompanying FIGS. 1-2.

SEQUENCE LISTING

Figure 1:
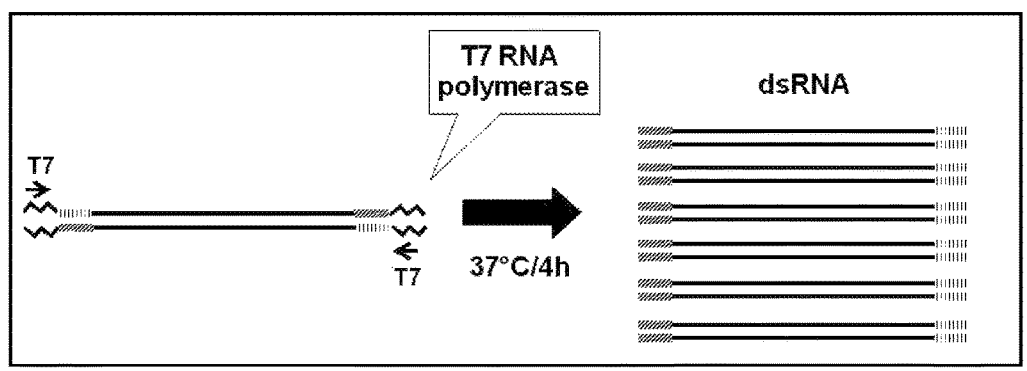
FIG. 1 includes a depiction of a strategy used to generate dsRNA from a single transcription template with a single pair of primers.

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NO:1 shows a contig containing an exemplary WCR fsh DNA, referred to herein in some places as WCR fsh or WCR fsh-1:

```
CGTATGTCGGCGATGTGCGCGAAAATCATTTTCTTCACTTTTCTCTATGATTTTTATATAATTGTG
GAAAATCATAATTTCGCCATATTATGCAACATTTTTTGTTTTTGAATAAAGTGCAAGGCTCTCACA
CGTCCGCCATCACGACAGTTTGTGGCAAGCTTGGCCAGCGGGTATGTGTTAGGTGAGTGAGAGTGG
TGTAGCTCCGTATTTTTCACGATTCTAATGTGGATTATCACTCAAAAGACGCAGATCCAAGCTATG
ATGGCTTTTATCTACTAAGAAACCATTTGTAAAATGGAATGTGATTTGTATCGGCTGAAGATTATA
ACCAGCTGATTGGTAGGCCCAGGTCATTATTAACCAAAACTATTTGCGGAGGAAAAATGGAACGCC
CACCCCGAAACGAACCCACTGTGGACCCAGTGAATGGAGTGGTCCAACCACTAGTCCAGCCACCTC
CAGAGAGTCCGGGCCGCGTCACCAATCAACTTCAGTTTTTACAGAAAACTGTGTTAAAGGCTGTCT
GGAAGCACCAATTCGCTTGGCCCTTCCAGCAACCCGTCGATGCTAGAAAACTCAACTTGCCCGACT
ATCATAGGATAATTAAACAGCCAATGGACCTGGGAACAATTAAGAAAAGACTAGACAACAATTACT
ACTGGTCGGGCAAAGAGTGCATCCAAGACTTCAACACGATGTTTACAAACTGCTATGTCTACAACA
AGCCTGGAGAGGATGTTGTTGTCATGGCTCAAACGTTAGAAAAGGTATTTTTGACAAAAGTGGCGG
ATATGCCAAAGGAGGAATTTGTTGTTGAATCGCCCGGTAAAGCGGGAGCGGCAAAAGGAAAGAAGG
GGCGGACCAGTACAGCGGGCGCTGTCAGTGCACCCCCAACACCAACTACAGCCACCGCTGGTTCGG
GAGGCAGGGGTAGGCCTCCCGCCACTGTCTCTTCTACAAGCGCCACTCCAGTTGCTACCACTACAG
GATCTTCAGGGTTACCTTTAGGCACTCAAGCACCGGCTACAGTACCTGGCAGCACCGCAACTACCA
CCATAGCGGCGGCCAGCACCAACAACAGCTCTCTGTCGAATCAGCAACTGAACTCTTCTTCCAGTT
CCATTCACGGAAGCGGCTCCAGTTTAGGAAATTCCTTAGATTCCAGCAGCGTCATGCCTGCCAACG
TTATACCTCCGGCACAACCAGCCAAGGTAAAAAAGGGCGTGAAAAGAAAGGCCGATACTACGACGC
CTGCTACAGCCTACGATTATCCGCCAACTTTGGAGTCGAAGTCTGCAAAGATATCGACGCGCCGAG
AGTCCGGTAGGCAAATCAAAAAGCCCACCAGGCCAGAACTGGACGGTCATCCGCCACAACCCCCTC
CACTTAAACCAAAAGAAAAACTACCAGAATCACTGAAAGCCTGCAATGAAATCCTCCTAGAATTGT
TCTCTAAGAAACATTCTAGTTACGCCTGGCCTTTTTATCAACCCGTAGACGCAGAATTACTCGGTC
TGCACGACTACCACGACATCATAAAGAAACCGATGGATTTTAGTACTGTAAAAAATAAAATGGAAA
ACCGAGAGTATCGCACTCCTCAAGACTTTGCCGCCGACGTTAGACTGATTTTTAGTAATTGTTACA
AGTACAACCCTTCTGACCACGATGTGGTTGCTATGGCGAGGAAGTTGCAGGATGTGTTTGAAGTGA
AATATGCAAAGATTCCCGATGAACCTGTCAATAGGGTAGGAGCCCCTGCCGTTAATAATATACCTG
CCAAATCAGAAACGAGTACATCCGGTTCCAGTTCGGATTCTTCTAGCGACACGGAAGATTCGGAGG
AAGAAAGGCGAAACAAACAACTGAAGCTGCTAGAAAAAGAGTTGACGGCAATGCAAGAAAAAATGC
GTAAATTGGTAGACGAGAGCTCGAAAAAGAAAAAAGAAAAGAAAAAGGACAAAGTGAAAAGAAAC
CGACATCAGGTGGGTCTCTGGCGAACGCCTCACTATCAACTCTACCGAACAGCAGCAGCGCGGGCT
TGGGTAAGCCGGGTGCCGGTGGTCACGGGGCTCTAAACAAGTCAAACAACAACAACTCAATAGCGG
CGGACAGCGTTGACGACAGCATCGCCAGTGTTGTGTCGGGGGCCGATCTAAAGATGGCCGAGTCGC
ACCATCCGCAAACTGGAACAGGCGCTCACCATCCGCCGGCAGGCAAATCCCTGAACATGCATCACA
ACATGACGGCTAACGCTGGCGCCAACGCTTCCGCGCAGGCTAAAACACCTAAAAGTAAAGGACTCC
GCGGCAATAAACCCGCTGCAGCTACCAACGCGGCTCCCAACAAGAGGGTCAAAGCCAACAACAAAG
CTGGTGCGGGTAGGAAGAAGAACGCAGCACAACCACCACCTATGCAGTTCGATTCTGAGGACGAAG
ACAACGCCAAACCGATGTCTTACGACGAGAAACGGCAGTTGTCTTTGGATATTAATAAATTACCAG
GTGACAAATTGGGTAGAGTTGTACATATAATCCAATCCAGGGAACCGTCGTTGAGGGATTCCAATC
CTGACGAAATCGAGATCGATTTCGAAACGCTGAAACCCTCAACACTCAGAGAATTAGAGAGTTACG
TTGCGTCGTGTCTTCGCAAAAAGCCACATAAAAAAGTAGCGGGCAAATCTAAGGACGAACAAATAG
```

-continued

```
CGGAGAAGAAGCAAGAGTTAGAGAAAAGACTAATAGACGTAAACGATAAAATCGGCAACTCCAAGA

AGGCCCCCAAAAAAGATGAAGCCAACAAGGTAGACCCAACGGGCGCGGGAGGTCCCTCAGGCCGCC

TATCCTCTAGTTCCAGCAGTTCGGACTCCGACAGCAGTAGTAGCAGTTTGTCCTCTAGTTCTAGCG

ACTCCAGTGACAGTGAAGCAGGTGGGACGGCGAACCGGCAGGCCAAAAAGAAAGCGAATAAAAAAT

CACCCAATCCTTCTCTAGGCAGTTCCACCACCACTACGACTATAAAAGTGCCGCCGCCTCAAACGA

CGGCAACACCTGCACCGCCGTCACAAGCCGCACCAGCTATCACGACAGCAGCAACCGCTAATTTAA

CCACAACTGTAACCGTACCACCACTTACTACCACAACGACAAATACGATAGCTCCAACAATCGGGA

CATCCCAGAACAATATTCCGGGCAGCAGCAGTAAGCAACGAGTTATGGACAGTTTTAAGCATTCCA

GAATAGGAACGAAAAGAAAAATAACGACAAACCACATCATAACGTCAAAAACACTAAGCCTTGCT

CGAGCTTGGCCAAAGGGAAATCACCACAGAACAATATCCCAGGCGGCAGCAGTAAACAAACTAAAG

AAAAGGCCGATAGAGAGAAACAAAGGCTGGAGAACTTAGAAATGAAGCGGCAACAGAGGGAACAAG

CGGAGAGGGAGAGGTTACGGGCGGAAAACGAAAGGCGAAGGGAACGGGAAGAAGAAGATGCGCTCG

AGAAAGCAAGGAAGGCTGTAGCGGAGCAGCAACAGCCTATAGCAAGCCAAAGGGTGGAAGAACTGA

GGTCGTCGCCTGGTGAAGGAAGTACATCTCCAGGTTCCTTAAGTTCTGGTTCCGAAAGGATATCGG

AGCGAGAAAGGCAGAGGTTGCAGGAGCAGGAAAGGCGAAGAAGAGAAGTGATGGCCAATAAGATAG

ATATGAACATGCAGAGTGATCTAATGGCTGCTTTCGAAGGTTCGTTATGAACGGTGATAGTCGTGT

GCGTTTGACTGAATATTAAAGATAATAGAAAAAGAGACTCCACGAGCCAATTTTTGTGTATTTAT

GTATTTATATGACAATTTTAATAGGTGTTAAATAAAATGTTAGACGCTCAAAAATTTTTGAAAAAT

GCTTCCATTATGATGAGTTTCGCTTCGGATATATACCTCTGATTTCTTTGAGTTGATCATTTTTTT

GTGTTCGTGGCTTGACTCGATTTTAAATATTTTTTATATATAATATATAAGTTGGACATTTTCAAC

ATGGTTTGTATATATAACACTATAAATTGATTATAAAGTTGTACATAATGATGTTGGGTTGATTAT

TGTGTTAGTTTTTATTTTATTGTCTATTCCTCCTTGTCATTGTTTTATTTTAAAGCATCTTTTGAC

TTTCACGGCTACAGGACGGTCCTAATATGCGGCCCAATCCACTTGCAGATCATTTCAATTATAATA

TTAATATTATTTTAAAATATTTGTACAAAACGAAGAGGAATGTGTTAAATTCAAGTGATCAGCATT

GGATTGTACACCTGTGCACACCTTTAAATTATTGGCGTCAATGTTAGGATGACTCTTTCACATAAA

CCTTGTCCTACACATTGACTTACAGTGGGTATTTAAATTATTAAAGCCACACAGAGAAGATTTTTG

TCTAAAAGGGATTTGTATATGAATTCCAAGGTATATTGAATGTTTATTCACATTTTGTTTCATGAT

CACACTTTAGGATTTAAAAAGGATAGGAAGAAATTGGACTTTTTCATGAAAATATTTAAAATTTTA

CCATATGCATAATATTTGACGATACCACCCATTTCTTGTTGCTTTAAGCTCGACACTAATTGATTT

GATATTTCCTTTTTTCATCAACTTTCAAGATTTTCAAATGCATCAAAATCTGGCTAGTTTGCGGGC

CAGTCGAATATTTTACATATAGATAACGTATGCAGTAAGCGACACGCTACTAGACAAATGGTAGGT

ACCTAATTGCTATGCTTTTGGGCTAATCCGGTCCGTTCTCATGTGACTTTCATGTCTATCGTGTCA

TGTGACTCTAAGCCGCACATCAAAGAAACATGAAATGTAAATCACGTTTCATGGAAGTGAAACACC

GCTAAACAAATAGACGT
```

SEQ ID NO:2 shows the amino acid sequence of an FSH polypeptide encoded by an exemplary WCR fsh DNA, referred to herein in some places as WCR FSH or WCR FSH-1:

MERPPRNEPTVDPVNGVVQPLVQP

-continued

```
DYPPTLESKSAKISTRRESGRQIKKPTRPELDGHPPQPPPLKPKEKLPE

SLKACNEILLELFSKKHSSYAWPFYQPVDAELLGLHDYHDIIKKPMDFS

TVKNKMENREYRTPQDFAADVRLIFSNCYKYNPSDHDVVAMARKLQDVF

EVKYAKIPDEPVNRVGAPAVNNIPAKSETSTSGSSSDSSSDTEDSEEER

RNKQLKLLEKELTAMQEKMRKLVDESSKKKKEKKKDKVKKKPTSGGSLA

NASLSTLPNSSSAGLGKPGAGGHGALNKSNNNNSIAADSVDDSIASVVS

GADLKMAESHHPQTGTGAHHPPAGKSLNMHHNMTANAGANASAQAKTPK

SKGLRGNKPAAATNAAPNKRVKANNKAGAGRKKNAAQPPPMQFDSEDED

NAKPMSYDEKRQLSLDINKLPGDKLGRVVHIIQSREPSLRDSNPDEIEI
```

-continued

```
DFETLKPSTLRELESYVASCLRKKPHKKVAGKSKDEQIAEKKQELEKRL

IDVNDKIGNSKKAPKKDEANKVDPTGAGGPSGRLSSSSSSSDSDSSSSS

LSSSSSDSSDSEAGGTANRQAKKKANKKSPNPSLGSSTTTTTIKVPPPQ

TTATPAPPSQAAPAITTAATANLTTTVTVPPLTTTTTNTIAPTIGTSQN

NIPGSSSKQRVMDSFKHSRIGTKKKNNDKPHHNVKNTKPCSSLAKGKSP

QNNIPGGSSKQTKEKADREKQRLENLEMKRQQREQAERERLRAENERRR

EREEEDALEKARKAVAEQQQPIASQRVEELRSSPGEGSTSPGSLSSGSE

RISERERQRLQEQERRRREVMANKIDMNMQSDLMAAFEGSL
```

SEQ ID NO:3 shows a contig comprising a further exemplary WCR fsh DNA, referred to herein in some places as WCRfsh-2:

```
AGAGAAGCCATTTGTATGACCTCAAAAAGTAAATCTATAATCCTTTGACATCGTAACGGAACTTGT

AAAATCAGCAAATATTTTGAAGTATTTAATAGCACAATCGTATTTAAATCCAATATTTTACAGTAT

TTTTGATATATTTAACTCTTTTTATAAGGCAATATCAGTAATGAAGATTATTTGTTCAGTGCAAGG

CTCTCACACGTCCGCCATCACGACAGTTTGTGGCAAGCTTGGCCAGCGGGTATGTGTTAGGTGAGT

GAGAGTGGTGTAGCTCCGTATTTTTCACGATTCTAATGTGGATTATCACTCAAAAGACGCAGATCC

AAGCTATGATGGCTTTTATCTACTAAGAAACCATTTGTAAAATGGAATGTGATTTGTATCGGCTGA

AGATTATAACCAGCTGATTGGTAGGCCCAGGTCATTATTAACCAAAACTATTTGCGGAGGAAAAAT

GGAACGCCCACCCCGAAACGAACCCACTGTGGACCCAGTGAATGGAGTGGTCCAACCACTAGTCCA

GCCACCTCCAGAGAGTCCGGGCCGCGTCACCAATCAACTTCAGTTTTTACAGAAAACTGTGTTAAA

GGCTGTCTGGAAGCACCAATTCGCTTGGCCCTTCCAGCAACCCGTCGATGCTAGAAAACTCAACTT

GCCCGACTATCATAGGATAATTAAACAGCCAATGGACCTGGGAACAATTAAGAAAAGACTAGACAA

CAATTACTACTGGTCGGGCAAAGAGTGCATCCAAGACTTCAACACGATGTTTACAAACTGCTATGT

CTACAACAAGCCTGGAGAGGATGTTGTTGTCATGGCTCAAACGTTAGAAAAGGTATTTTTGACAAA

AGTGGCGGATATGCCAAAGGAGGAATTTGTTGTTGAATCGCCCGGTAAAGCGGGAGCGGCAAAAGG

AAAGAAGGGGCGGACCAGTACAGCGGGCGCTGTCAGTGCACCCCCAACACCAACTACAGCCACCGC

TGGTTCGGGAGGCAGGGGTAGGCCTCCCGCCACTGTCTCTTCTACAAGCGCCACTCCAGTTGCTAC

CACTACAGGATCTTCAGGGTTACCTTTAGGCACTCAAGCACCGGCTACAGTACCTGGCAGCACCGC

AACTACCACCATAGCGGCGGCCAGCACCAACAACAGCTCTCTGTCGAATCAGCAACTGAACTCTTC

TTCCAGTTCCATTCACGGAAGCGGCTCCAGTTTAGGAAATTCCTTAGATTCCAGCAGCGTCATGCC

TGCCAACGTTATACCTCCGGCACAACCAGCCAAGGTAAAAAAGGGCGTGAAAAGAAAGGCCGATAC

TACGACGCCTGCTACAGCCTACGATTATCCGCCAACTTTGGAGTCGAAGTCTGCAAAGATATCGAC

GCGCCGAGAGTCCGGTAGGCAAATCAAAAAGCCCACCAGGCCAGAACTGGACGGTCATCCGCCACA

ACCCCCTCCACTTAAACCAAAAGAAAAACTACCAGAATCACTGAAAGCCTGCAATGAAATCCTCCT

AGAATTGTTCTCTAAGAAACATTCTAGTTACGCCTGGCCTTTTTATCAACCCGTAGACGCAGAATT

ACTCGGTCTGCACGACTACCACGACATCATAAAGAAACCGATGGATTTTAGTACTGTAAAAAATAA

AATGGAAACCGAGAGTATCGCACTCCTCAAGACTTTGCCGCCGACGTTAGACTGATTTTTAGTAA

TTGTTACAAGTACAACCCTTCTGACCACGATGTGGTTGCTATGGCGAGGAAGTTGCAGGATGTGTT

TGAAGTGAAATATGCAAAGATTCCCGATGAACCTGTCAATAGGGTAGGAGCCCCTGCCGTTAATAA

TATACCTGCCAAATCAGAAACGAGTACATCCGGTTCCAGTTCGGATTCTTCTAGCGACACGGAAGA

TTCGGAGGAAGAAAGGCGAAACAAACAACTGAAGCTGCTAGAAAAAGAGTTGACGGCAATGCAAGA
```

-continued

```
AAAAATGCGTAAATTGGTAGACGAGAGCTCGAAAAAGAAAAAAGAAAAGAAAAAGGACAAAGTGAA
AAAGAAACCGACATCAGGTGGGTCTCTGGCGAACGCCTCACTATCAACTCTACCGAACAGCAGCAG
CGCGGGCTTGGGACTCCGCGGCAATAAACCCGCTGCAGCTACCAACGCGGCTCCCAACAAGAGGGT
CAAAGCCAACAACAAAGCTGGTGCGGGTAGGAAGAAGAACGCAGCACAACCACCACCTATGCAGTT
CGATTCTGAGGACGAAGACAACGCCAAACCGATGTCTTACGACGAGAAACGGCAGTTGTCTTTGGA
TATTAATAAATTACCAGGTGACAAATTGGGTAGAGTTGTACATATAATCCAATCCAGGGAACCGTC
GTTGAGGGATTCCAATCCTGACGAAATCGAGATCGATTTCGAAACGCTGAAACCCTCAACACTCAG
AGAATTAGAGAGTTACGTTGCGTCGTGTCTTCGCAAAAAGCCACGTAAGCCATACTATAAAAAAGT
AGCGGGCAAATCTAAGGACGAACAAATAGCGGAGAAGAAGCAAGAGTTAGAGAAAAGACTAATAGA
CGTAAACGATAAAATCGGCAACTCCAAGAAGGCCCCCAAAAAAGATGAAGCCAACAAGGTAGACCC
AACGGGCGCGGGAGGTCCCTCAGGCCGCCTATCCTCTAGTTCCAGCAGTTCGGACTCCGACAGCAG
TAGTAGCAGTTTGTCCTCTAGTTCTAGCGACTCCAGTGACAGTGAAGCAGGTGGGACGGCGAACCG
GCAGGCCAAAAAGAAAGCGAATAAAAAATCACCCAATCCTTCTCTAGGCAGTTCCACCACCACTAC
GACTATAAAAGTGCCGCCGCCTCAAACGACGGCAACACCTGCACCGCCGTCACAAGCCGCACCAGC
TATCACGACAGCAGCAACCGCTAATTTAACCACAACTGTAACCGTACCACCACTTACTACCACAAC
GACAAATACGATAGCTCCACCAATTCAACCGGCGCCAGTTCCAAACGTCGCAGTTCCCGCGCAAAC
GACGCCAGCCGCACCCGCCTTCACGCCGAGCATAACCATCAAACCATCACTACAGGCCGCCCCTAT
CGCTCCGACGGTGCCGCCTCTTATCAAGTCAATCGAGAAACTGCCTGTCACAACTCTCTTACCTCC
TACCGTTCCTACGATAACGCCTCCAACAGTACCTCAAGCTCCCAAATCGGTAGCGCTACCGACTCC
TTCTCCTGATAAACCTAAACCTAACATTATTTCTCCCATTGGTACCTTTACCGACCCTATCGAACA
ATCATTGGCTAGTCTTGAACACGATATTAAGCAGAATGATCCTATGGACGTCATTACGGCGTCTAC
TATGATGCAAATGCCTACTACACTAACCAATCCTATCGTGTCACATCCACATCCTAACTTAAACTT
AAATCCCACCATTAACCATCCTATTTTACAGCCTAGCACACTTAGTATGGACTTAAAAGCGCCTAT
TATGGGCACTATGGCGCCGAGCAATACCATGTTGCATCACGGATTGCAACAAGCAATGGAAACGGA
TATCAGTATACCTCCACCCCCCACCAACATGCTGCATGGACAGAACAACGGTTTTGGCATGAAACA
CAATTTTGATCTGACTACAAACAACAACGGTCTTTCCTCGATGGGTCTGCCCATGGAAATGTCGAT
ATCGTCAATGTTTGATCCAATTCCACAAAATATTAATCCCATGATGAAGAACGATTCCCAACTCAA
GATGGACGATCGCATGGATACCTTAGGTGGACTTTTGAACGACAAGAAGTCCAATCTCCTCATACA
AAAGCCGATGTCGCAGTCGTTTGGTTTCAAGAATGACAAACCAGATCATAACGTCAAAAACGCTAG
TTCCTGGTCGAGTTTGGCCAAAGGAAAATCACCACAAACAATATTCCGGGCGGCAGCAGTAAACA
ACAAGTTATGGATAGTTTTAAGGCATTCCAAAATAAAGCTAAAGAAAAGGCCGATAGAGAGAAACA
AAGGCTGGAGAACTTAGAAATGAAGCGGCAACAGAGGGAACAAGCGGAGAGGGAGAGGTTACGGGC
GGAAAACGAAAGGCGAAGGGAACGGGAAGAAGAAGATGCGCTCGAGAAAGCAAGGAAGGCTGTAGC
GGAGCAGCAACAGCCTATAGCAAGCCAAAGGGTGGAAGAACTGAGGTCGTCGCCTGGTGAAGGAAG
TACATCTCCAGGTTCCTTAAGTTCTGGTTCCGAAAGGATATCGGAGCGAGAAAGGCAGAGGTTGCA
GGAGCAGGAAAGGCGAAGAAGAGAAGTGATGGCCAATAAGATAGATATGAACATGCAGAGTGATCT
AATGGCTGCTTTCGAAGGTTCGTTATGAACGGTGATAGTCGTGTGCGTTTGACTGAATATTAAGA
TAATAGAAAAGAGACTCCACGAGCCAATTTTTTGTGTATTTATGTATTTATATGACAATTTTAAT
AGGTGTTAAATAAAATGTTAGACGCTCAAAAATTTTTGAAAAATGCTTCCATTATGATGAGTTTCG
```

-continued

CTTCGGATATATACCTCTGATTTCTTTGAGTTGATCATTTTTTTGTGTTCGTGGCTTGACTCGATT

TTAAATATTTTTTATATATAATATATAAGTTGGACA

SEQ ID NO:4 shows the amino acid sequence of a further FSH polypeptide encoded by an exemplary WCRfsh DNA, referred to herein in some places as WCR FSH or WCR FSH-2:

MERPPRNEPTVDPVNGVVQPLVQPPPESPGRVTNQLQFLQKTVLKAVWK
HQFAWPFQQPVDARKLNLPDYHRIIKQPMDLGTIKKRLDNNYYWSGKEC
IQDFNTMFTNCYVYNKPGEDVVVMAQTLEKVFLTKVADMPKEEFVVESP
GKAGAAKGKKGRTSTAGAVSAPPTPTTATAGSGGRGRPPATVSSTSATP
VATTTGSSGLPLGTQAPATVPGSTATTTIAAASTNNSSLSNQQLNSSSS
SIHGSGSSLGNSLDSSSVMPANVIPPAQPAKVKKGVKRKADTTTPATAY
DYPPTLESKSAKISTRRESGRQIKKPTRPELDGHPPQPPPLKPKEKLPE
SLKACNEILLELFSKKHSSYAWPFYQPVDAELLGLHDYHDIIKKPMDFS
TVKNKMENREYRTPQDFAADVRLIFSNCYKYNPSDHDVVAMARKLQDVF
EVKYAKIPDEPVNRVGAPAVNNIPAKSETSTSGSSSDSSSDTEDSEEER
RNKQLKLLEKELTAMQEKMRKLVDESSKKKKEKKKDKVKKKPTSGGSLA
NASLSTLPNSSSAGLGLRGNKPAAATNAAPNKRVKANNKAGAGRKKNAA
QPPPMQFDSEDEDNAKPMSYDEKRQLSLDINKLPGDKLGRVVHIIQSRE
PSLRDSNPDEIEIDFETLKPSTLRELESYVASCLRKKPRKPYYKKVAGK
SKDEQIAEKKQELEKRLIDVNDKIGNSKKAPKKDEANKVDPTGAGGPSG
RLSSSSSSSDSDSSSSLSSSSSDSSDSEAGGTANRQAKKKANKKSPNP
SLGSSTTTTTIKVPPPQTTATPAPPSQAAPAITTAATANLTTTVTVPPL
TTTTTNTIAPPIQPAPVPNVAVPAQTTPAAPAFTPSITIKPSLQAAPIA
PTVPPLIKSIEKLPVTTLLPPTVPTITPPTVPQAPKSVALPTPSPDKPK
PNIISPIGTFTDPIEQSLASLEHDIKQNDPMDVITASTMMQMPTTLTNP
IVSHPHPNLNLNPTINHPILQPSTLSMDLKAPIMGTMAPSNTMLHHGLQ
QAMETDISIPPPPTNMLHGQNNGFGMKHNFDLTTNNNGLSSMGLPMEMS
ISSMFDPIPQNINPMMKNDSQLKMDDRMDTLGGLLNDKKSNLLIQKPMS
QSFGFKNDKPDHNVKNASSWSSLAKGKSPQNNIPGGSSKQQVMDSFKAF
QNKAKEKADREKQRLENLEMKRQQREQAERERLRAENERRREREEEDAL
EKARKAVAEQQQPIASQRVEELRSSPGEGSTSPGSLSSGSERISERERQ
RLQEQERRRREVMANKIDMNMQSDLMAAFEGSL

SEQ ID NO:5 shows an exemplary WCRfsh DNA, referred to herein in some places as WCR fsh-1 reg1 (region 1), which is used in some examples for the production of a dsRNA:

TCTTCCGTGTCGCTAGAAGAATCCGAACTGGAACCGGATGTACTCGTT

TCTGATTTGGCAGGTATATTATTAACGGCAGGGGCTCCTACCCTATTG

ACAGGTTCATCGGGAATCTTTGCATATTTCACTTCAAACACATCCTGC

AACTTCCTCGCCATAGCAACCACATCGTGGTCAGAAGGGTTGTACTTG

TAACAATTACTAAAAATCAGTCTAACGTCGGCGGCAAAGTCTTGAGGA

GTGCGATACTCTCGGTTTTCCATTTTATTTTTTACAGTACTAAAATCC

ATCGGTTTCTTTATGATGTCGTGGTAGTCGTGCAGACCGAGTAATTCT

GCGTCTACGGGTTGATAAAAAGGCCAGGCGTAACTAGAATGTTTCTTA

GAGAACAATTCTAGGAGGATTTCATTGCAGGCTTTCAGTGATTCTGGT

AGTTTTTCTTTTG

SEQ ID NO:6 shows a further exemplary WCRish DNA, referred to herein in some places as WCRish-2 reg1 (region 1), which is used in some examples for the production of a dsRNA:

ACTTCCTCGCCATAGCAACCACATCGTGGTCAGAAGGGTTGTACTTGTA

ACAATTACTAAAAATCAGTCTAACGTCGGCGGCAAAGTCTTGAGGAGTG

CGATACTCTCGGTTTTCCATTTTATTTTTTACAGTACTAAAATCCATCG

GTTTCTTTATGATGTCGTGGTAGTCGTGCAGACCGAGTAATTCTGCGTC

TACGGGTTGATAAAAAGGCCAGGCGTAACTAGAATGTTTCTTAGAGAAC

AATTCTAGGAGGATTTCATTGCAGGCTTTCAGTGATTCTGGTAGTTTTT

CTTTTGGTTTAAGTGGAGGGGGTTGTGGCGGATGACCGTCCAGTTCTGG

CCTGGTGGGCTTTTTGATTTGCCTACCGGACTCTCGGCGCGTCGATATC

TTTGCAGACTTCGACTCCAAAGTTGGCGGATAATCGTAGGCTGTAGCAG

GCGTCGTAGTATCGGCCTTTCTTTTCACGCCCTTTTTTACC

SEQ ID NO:7 shows a further exemplary WCRish DNA, referred to herein in some places as WCR fsh-1 v1 (version 1), which is used in some examples for the production of a dsRNA:

GTTCATCGGGAATCTTTGCATATTTCACTTCAAACACATCCTGCAACTT

CCTCGCCATAGCAACCACATCGTGGTCAGAAGGGTTGTACTTGTAACAA

TTACTAAAAATCAGTCTAACGTCGGCGGCAAAGTCTTGAGGAGTG

SEQ ID NO:8 shows a further exemplary WCRish DNA, referred to herein in some places as WCR fsh-1 v2 (version 2), which is used in some examples for the production of a dsRNA:

ACTTCCTCGCCATAGCAACCACATCGTGGTCAGAAGGGTTGTACTTGTA

ACAATTACTAAAAATCAGTCTAACGTCGGCGGCAAAGTCTTGAGGAGTG

CGATACTCTCGGTTTTCCATTTTATTTTTTACAGTACTAAAATCCATCG

GTTTCTTTATGATGTCG

SEQ ID NO:9 shows the nucleotide sequence of T7 phage promoter.

SEQ ID NO:10 shows a fragment of an exemplary YFP coding region.

SEQ ID NOs:11-18 show primers used to amplify portions of exemplary WCR fsh sequences comprising fsh-1 reg1, fsh-2 reg1, fsh-1 v1, and fsh-1 v2, used in some examples for dsRNA production.

SEQ ID NO:19 shows an exemplary YFP gene.

SEQ ID NO:20 shows a DNA sequence of annexin region 1.

SEQ ID NO:21 shows a DNA sequence of annexin region 2.

SEQ ID NO:22 shows a DNA sequence of beta spectrin 2 region 1.

SEQ ID NO:23 shows a DNA sequence of beta spectrin 2 region 2.

SEQ ID NO:24 shows a DNA sequence of mtRP-L4 region 1.

SEQ ID NO:25 shows a DNA sequence of mtRP-L4 region 2.

SEQ ID NOs:26-53 show primers used to amplify gene regions of annexin, beta spectrin 2, mtRP-L4, and YFP for dsRNA synthesis.

SEQ ID NO:54 shows a maize DNA sequence encoding a TIP41-like protein.

SEQ ID NO:55 shows the nucleotide sequence of a T2OVN primer oligonucleotide.

SEQ ID NOs:56-60 show primers and probes used for dsRNA transcript expression analyses in maize.

SEQ ID NO:61 shows a nucleotide sequence of a portion of a SpecR coding region used for binary vector backbone detection.

SEQ ID NO:62 shows a nucleotide sequence of an AAD1 coding region used for genomic copy number analysis.

SEQ ID NO:63 shows the DNA sequence of a maize invertase gene.

SEQ ID NOs:64-72 show the nucleotide sequences of DNA oligonucleotides used for gene copy number determinations and binary vector backbone detection.

SEQ ID NOs:73-75 show primers and probes used for dsRNA transcript maize expression analyses.

SEQ ID NO:76 shows an exemplary Neotropical Brown Stink Bug (*Euschistus heros*) fill DNA, referred to herein in some places as BSB fsh-1:

```
AGAATACAAAACAGCAACTGAATTTGCTGCTGATGTGAGACTAATTTTT
ACAAATTGTTACAAGTATAATCCCCCGGACCATGATGTTGTTGCAATGG
GCCGAAAATTGCAGGATGTTTTTGAAGTGAGTTAAGAATCATGCAGGAA
GAGATGAGAAAACTCGTCGAAGAAGGAACTGTTAAAAAGAAGAAGAAA
AGAAAGAAGGTTCAGGTTCTGGTGGAAGTTCTTCTAGTAAGAAACGAA
ATCTGCTGATAGGACATTAGGTAAAACAGCCGATGGTGGGCTTATAGCT
GGTGCCGGAGCACCCGCTATCATGGAAATAAAGGCTACTGATGGCGTAA
AGGCTGTCCCTCCTCCAGGCAGGAATGCAGTCCCTTCACCCCAGGTCAA
ACCAAACAAGGGCAAAGCCCCTGGAAGGGCACCAGGAAAAACCAATTCT
CAGGGTAAGAGGCCAAAGCCGAACTCCAGGTCTACTAACTCTAAGAAGA
AGAATCCTGTTGTCACTTCAGAGTTTAACTCGGAAGATGAGGATAATGC
AAAGCCTATGTCTTATGATGAAAAGAGACAACTTAGCTTGGATATTAAC
AAGCTACCAGGTGATAAACTTGGAAGAGTAGTCCATATCATTCAGGCCA
GAGAGCCCTCTTTGAGGGATTCAAACCCTGATGAAATTGAAATAGACTT
TGAGACATTGAAGCCATCAACCCTGAGGGAGCTCGAGTCCTACGTTGCA
TCATGTCTCAGGAAAAAGCCACATAAGAAAAATGTATCAGACAAAAATC
AAAAAGATGAAGCGATGGCCG
```

SEQ ID NO:77 shows the amino acid sequence of a BSB FSH polypeptide encoded by an exemplary BSB fsh DNA (i.e., BSB fsh-1):

```
SELRIMQEEMRKLVEEGTVKKKKKKKEGSGSGGSSSKKRKSADRTLGK
TADGGLIAGAGAPAIMEIKATDGVKAVPPPGRNAVPSPQVKPNKGKAPG
RAPGKTNSQGKRPKPNSRSTNSKKKNPVVTSEFNSEDEDNAKPMSYDEK
RQLSLDINKLPGDKLGRVVHIIQAREPSLRDSNPDEIEIDFETLKPSTL
RELESYVASCLRKKPHKKNVSDKNQKDEAMA
```

SEQ ID NO:78 shows a further exemplary BSB fsh DNA, referred to herein in some places as BSB fsh-2:

```
TGTAAATGTTCCCATCCATTATTTCGGTATATTGATGTATACCGTTTTA
GGCTCAGCCTTATTGGCTTCTTCCCGAGTGGGGAGCCCGCCATGTTGAC
CAACTAAGCGCCAAAAGAGGAGCTTTTTTGGTATTTTTTCTCTTTGTTT
AGGTAAAAAAATAGTTAAGTATTGTTAAATTGATGTTAGGGTTACGTTA
CGAATGATCTTGAAGTGGTGATGTGGTTACTCCCCCTTTCGAGTACAGT
AGCTTAACCAAGCTTGTGTTGGGCTTGAGCTTCTCTCGTCTTCTGTAGC
TTTACTTTACGTTTATTACTGGATAAAGTGAAAAATAAGTGTTAAATAC
AAGTGTGTGGACTCCAGGAAGGGATTTTGTGCTAAATGAAATAGTTTTT
TGTTTAATAACAGTGATTTTGGATCGTTTTTAAAGGTAGTGTGAAATGC
GGTTTGTTATTCTCAGGAGTATCCCCGAGGCCACATCCAAAATTCAATT
TTTTTCTTCAAAGTTTCCCCTTGAAGGTTCTGTTATGACTAATATACTC
AAGTAAATTGTTATCTTGTTGTTCCTTAAATTAGGACTAATGATATGGG
GAGTAGTTTTAACTAAGCATTTCTGTATGCCATTTTTATGAGTAAAGCA
ATGTAAGGTTATTGAGATTTAAATGTTCCTGTAAGATCATGATTTCATC
TTATTGTCTTACTCAGATGCGTCTGCATTGGGCTTTTTTACAGTACTAA
TGAAAACCTCAGTGACAATCGATCCTTGGAAAGGAGTGTGGCCAAAATG
CAACAAATGGACTCCTTGCAACCTAACAACGCAACAGGACTGGTGAAAA
GCGGACTAGAGGCGGGGCCGGTAGCGGCATGAAGGAGCCCCCGCCACG
AGAGGAGCCGGTCCTAGACCCAATCAATGGTGTTGTCCAGCCTCCGGTC
ATACCTCCTCCCCACAGGCCTGGCCGAGTAACCAACCAATTGCAATATA
TTCAGAAAAATGTCCTTAAAGCAGTCTGGAAACATCAATATGCTTGGCC
TCTACAGCAACCTGTCGATGCTAATAAACTCAATCTTCCTGATTACCAT
AAAGTTATTAAACATCCAATGGATCTTGGTACTATCAAAAAACGACTGG
AAAACAATTATTATTGGTGTGGTGCTGAGTGTATTCAAGATTTCAACAC
AATGTTTAACAATTGTTATGTTTATAACAAACCAGGAGAAGATGTTGTT
GTTATGGCTCAAACGCTGGAAAAACTTTATTTGCAAAAGCTGGAAACAA
TGCCCAAAGAGGAAATTGAGCTTGAGCCTCCACCACCTAAAGGTTCTAA
```

```
GCCAGTTAAGAAGCGACCTGGAGTTATAGGTCCAGGTAGAGGGGCGGG
ACCACTGGCGCAGGAAGAGGGAGGCCTTCCAATTCAACGCCAGCAGCTG
CGGCAGTAGTCACCACTCCTGTACCTCCTGTCACTCCCCATCACACCT
TCCAGCAACCATACCTGGTTCGACTGCTACTACCACTGTACCTACTACT
CACCATAACTCTCTCCCCCCTCAGGTTGGGCAGCCAGCAGCTGTACCCT
CCAACTTCAGTACAACTACTGTTGATCCCCTTTTAACACCTGGATTGGC
TCCTGGTGTTGGTCCAAAAGGTGGCAAAGGGGCCGTCGTCCAGACCCCA
ACGGCGCCCAAACCGAAAAAGGGGTCAAAAGAAAGGCTGATCTAGCGA
ATGATAGCCCCGCTAGTTTTGACCCAACATACACCCCAGGTGACTCCAA
AGCTGCCAAGGTTGGCACTAGGAGAGAATCTGGAAGGCAAATTAAAAAG
CCTCAAAGACAGTCAGACGATGGTATGCCATTTTCTCAAAGCCCAATGG
CACCTTATTCACTTTCAAATTCAACGCAGGCTGCCCATGAAAAGCCGAA
AGAAAAACTCTCTGAAACATTAAAAGCATGTAATGAAATATTGAAGGAG
TTATTTTCTAAAAAACATTTTAATTATGCTTGGCCCTTCTATAAACCTG
TTGATGCCGAATGGCTAGGTTTACATGACTACCATGATATTATTAAGAA
ACCTATGGATCTCGGAACTGTAAAGCAAAAAATGGACAATCGAGAATAC
AAAACAGCAACTGAATTTGCTGCTGATGTGAGACTAATTTTTACAAATT
GTTACAAGTATAATCCCCCGGACCATGATGTTGTTGCAATGGGCCGAAA
ATTGCAGGATGTTTTTGAAGTGAGATTCGCTCAAGTACCTGAAGACTCC
CCTATATCGACTGTTCCTGAAAAGGAAGAAGAATCCACCTCTGGGTCAT
CGTCTGGCTCTGAATCCGAAACAGATAATTCAGATGACGAAAGGGCCCG
TAAACTTAGTCAATTACAAGAGCAGTTAAGAATCATGCAGGAAGAGATG
AGAAAACTCGTCGAAGAAGGAACTGTTAAAAAGAAGAAGAAAAAGAAAG
AAGGTTCAGGTTCTGGTGGAAGTTCTTCTAGTAAGAAACGGAAATCTGC
TGATAGGACATTAGGTAAAACAGCCGATGGTGGGCTTATAGCTGGTGCC
GGAGCACCCGCTATCATGGAAATAAAGGCTACTGATGGCGTAAAGGCTG
TCCCTCCTCCAGGCAGGAATGCAGTCCCTTCACCCCAGGTCAAACCAAA
CAAGGGCAAAGCCCTGGAAGGGCACCAGGAAAAACCAATTCTCAGGGT
AAGAGGCCAAAGCCGAACTCCAGGTCTACTAACTCTAAGAAGAAGAATC
CTGTTGTCACTTCAGAGTTTAACTCGGAAGATGAGGATAATGCAAAGCC
TATGTCTTATGATGAAAAGAGACAACTTAGCTTGGATATTAACAAGCTA
CCAGGTGATAAACTTGGAAGAGTAGTCCATATCATTCAGGCCAGAGAGC
CCTCTTTGAGGGATTCAAACCCTGATGAAATTGAAATAGACTTTGAGAC
ATTGAAGCCATCAACCCTGAGGGAGCTCGAGTCCTACGTTGCATCATGT
CTCAGGAAAAGCCACGTAAGCCCTACAATAAGAAAAATGTATCAGCAA
AATCAAAAGATGAAGCGATGGCCGAGAAGAAACAAGAGCTAGAAAAAG
GCTTCAGGATGTTACTGGTCAATTGGGAGGATCAGCTAAGAAAACAGCT
AAAAAACAAGGTCAGGGAAGGCTTTCAGCGTCATCGTCATCAAGCTCAG
ATTCTGATACAAGTAGTTCAAGTCTCTCTAGCAGTTCTTCCGACTCATC
TGATAGCGAAGCAGGGAAGGCAGGGCGTCCACCGAGGAAGAAAAATAAG
AAAAATCACCAAATAGCAACAACTGCTGCAACAACTGTCCAACAGAATC
AAACTGTACCAAGCTTGACCATGACAACTGCCACTGGTACTATTGTAAA
TAAAAATGCTGGGGCTCCACAGCCCGTAGTACCGTTAGCAAGCACCAAC
AAACCTACTGTACCTCCGGTCTCTGCAGTGACACAGCCTGAACCTGTGA
AACCTGTTGTAGCATCACATAGCTTGCCTCCCCAACCTGCGAGGCCTAC
CGCAACGGCTGCCCCTCTGACAACTGCTAAGAGGGCGTCAATCCCCACG
CCAGCGACATCGATGGGCATACCTCCGCCTGCTCCGACTGGTCTTGAAA
CAGGTCCTATTGAGATCAAACAGGAATTGGATGTTCCTGTTCCACTAGC
ACCCGTTCCAGATCATTTGGATTTCAAAAACCTTTTGGAGGTGAAGCCC
GAGCTAAATGATATCGTTACTGGGATGCCTTCTGTATTTGATCCTTTGC
CTGACTCACCTCCCATCATTAAGGAAGAAAAGCATCCTATACTCCCCCA
TCACACAGATGGACACTTGAACAATTCTCTTCCCCCTGTCAGCAACGTA
CCTGGTCCGCCAATCATACCGAGTGCTGCACTTCCAACTACACCACATC
ACTTAGATATGAATAAGAATTCCCAGCCTCCTCAGCTTCCCCAGACGCC
AACTTTACAACACCCCTTCAAACCTAAGAATTTTGGCTTCAACATTGAT
GGCTGCTTAAGGATTTCAAAGACTGTTGAGCAGAACTTGAAAAATGCCA
GTTCATGGTCTTCACTTGCCCAGTCCCCAACACCAGCTCTCACCCCAAC
TCCACCGACTGCGGCTCTGAAGTCCTCCATGGCTGACAGCTTTCAAGCT
TTTAAGAAACAAGCTAAAGAAAATGCCAAGAAGCAACGAGCCCTGATTG
AACAGCAAGAAATGAGGCGACATCAAAAAGAACAGGCTGAAAGGGAAAG
ATTACGTGTTGAAACCGAAAAGAGGAGAGAAAGAGAAGAAGAAGAAGCT
CTGGAGAAGGCTAGAAATAGTTATGTCGGGAACAGGAAGGCTGCTGTAG
TGGCTTCTGGAAGAGTTGAAGAGGTTAAAAATGCTGCTATCGAGGAAGG
TACCAGCCCAGGTTCGGCAGACAAAGCTGCTGCAGAGCGAGAACGTCTA
AGGCAACGAGAGCAAGAGAGGCGGCGAAGAGAAGCATTGGCTGGGCAAA
TTGATATGAACAGGCAAAGTGATTTAATGGCTGCTTTTGAACAGACCTT
GTAATTCTTCAAGGGCAGTTTTTGTGTTTTCTTTTCTTTCTTTTTTTTA
A
```

SEQ ID NO:79 shows the amino acid sequence of a further BSB FSH polypeptide encoded by an exemplary BSB fsh DNA (i.e BSB fsh-2):

```
VAKMQQMDSLQPNNATGLVKSGLEAGAGSGMKEPPPREEPVLDPINGVV
QPPVIPPPHRPGRVTNQLQYIQKNVLKAVWKHQYAWPLQQPVDANKLNL
PDYHKVIKHPMDLGTIKKRLENNYYWCGAECIQDFNTMFNNCYVYNKPG
EDVVVMAQTLEKLYLQKLETMPKEEIELEPPPPKGSKPVKKRPGVIGPG
RGGGTTGAGRGRPSNSTPAAAAVVTTPVPPVTPPSHLPATIPGSTATTT
VPTTHHNSLPPQVGQPAAVPSNFSTTTVDPLLTPGLAPGVGPKGGKGAV
VQTPTAPKPKKGVKRKADLANDSPASFDPTYTPGDSKAAKVGTRRESGR
QIKKPQRQSDDGMPFSQSPMAPYSLSNSTQAAHEKPKEKLSETLKACNE
ILKELFSKKHFNYAWPFYKPVDAEWLGLHDYHDIIKKPMDLGTVKQKMD
NREYKTATEFAADVRLIFTNCYKYNPPDHDVVAMGRKLQDVFEVRFAQV
```

-continued
PEDSPISTVPEKEEESTSGSSSGSESETDNSDDERARKLSQLQEQLRIM

QEEMRKLVEEGTVKKKKKKKEGSGSGGSSSSKKRKSADRTLGKTADGGL

IAGAGAPAIMEIKATDGVKAVPPPGRNAVPSPQVKPNKGKAPGRAPGKT

NSQGKRPKPNSRSTNSKKKNPVVTSEFNSEDEDNAKPMSYDEKRQLSLD

INKLPGDKLGRVVHIIQAREPSLRDSNPDEIEIDFETLKPSTLRELESY

VASCLRKKPRKPYNKKNVSAKSKDEAMAEKKQELEKRLQDVTGQLGGSA

KKTAKKQGQGRLSASSSSSSDSDTSSSSLSSSSSDSSDSEAGKAGRPPR

KKNKKNHQIATTAATTVQQNQTVPSLTMTTATGTIVNKNAGAPQPVVPL

ASTNKPTVPPVSAVTQPEPVKPVVASHSLPPQPARPTATAAPLTTAKRA

SIPTPATSMGIPPPAPTGLETGPIEIKQELDVPVPLAPVPDHLDFKNLL

EVKPELNDIVTGMPSVFDPLPDSPPIIKEEKHPILPHHTDGHLNNSLPP

VSNVPGPPIIPSAALPTTPHHLDMNKNSQPPQLPQTPTLQHPFKPKNFG

FNIDGCLRISKTVEQNLKNASSWSSLAQSPTPALTPTPPTAALKSSMAD

SFQAFKKQAKENAKKQRALIEQQEMRRHQKEQAERERLRVETEKRRERE

EEEALEKARNSYVGNRKAAVVASGRVEEVKNAAIEEGTSPGSADKAAAE

RERLRQREQERRRREALAGQIDMNRQSDLMAAFEQTL

SEQ ID NO:80 shows an exemplary BSB fsh DNA, referred to herein in some places as BSB_fsh-1 reg1 (region 1), which is used in some examples for the production of a dsRNA:

GCCCCTGGAAGGGCACCAGGAAAAACCAATTCTCAGGGTAAGAGGCCAA

AGCCGAACTCCAGGTCTACTAACTCTAAGAAGAAGAATCCTGTTGTCAC

TTCAGAGTTTAACTCGGAAGATGAGGATAATGCAAAGCCTATGTCTTAT

GATGAAAAGAGACAACTTAGCTTGGATATTAACAAGCTACCAGGTGATA

AACTTGGAAGAGTAGTCCATATCATTCAGGCCAGAGAGCCCTCTTTGAG

GGATTCAAACCCTGATGAAATTGAAATAGACTTTGAGACATTGAAGCCA

TCAACCCTGAGGGAGCTCGAGTCCTACGTTGCATCATGTCTCAGGAAAA

AGCCACATAAGAAAAATGTATCAG

SEQ ID NO:81 shows an exemplary BSB fsh DNA, referred to herein in some places as BSB_fsh-2 reg1 (region 1), which is used in some examples for the production of a dsRNA:

ACAGTCAGACGATGGTATGCCATTTTCTCAAAGCCCAATGGCACCTTAT

TCACTTTCAAATTCAACGCAGGCTGCCCATGAAAAGCCGAAAGAAAAAC

TCTCTGAAACATTAAAAGCATGTAATGAAATATTGAAGGAGTTATTTTC

TAAAAAACATTTTAATTATGCTTGGCCCTTCTATAAACCTGTTGATGCC

GAATGGCTAGGTTTACATGACTACCATGATATTATTAAGAAACCTATGG

ATCTCGGAACTGTAAAGCAAAAAATGGACAATCGAGAATACAAAACAGC

AACTGAATTTGCTGCTGATGTGAGACTAATTTTTACAAATTGTTACAAG

TATAATCCCCCGGACCATGATGTTGTTGCAATGGGCCGAAAATTGCAGG

ATGTTTTTGAAGTGAGATTCGCTCAAGTACCTGAAGAC

SEQ ID NOs:82-85 show primers used to amplify portions of exemplary BSB fsh sequences comprising fsh-1 reg1 used in some examples for dsRNA production.

SEQ ID NO:86 shows an exemplary YFP v2 DNA, which is used in some examples for the production of the sense strand of a dsRNA.

SEQ ID NOs:87-88 show primers used for PCR amplification of YFP sequence YFP v2, used in some examples for dsRNA production.

SEQ ID NOs:89-98 show exemplary RNAs transcribed from nucleic acids comprising exemplary fsh polynucleotides and fragments thereof.

SEQ ID NO:99 shows an oligonucleotide probe used for dsRNA transcript expression analyses in maize.

SEQ ID NO:100 shows an exemplary linker polynucleotide, the polyribonucleotide encoded by which forms a "loop" in a hpRNA molecule.

SEQ ID NO:101 shows the loop polyribonucleotide encoded by SEQ ID NO:100.

DETAILED DESCRIPTION

I. Overview of Several Embodiments

We developed RNA interference (RNAi) as a tool for insect pest management, using one of the most likely target pest species for transgenic plants that express dsRNA; the western corn rootworm. Thus far, most genes proposed as targets for RNAi in rootworm larvae do not actually achieve their purpose. Herein, we describe RNAi-mediated knock-down offsh in the exemplary insect pests, western corn rootworm and neotropical brown stink bug, which is shown to have a lethal phenotype when, for example, iRNA molecules are delivered via ingested or injectedfsh dsRNA. In embodiments herein, the ability to deliverfsh dsRNA by feeding to insects confers an RNAi effect that is very useful for insect (e.g., coleopteran and hemipteran) pest management. By combining fsh-mediated RNAi with other useful RNAi targets (e.g., ROP RNAi targets, as described in U.S. patent application Ser. No. 14/577,811, RNA polymerase 11 RNAi targets, as described in U.S. Patent Application No. 62/133,214, RNA polymerase 11140 RNAi targets, as described in U.S. patent application Ser. No. 14/577,854, RNA polymerase 112 15 RNAi targets, as described in U.S. Patent Application No. 62/133,202, RNA polymerase 1133 RNAi targets, as described in U.S. Patent Application No. 62/133,210), ncm RNAi targets, as described in U.S. Patent Application No. 62/095487), snap25 RNAi targets, as described in U.S. Patent Application No. 62/193502), transcription elongation factor spt5 RNAi targets, as described in U.S. Patent Application No. 62/168613), and transcription elongation factor spt6 RNAi targets, as described in U.S. Patent Application No. 62/168606), the potential to affect multiple target sequences, for example, in rootworms (e.g., larval rootworms) and with multiple modes of action, may increase opportunities to develop sustainable approaches to insect pest management involving RNAi technologies.

Disclosed herein are methods and compositions for genetic control of insect (e.g., coleopteran and/or hemipteran) pest infestations. Methods for identifying one or more gene(s) essential to the lifecycle of an insect pest for use as a target gene for RNAi-mediated control of an insect pest population are also provided. DNA plasmid vectors encoding an RNA molecule may be designed to suppress one or more target gene(s) essential for growth, survival, and/or development. In some embodiments, the RNA molecule may be capable of forming dsRNA molecules. In some embodiments, methods are provided for post-transcriptional repression of expression or inhibition of a target gene via nucleic acid molecules that are complementary to a coding or non-coding sequence of the target gene in an insect pest. In these and further embodiments, a pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, shRNA, miRNA and/or hpRNA that is complementary to coding and/or non-coding sequences of the target gene(s) to achieve at least partial control of an insect (e.g., coleopteran and/or hemipteran) pest. Disclosed is a set of isolated and purified nucleic acid molecules comprising a polynucleotide, for example, as set forth in one of SEQ ID NOs:1; 3; 76; and 78; and fragments of at least 15 contiguous nucleotides thereof. In some embodiments, a stabilized dsRNA molecule may be expressed from these polynucleotides, fragments thereof, or a gene comprising one of these polynucleotides, for the post-transcriptional silencing or inhibition of a target gene. In certain embodiments, isolated and purified nucleic acid molecules comprise all or at least 15 contiguous nucleotides of any of SEQ ID NOs:1, 3, 76, and 78 (e.g., SEQ ID NOs:5-8, 80, and 81), and/or a complement or reverse complement thereof Some embodiments involve a recombinant host cell (e.g., a plant cell) having in its genome at least one recombinant DNA encoding at least one iRNA (e.g., dsRNA) molecule(s). In particular embodiments, an encoded dsRNA molecule(s) may be provided when ingested by an insect (e.g., coleopteran and/or hemipteran) pest to post-transcriptionally silence or inhibit the expression of a target gene in the pest. The recombinant DNA may comprise, for example, any of SEQ ID NOs:1, 3, 5-8, 76, 78, 80, and 81; fragments of at least 15 contiguous nucleotides of any of SEQ ID NOs:1, 3, 5-8, 76, 78, 80, and 81; and a polynucleotide consisting of a partial sequence of a gene comprising one of SEQ ID NOs:1, 3, 5-8, 76, 78, 80, and 81; and/or complements or reverse complements thereof.

Some embodiments involve a recombinant host cell having in its genome a recombinant DNA encoding at least one iRNA (e.g., dsRNA) molecule(s) comprising all or at least 15 contiguous nucleotides of any of SEQ ID NOs:89, 90, 95, and 96 (e.g., at least one polynucleotide selected from a group comprising SEQ ID NOs:91-94, 97, and 98), or the complement or reverse complement thereof. When ingested by an insect (e.g., coleopteran and/or hemipteran) pest, the iRNA molecule(s) may silence or inhibit the expression of a targetlth DNA (e.g., a DNA comprising all or at least 15 contiguous nucleotides of a polynucleotide selected from the group consisting of SEQ ID NOs:1, 3, 5-8, 76, 78, 80, and 81) in the pest or progeny of the pest, and thereby result in cessation of growth, development, viability, and/or feeding in the pest.

In some embodiments, a recombinant host cell having in its genome at least one recombinant DNA encoding at least one RNA molecule capable of forming a dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA(s). In particular embodiments, an RNA molecule capable of forming a dsRNA molecule may be expressed in a transgenic plant cell. Therefore, in these and other embodiments, a dsRNA molecule may be isolated from a transgenic plant cell. In particular embodiments, the transgenic plant is a plant selected from the group comprising corn (*Zea mays*), soybean (*Glycine max*), cotton, and plants of the family Poaceae.

Some embodiments involve a method for modulating the expression of a target gene in an insect (e.g., coleopteran or hemipteran) pest cell. In these and other embodiments, a nucleic acid molecule may be provided, wherein the nucleic acid molecule comprises a polynucleotide encoding an RNA molecule capable of forming a dsRNA molecule. In particular embodiments, a polynucleotide encoding an RNA molecule capable of forming a dsRNA molecule may be operatively linked to a promoter, and may also be operatively linked to a transcription termination sequence. In particular embodiments, a method for modulating the expression of a target gene in an insect pest cell may comprise: (a) transforming a plant cell with a vector comprising a polynucleotide encoding an RNA molecule capable of forming a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the RNA molecule capable of forming a dsRNA molecule encoded by the polynucleotide of the vector. A plant may be regenerated from a plant cell that has the vector integrated in its genome and comprises the dsRNA molecule encoded by the polynucleotide of the vector.

Thus, also disclosed is a transgenic plant comprising a vector having a polynucleotide encoding an RNA molecule capable of forming a dsRNA molecule integrated in its genome, wherein the transgenic plant comprises the dsRNA molecule encoded by the polynucleotide of the vector. In particular embodiments, expression of an RNA molecule capable of forming a dsRNA molecule in the plant is sufficient to modulate the expression of a target gene in a cell of an insect (e.g., coleopteran or hemipteran) pest that contacts the transformed plant or plant cell (for example, by feeding on the transformed plant, a part of the plant (e.g., root) or plant cell), such that growth and/or survival of the pest is inhibited. Transgenic plants disclosed herein may display protection and/or enhanced protection to insect pest infestations. Particular transgenic plants may display protection and/or enhanced protection to one or more coleopteran and/or hemipteran pest(s) selected from the group consisting of: WCR; BSB; NCR; SCR; MCR; *D. balteata* LeConte; *D. u. tenella; D. u. undecimpunctata* Mannerheim; *D. speciosa* Germar; *E. servus* (Say); *Nezara viridula* (L.); *Piezodorus guildinii* (Westwood); *Halyomorpha halys* (Stål); *Chinavia hilare* (Say); *C. marginatum* (Palisot de Beauvois); *Dichelops melacanthus* (Dallas); *D. furcatus* (F.); *Edessa meditabunda* (F.); *Thyanta perditor* (F.); *Horcias nobilellus* (Berg); *Taedia stigmosa* (Berg); *Dysdercus peruvianus* (Guérin-Méneville); *Neomegalotomus parvus* (Westwood); *Leptoglossus zonatus* (Dallas); *Niesthrea sidae* (F.); *Lygus hesperus* (Knight); and *L. lineolaris* (Palisot de Beauvois).

Also disclosed herein are methods for delivery of control agents, such as an iRNA molecule, to an insect (e.g., coleopteran or hemipteran) pest. Such control agents may cause, directly or indirectly, impairment in the ability of an insect pest population to feed, grow, or otherwise cause damage in a host. In some embodiments, a method is provided comprising delivery of a stabilized dsRNA molecule to an insect pest to suppress at least one target gene in the pest, thereby causing RNAi and reducing or eliminating plant damage in a pest host. In some embodiments, a method of inhibiting expression of a target gene in the insect pest may result in cessation of growth, survival, and/or development in the pest.

In some embodiments, compositions (e.g., a topical composition) are provided that comprise an iRNA (e.g., dsRNA) molecule for use in plants, animals, and/or the environment of a plant or animal to achieve the elimination or reduction of an insect (e.g., coleopteran or hemipteran) pest infestation. In particular embodiments, the composition may be a nutritional composition or food source to be fed to the insect pest. A nutritional composition or food source to be fed to the insect pest may be, for example and without limitation, an RNAi bait or a plant cell or tissue comprising an iRNA molecule. Some embodiments comprise making the nutritional composition or food source available to the pest. Ingestion of a composition comprising iRNA molecules may result in the uptake of the molecules by one or more cells of the pest, which may in turn result in the inhibition of expression of at least one target gene in cell(s) of the pest. Ingestion of or damage to a plant or plant cell by an insect pest infestation may be limited or eliminated in or on any host tissue or environment in which the pest is present by providing one or more compositions comprising an iRNA molecule in the host of the pest.

The compositions and methods disclosed herein may be used together in combinations with other methods and compositions for controlling damage by insect (e.g., coleopteran or hemipteran) pests. For example, an iRNA molecule as described herein for protecting plants from insect pests may be used in a method comprising the additional use of one or more chemical agents effective against an insect pest, biopesticides effective against such a pest, crop rotation, recombinant expression of other iRNA molecules, and/or recombinant genetic techniques that exhibit features different from the features of RNAi-mediated methods and RNAi compositions (e.g., recombinant production of proteins in plants that are harmful to an insect pest (e.g., Bt toxins, PIP-1 polypeptides (See, e.g., U.S. Patent Publication No. US 2014/0007292 A1), and/or AflP polypeptides (See, e.g., U.S. Patent Publication No. US 2104/0033361 A1)).

II. Abbreviations
BSB neotropical brown stink bug (*Euschistus heros*)
dsRNA double-stranded ribonucleic acid
GI growth inhibition
NCBI National Center for Biotechnology Information
gDNA genomic deoxyribonucleic acid
iRNA inhibitory ribonucleic acid
ORF open reading frame
RNAi ribonucleic acid interference
miRNA micro ribonucleic acid
shRNA small hairpin ribonucleic acid
siRNA small inhibitory ribonucleic acid
hpRNA hairpin ribonucleic acid
UTR untranslated region
WCR western corn rootworm (*Diabrotica virgifera virgifera* LeConte)
NCR northern corn rootworm (*Diabrotica barberi* Smith and Lawrence)
MCR Mexican corn rootworm (*Diabrotica virgifera zeae* Krysan and Smith)
PCR polymerase chain reaction
qPCR quantitative polymerase chain reaction
RISC RNA-induced Silencing Complex SCR southern corn rootworm (*Diabrotica undecimpunctata howardi* Barber)
SEM standard error of the mean
YFP yellow florescent protein III. Terms In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to pest insects of the order Coleoptera, including pest insects in the genus *Diabrotica*, which feed upon agricultural crops and crop products, including corn and other true grasses. In particular examples, a coleopteran pest is selected from a list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella*; *D. u. undecimpunctata* Mannerheim; and *D. speciosa* Germar.

Contact (with an organism): As used herein, the term "contact with" or "uptake by" an organism (e.g., a coleopteran or hemipteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize).

Expression: As used herein, "expression" of a coding polynucleotide (for example, a gene or a transgene) refers to the process by which the coded information of a nucleic acid transcriptional unit (including, e.g., gDNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Genetic material: As used herein, the term "genetic material" includes all genes, and nucleic acid molecules, such as DNA and RNA.

Hemipteran pest: As used herein, the term "hemipteran pest" refers to pest insects of the order Hemiptera, including, for example and without limitation, insects in the families Pentatomidae, Miridae, Pyrrhocoridae, Coreidae, Alydidae, and Rhopalidae, which feed on a wide range of host plants and have piercing and sucking mouth parts. In particular examples, a hemipteran pest is selected from the list comprising *Euschistus heros* (Fabr.) (Neotropical Brown Stink Bug), *Nezara viridula* (L.) (Southern Green Stink Bug),

*Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

Inhibition: As used herein, the term "inhibition," when used to describe an effect on a coding polynucleotide (for example, a gene), refers to a measurable decrease in the cellular level of mRNA transcribed from the coding polynucleotide and/or peptide, polypeptide, or protein product of the coding polynucleotide. In some examples, expression of a coding polynucleotide may be inhibited such that expression is approximately eliminated. "Specific inhibition" refers to the inhibition of a target coding polynucleotide without consequently affecting expression of other coding polynucleotides (e.g., genes) in the cell wherein the specific inhibition is being accomplished.

Insect: As used herein with regard to pests, the term "insect pest" specifically includes coleopteran insect pests. In some examples, the term "insect pest" specifically refers to a coleopteran pest in the genus *Diabrotica* selected from a list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella; D. u. undecimpunctata* Mannerheim; and *D. speciosa* Germar. In some embodiments, the term also includes some other insect pests; e.g., hemipteran insect pests.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, gDNA, and synthetic forms and mixed polymers of the above. A nucleotide or nucleobase may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleic acid molecule refers to a polynucleotide having nucleobases that may form base pairs with the nucleobases of the nucleic acid molecule (i.e., A-T/U, and G-C).

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

```
ATGATGATG    polynucleotide

TACTACTAC    "complement" of the polynucleotide

CATCATCAT    "reverse complement" of the
             polynucleotide
```

Some embodiments of the invention may include hairpin RNA-forming RNAi molecules. In these RNAi molecules, both the complement of a nucleic acid to be targeted by RNA interference and the reverse complement may be found in the same molecule, such that the single-stranded RNA molecule may "fold over" and hybridize to itself over the region comprising the complementary and reverse complementary polynucleotides.

"Nucleic acid molecules" include all polynucleotides, for example: single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), shRNA (small hairpin RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, gDNA, and DNA-RNA hybrids. The terms "polynucleotide" and "nucleic acid," and "fragments" thereof will be understood by those in the art as a term that includes both gDNAs, ribosomal RNAs, transfer RNAs, messenger RNAs, operons, and smaller engineered polynucleotides that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleic acid, they may be used as probes for detecting DNA or RNA. Oligonucleotides composed of DNA (oligodeoxyribonucleotides) may be used in PCR, a technique for the amplification of DNAs. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding polynucleotide," "structural polynucleotide," or "structural nucleic acid molecule" refers to a polynucleotide that is ultimately translated into a polypeptide, via transcription and mRNA, when placed under the control of appropriate regulatory elements. With respect to RNA, the term "coding polynucleotide" refers to a polynucleotide that is translated into a peptide, polypeptide, or protein. The boundaries of a coding polynucleotide are determined by a translation start codon at the 5'-terminus and a translation stop codon at the 3'-terminus. Coding polynucleotides include, but are not limited to: gDNA; cDNA; EST; and recombinant polynucleotides.

As used herein, "transcribed non-coding polynucleotide" refers to segments of mRNA molecules such as 5'UTR, 3'UTR, and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18 S rRNA, 23S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "spacer" in a nucleic acid and which is transcribed into an RNA molecule.

Lethal RNA interference: As used herein, the term "lethal RNA interference" refers to RNA interference that results in death or a reduction in viability of the subject individual to which, for example, a dsRNA, miRNA, siRNA, shRNA, and/or hpRNA is delivered.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell, such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome," as it applies to bacteria, refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two polynucleotides or polypeptides, refers to the residues in the sequences of the two molecules that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) of a molecule over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acids with even greater sequence similarity to the sequences of the reference polynucleotides will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an antiparallel alignment between the nucleobases of the two nucleic acid molecules. The two molecules are then able to form hydrogen bonds with corresponding bases on the opposite strand to form a duplex molecule that, if it is sufficiently stable, is detectable using methods well known in the art. A polynucleotide need not be 100% complementary to its target nucleic acid to be specifically hybridizable. However, the amount of complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acids. Generally, the temperature of hybridization and the ionic strength (especially the Na$^+$ and/or Mg$^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual, 2$^{nd}$ ed.*, vol. 1-3, Cold Spring Harbor Laboratory Press, Cold Spring Harbor, NY, 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the sequence of the hybridization molecule and a homologous polynucleotide within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects polynucleotides that share at least 90% sequence identity): Hybridization in 5× SSC buffer at 65° C. for 16 hours; wash twice in 2× SSC buffer at room temperature for 15 minutes each; and wash twice in 0.5× SSC buffer at 65° C. for 20 minutes each.

Moderate Stringency condition (detects polynucleotides that share at least 80% sequence identity): Hybridization in 5×-6× SSC buffer at 65-70° C. for 16-20 hours; wash twice in 2× SSC buffer at room temperature for 5-20 minutes each; and wash twice in 1× SSC buffer at 55-70° C. for 30 minutes each.

Non-stringent control condition (polynucleotides that share at least 50% sequence identity will hybridize): Hybridization in 6× SSC buffer at room temperature to 55° C. for 16-20 hours; wash at least twice in 2×-3× SSC buffer at room temperature to 55° C. for 20-30 minutes each.

As used herein, the term "substantially homologous" or "substantial homology," with regard to a nucleic acid, refers to a polynucleotide having contiguous nucleobases that hybridize under stringent conditions to the reference nucleic acid. For example, nucleic acids that are substantially homologous to a reference nucleic acid of any of SEQ ID NOs:1, 3, 5-8, 76, 78, 80, and 81 are those nucleic acids that hybridize under stringent conditions (e.g., the Moderate Stringency conditions set forth, supra) to the reference nucleic acid. Substantially homologous polynucleotides may have at least 80% sequence identity. For example, substantially homologous polynucleotides may have from about 80% to 100% sequence identity, such as 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target polynucleotides under conditions where specific binding is desired, for example, under stringent hybridization conditions.

As used herein, the term "ortholog" refers to a gene in two or more species that has evolved from a common ancestral nucleic acid, and may retain the same function in the two or more species.

As used herein, two nucleic acid molecules are said to exhibit "complete complementarity" when every nucleotide of a polynucleotide read in the 5' to 3' direction is complementary to every nucleotide of the other polynucleotide when read in the 3' to 5' direction. A polynucleotide that is complementary to a reference polynucleotide will exhibit a sequence identical to the reverse complement of the reference polynucleotide. These terms and descriptions are well defined in the art and are easily understood by those of ordinary skill in the art.

Operably linked: A first polynucleotide is operably linked with a second polynucleotide when the first polynucleotide is in a functional relationship with the second polynucleotide. When recombinantly produced, operably linked polynucleotides are generally contiguous, and, where necessary to join two protein-coding regions, in the same reading frame (e.g., in a translationally fused ORF). However, nucleic acids need not be contiguous to be operably linked.

The term, "operably linked," when used in reference to a regulatory genetic element and a coding polynucleotide, means that the regulatory element affects the expression of the linked coding polynucleotide. "Regulatory elements," or "control elements," refer to polynucleotides that influence the timing and level/amount of transcription, RNA processing or stability, or translation of the associated coding polynucleotide. Regulatory elements may include promoters; translation leaders; introns; enhancers; stem-loop structures; repressor binding polynucleotides; polynucleotides with a termination sequence; polynucleotides with a polyadenylation recognition sequence; etc. Particular regulatory elements may be located upstream and/or downstream of a coding polynucleotide operably linked thereto. Also, particular regulatory elements operably linked to a coding polynucleotide may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding polynucleotide for expression in a cell, or a promoter may be operably linked to a polynucleotide encoding a signal peptide which may be operably linked to a coding polynucleotide for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter that may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, Xba1/NcoI fragment 5' to the *Brassica napus* ALS3 structural gene (or a polynucleotide similar to said Xba1/NcoI fragment) (International PCT Publication No. W096/30530).

Additionally, any tissue-specific or tissue-preferred promoter may be utilized in some embodiments of the invention. Plants transformed with a nucleic acid molecule comprising a coding polynucleotide operably linked to a tissue-specific promoter may produce the product of the coding polynucleotide exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Soybean plant: As used herein, the term "soybean plant" refers to a plant of the species *Glycine*; for example, *Glycine max*.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid. In some examples, a transgene may be a DNA that encodes one or both strand(s) of an RNA capable of forming a dsRNA molecule that comprises a polynucleotide that is complementary to a nucleic acid molecule found in a coleopteran and/or hemipteran pest. In further examples, a transgene may be an antisense polynucleotide, wherein expression of the antisense polynucleotide inhibits expression of a target nucleic acid, thereby producing an RNAi phenotype. In still further examples, a transgene may be a gene (e.g., a herbicide-tolerance gene, a gene encoding an industrially or pharmaceutically useful compound, or a gene encoding a desirable agricultural trait). In these and other examples, a transgene may contain regulatory elements operably linked to a coding polynucleotide of the transgene (e.g., a promoter).

Vector: A nucleic acid molecule as introduced into a cell, for example, to produce a transformed cell. A vector may include genetic elements that permit it to replicate in the host cell, such as an origin of replication. Examples of vectors include, but are not limited to: a plasmid; cosmid; bacteriophage; or virus that carries exogenous DNA into a cell. A vector may also include one or more genes, including ones that produce antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% or greater relative to the yield of check varieties in the same growing location containing significant densities of the coleopteran and/or hemipteran pests that are injurious to that crop growing at the same time and under the same conditions, which are targeted by the compositions and methods herein.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R.A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV Nucleic Acid Molecules Comprising an Insect Pest Sequence

A. Overview

Described herein are nucleic acid molecules useful for the control of insect pests. In some examples, the insect pest is a coleopteran (e.g., species of the genus *Diabrotica*) or hemipteran (e.g., species of the genus *Euschistus*) insect pest. Described nucleic acid molecules include target polynucleotides (e.g., native genes, and non-coding polynucleotides), dsRNAs, siRNAs, shRNAs, hpRNAs, and miRNAs. For example, dsRNA, siRNA, miRNA, shRNA, and/or hpRNA molecules are described in some embodiments that may be specifically complementary to all or part of one or more native nucleic acids in a coleopteran and/or hemipteran pest. In these and further embodiments, the native nucleic acid(s) may be one or more target gene(s), the product of which may be, for example and without limitation: involved in a metabolic process or involved in larval/nymph development. Nucleic acid molecules described herein, when introduced into a cell comprising at least one native nucleic acid(s) to which the nucleic acid molecules are specifically complementary, may initiate RNAi in the cell, and consequently reduce or eliminate expression of the native nucleic acid(s). In some examples, reduction or elimination of the expression of a target gene by a nucleic acid molecule specifically complementary thereto may result in reduction or cessation of growth, development, and/or feeding in the pest.

In some embodiments, at least one target gene in an insect pest may be selected, wherein the target gene comprises an fsh polynucleotide. In some examples, a target gene in a coleopteran pest (for example, in a coleopteran pest in the genus *Diabrotica*) is selected, wherein the target gene comprises a polynucleotide selected from among SEQ ID NOs: 1, 3, and 5-8. In particular examples, a target gene in a hemipteran pest is selected, wherein the target gene comprises a polynucleotide selected from among SEQ ID NOs: 76, 78, 80, and 81.

In some embodiments, a target gene may be a nucleic acid molecule comprising a polynucleotide that can be reverse translated in silico to a polypeptide comprising a contiguous amino acid sequence that is at least about 85% identical (e.g., at least 84%, 85%, about 90%, about 95%, about 96%, about 97%, about 98%, about 99%, about 100%, or 100% identical) to the amino acid sequence of a protein product of an fsh polynucleotide. A target gene may be any fsh polynucleotide in an insect pest, the post-transcriptional inhibition of which has a deleterious effect on the growth, survival, and/or viability of the pest, for example, to provide a protective benefit against the pest to a plant. In particular examples, a target gene is a nucleic acid molecule comprising a polynucleotide that can be reverse translated in silico to a polypeptide comprising a contiguous amino acid sequence that is at least about 85% identical, about 90% identical, about 95% identical, about 96% identical, about 97% identical, about 98% identical, about 99% identical, about 100% identical, or 100% identical to the amino acid sequence of SEQ ID NO:2; SEQ ID NO:4; SEQ ID NO:77; or SEQ ID NO:79.

Provided according to the invention are DNAs, the expression of which results in an RNA molecule comprising a polynucleotide that is specifically complementary to all or part of a native RNA molecule that is encoded by a coding polynucleotide in an insect (e.g., coleopteran and/or hemipteran) pest. In some embodiments, after ingestion of the expressed RNA molecule by an insect pest, down-regulation of the coding polynucleotide in cells of the pest may be obtained. In particular embodiments, down-regulation of the coding polynucleotide in cells of the pest may be obtained. In particular embodiments, down-regulation of the coding polynucleotide in cells of the insect pest results in a deleterious effect on the growth and/or development of the pest.

In some embodiments, target polynucleotides include transcribed non-coding RNAs, such as 5'UTRs; 3'UTRs; spliced leaders; introns; outrons (e.g., 5'UTR RNA subsequently modified in trans splicing); donatrons (e.g., non-coding RNA required to provide donor sequences for trans splicing); and other non-coding transcribed RNA of target insect pest genes. Such polynucleotides may be derived from both mono-cistronic and poly-cistronic genes.

Thus, also described herein in connection with some embodiments are iRNA molecules (e.g., dsRNAs, siRNAs, miRNAs, shRNAs, and hpRNAs) that comprise at least one polynucleotide that is specifically complementary to all or part of a target nucleic acid in an insect (e.g., coleopteran and/or hemipteran) pest. In some embodiments an iRNA molecule may comprise polynucleotide(s) that are complementary to all or part of a plurality of target nucleic acids; for example, 2, 3, 4, 5, 6, 7, 8, 9, 10, or more target nucleic acids. In particular embodiments, an iRNA molecule may be produced in vitro or in vivo by a genetically-modified organism, such as a plant or bacterium. Also disclosed are cDNAs that may be used for the production of dsRNA molecules, siRNA molecules, miRNA molecules, shRNA molecules, and/or hpRNA molecules that are specifically complementary to all or part of a target nucleic acid in an insect pest. Further described are recombinant DNA constructs for use in achieving stable transformation of particular host targets. Transformed host targets may express effective levels of dsRNA, siRNA, miRNA, shRNA, and/or hpRNA molecules from the recombinant DNA constructs. Therefore, also described is a plant transformation vector comprising at least one polynucleotide operably linked to a heterologous promoter functional in a plant cell, wherein expression of the polynucleotide(s) results in an RNA molecule comprising a string of contiguous nucleobases that is specifically complementary to all or part of a target nucleic acid in an insect pest.

In particular examples, nucleic acid molecules useful for the control of insect (e.g., coleopteran and/or hemipteran) pests may include: all or at least 15 contiguous nucleotides of a native nucleic acid isolated from a *Diabrotica* organism comprising anfsh polynucleotide (e.g., any of SEQ ID NOs:1, 3, and 5-8); all or at least 15 contiguous nucleotides of a native nucleic acid isolated from a hemipteran organism comprising an fsh polynucleotide (e.g., any of SEQ ID NOs:76, 78, 80, and 81); DNAs that when expressed result in an RNA molecule comprising a polynucleotide that is specifically complementary to all or part of a native RNA molecule that is encoded by fsh; iRNA molecules (e.g., dsRNAs, siRNAs, miRNAs, shRNAs, and hpRNAs) that comprise at least one polynucleotide that is specifically complementary to all or part offsh; cDNAs that may be used for the production of dsRNA molecules, siRNA molecules, miRNA molecules, shRNA molecules, and/or hpRNA molecules that are specifically complementary to all or part offsh; and recombinant DNA constructs for use in achieving stable transformation of particular host targets, wherein a transformed host target comprises one or more of the foregoing nucleic acid molecules.

B. Nucleic Acid Molecules

Embodiments include, inter alia, iRNA (e.g., dsRNA, siRNA, miRNA, shRNA, and hpRNA) molecules that inhibit target gene expression in a cell, tissue, or organ of an insect (e.g., coleopteran and/or hemipteran) pest; and DNA molecules capable of being expressed as an iRNA molecule in a cell or microorganism to inhibit target gene expression in a cell, tissue, or organ of an insect pest.

Some embodiments of the invention provide an isolated nucleic acid molecule comprising at least one (e.g., one, two, three, or more) polynucleotide(s) selected from the group consisting of: SEQ ID NOs:1 and 3; the complement or reverse complement of either of SEQ ID NOs:1 and 3; a fragment of at least 15 contiguous nucleotides of either of SEQ ID NOs:1 and 3 (e.g., any of SEQ ID NOs:5-8); the complement or reverse complement of a fragment of at least 15 contiguous nucleotides of either of SEQ ID NOs:1 and 3; a native coding polynucleotide of a *Diabrotica* organism (e.g., WCR) comprising any of SEQ ID NOs:5-8; the complement or reverse complement of a native coding polynucleotide of a *Diabrotica* organism comprising any of SEQ ID NOs:5-8; a fragment of at least 15 contiguous nucleotides of a native coding polynucleotide of a *Diabrotica* organism comprising any of SEQ ID NOs:5-8; and the complement or reverse complement of a fragment of at least 15 contiguous nucleotides of a native coding polynucleotide of a *Diabrotica* organism comprising any of SEQ ID NOs:5-8.

Some embodiments of the invention provide an isolated nucleic acid molecule comprising at least one (e.g., one, two, three, or more) polynucleotide(s) selected from the group consisting of: SEQ ID NOs:76 and 78; the complement or reverse complement of either of SEQ ID NOs:76 and 78; a fragment of at least 15 contiguous nucleotides of either of SEQ ID NOs:76 and 78 (e.g., SEQ ID NOs:80 and 81); the complement or reverse complement of a fragment of at least 15 contiguous nucleotides of either of SEQ ID NOs:76 and 78; a native coding polynucleotide of a hemipteran organism (e.g., BSB) comprising either of SEQ ID NOs:80 and 81; the complement or reverse complement of a native coding polynucleotide of a hemipteran organism comprising either of SEQ ID NOs:80 and 81; a fragment of at least 15 contiguous nucleotides of a native coding polynucleotide of a hemipteran organism comprising either of SEQ ID NOs:80 and 81; and the complement or reverse complement of a fragment of at least 15 contiguous nucleotides of a native coding polynucleotide of a hemipteran organism comprising either of SEQ ID NOs:80 and 81.

In particular embodiments, contact with or uptake by an insect (e.g., coleopteran and/or hemipteran) pest of an iRNA transcribed from the isolated polynucleotide inhibits the growth, development, and/or feeding of the pest. In some embodiments, contact with or uptake by the insect occurs via feeding on plant material or bait comprising the iRNA ("RNAi bait"). In some embodiments, contact with or uptake by the insect occurs via spraying of a plant comprising the insect with a composition comprising the iRNA.

In some embodiments, an isolated nucleic acid molecule of the invention may comprise at least one (e.g., one, two, three, or more) polynucleotide(s) selected from the group consisting of: SEQ ID NO:89; the complement or reverse complement of SEQ ID NO:89; SEQ ID NO:90; the complement or reverse complement of SEQ ID NO:90; SEQ ID NO:91; the complement or reverse complement of SEQ ID NO:91; SEQ ID NO:92; the complement or reverse complement of SEQ ID NO:92; SEQ ID NO:93; the complement or reverse complement of SEQ ID NO:93; SEQ ID NO:94; the complement or reverse complement of SEQ ID NO:94; SEQ ID NO:95; the complement or reverse complement of SEQ ID NO:95; SEQ ID NO:96; the complement or reverse complement of SEQ ID NO:96; SEQ ID NO:97; the complement or reverse complement of SEQ ID NO:97; SEQ ID NO:98; the complement or reverse complement of SEQ ID NO:98; a fragment of at least 15 contiguous nucleotides of any of SEQ ID NOs:89-98; the complement or reverse complement of a fragment of at least 15 contiguous nucleotides of any of SEQ ID NOs:89-98; a native coding polynucleotide of a *Diabrotica* organism comprising any of SEQ ID NOs:89-94; the complement or reverse complement of a native coding polynucleotide of a *Diabrotica* organism comprising any of SEQ ID NOs:89-94; a fragment of at least 15 contiguous nucleotides of a native coding polynucleotide of a *Diabrotica* organism comprising any of SEQ ID NOs: 89-94; the complement or reverse complement of a fragment of at least 15 contiguous nucleotides of a native coding polynucleotide of a *Diabrotica* organism comprising any of SEQ ID NOs:89-94; a native coding polynucleotide of a *Euschistus* organism comprising any of SEQ ID NOs:95-98; the complement or reverse complement of a native coding polynucleotide of a *Euschistus* organism comprising any of SEQ ID NOs:95-98; a fragment of at least 15 contiguous nucleotides of a native coding polynucleotide of a *Euschistus* organism comprising any of SEQ ID NOs:95-98; and the complement or reverse complement of a fragment of at least 15 contiguous nucleotides of a native coding polynucleotide of a *Euschistus* organism comprising any of SEQ ID NOs: 95-98.

In certain embodiments, dsRNA molecules provided by the invention comprise polynucleotides complementary to a transcript from a target gene comprising any of SEQ ID NOs:1, 3, 76, and 78, and fragments of at least 15 contiguous nucleotides thereof, the inhibition of which target gene in an insect pest results in the reduction or removal of a polypeptide or polynucleotide agent that is essential for the pest's growth, development, or other biological function. A selected polynucleotide may exhibit from about 80% to about 100% sequence identity to any of SEQ ID NOs:1, 3, 76, and 78; a fragment of at least 15 contiguous nucleotides of any of SEQ ID NOs:1, 3, 76, and 78; and the complement or reverse compliment of any of the foregoing. For example, a selected polynucleotide may exhibit 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to any of any of SEQ ID NOs:1, 3, 76, and 78; a fragment of at least 15 contiguous nucleotides of any of any of SEQ ID NOs:1, 3, 76, and 78 (e.g., SEQ ID NOs:5-8, 80, and 81); and the complement or reverse complement of any of the foregoing.

In some embodiments, a DNA molecule capable of being expressed as an iRNA molecule in a cell or microorganism to inhibit target gene expression may comprise a single polynucleotide that is specifically complementary to all or part of a native polynucleotide found in one or more target insect pest species (e.g., a coleopteran or hemipteran pest species), or the DNA molecule can be constructed as a chimera from a plurality of such specifically complementary polynucleotides.

In other embodiments, a nucleic acid molecule may comprise a first and a second polynucleotide separated by a "spacer." A spacer may be a region comprising any sequence of nucleotides that facilitates secondary structure formation between the first and second polynucleotides, where this is desired. In one embodiment, the spacer is part of a sense or antisense coding polynucleotide for mRNA. The spacer may alternatively comprise any combination of nucleotides or homologues thereof that are capable of being linked covalently to a nucleic acid molecule. In some examples, the spacer may be an intron (e.g., as ST-LS1 intron).

For example, in some embodiments, the DNA molecule may comprise a polynucleotide coding for one or more different iRNA molecules, wherein each of the different iRNA molecules comprises a first polynucleotide and a second polynucleotide, wherein the first and second polynucleotides are complementary to each other. The first and second polynucleotides may be connected within an RNA molecule by a spacer. The spacer may constitute part of the first polynucleotide or the second polynucleotide. Expression of an RNA molecule comprising the first and second nucleotide polynucleotides may lead to the formation of a dsRNA molecule, by specific intramolecular base-pairing of the first and second nucleotide polynucleotides. The first polynucleotide or the second polynucleotide may be substantially identical to a polynucleotide (e.g., a target gene, or transcribed non-coding polynucleotide) native to an insect pest (e.g., a coleopteran or hemipteran pest), a derivative thereof, or a complementary polynucleotide thereto.

dsRNA nucleic acid molecules comprise double strands of polymerized ribonucleotides, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNAs transcribed from a target gene, and both RNA molecules are subsequently degraded by an inherent cellular RNA-degrading mechanism. This process may result in the effective degradation or removal of the RNA encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in insect pests.

In some embodiments, a nucleic acid molecule may include at least one non-naturally occurring polynucleotide that can be transcribed into a single-stranded RNA molecule capable of forming a dsRNA molecule in vivo through intermolecular hybridization. Such dsRNAs typically self-assemble, and can be provided in the nutrition source of an insect (e.g., coleopteran or hemipteran) pest to achieve the post-transcriptional inhibition of a target gene. In these and further embodiments, a nucleic acid molecule may comprise two different non-naturally occurring polynucleotides, each of which is specifically complementary to a different target gene in an insect pest. When such a nucleic acid molecule is provided as a dsRNA molecule to, for example, a coleopteran and/or hemipteran pest, the dsRNA molecule inhibits the expression of at least two different target genes in the pest.

C. Obtaining Nucleic Acid Molecules

A variety of polynucleotides in insect (e.g., coleopteran and hemipteran) pests may be used as targets for the design of nucleic acid molecules, such as iRNAs and DNA molecules encoding iRNAs. Selection of native polynucleotides is not, however, a straight-forward process. For example, only a small number of native polynucleotides in a coleopteran or hemipteran pest will be effective targets. It cannot be predicted with certainty whether a particular native polynucleotide can be effectively down-regulated by nucleic acid molecules of the invention, or whether down-regulation of a particular native polynucleotide will have a detrimental effect on the growth, viability, feeding, and/or survival of an insect pest. The vast majority of native coleopteran and hemipteran pest polynucleotides, such as ESTs isolated therefrom (for example, the coleopteran pest polynucleotides listed in U.S. Pat. No. 7,612,194), do not have a detrimental effect on the growth and/or viability of the pest. Neither is it predictable which of the native polynucleotides that may have a detrimental effect on an insect pest are able to be used in recombinant techniques for expressing nucleic acid molecules complementary to such native polynucleotides in a host plant and providing the detrimental effect on the pest upon feeding without causing harm to the host plant.

In some embodiments, nucleic acid molecules (e.g., dsRNA molecules to be provided in the host plant of an insect (e.g., coleopteran or hemipteran) pest) are selected to target cDNAs that encode proteins or parts of proteins essential for pest development, such as polypeptides involved in metabolic or catabolic biochemical pathways, cell division, energy metabolism, digestion, host plant recognition, and the like. As described herein, ingestion of compositions by a target pest organism containing one or more dsRNAs, at least one segment of which is specifically complementary to at least a substantially identical segment of RNA produced in the cells of the target pest organism, can result in the death or other inhibition of the target. A polynucleotide, either DNA or RNA, derived from an insect pest can be used to construct plant cells protected against infestation by the pests. The host plant of the coleopteran and/or hemipteran pest (e.g., Z. mays or G. max), for example, can be transformed to contain one or more polynucleotides derived from the coleopteran and/or hemipteran pest as provided herein. The polynucleotide transformed into the host may encode one or more RNAs that form into a dsRNA structure in the cells or biological fluids within the transformed host, thus making the dsRNA available if/when the pest forms a nutritional relationship with the transgenic host. This may result in the suppression of expression of one or more genes in the cells of the pest, and ultimately death or inhibition of its growth or development.

In particular embodiments, a gene is targeted that is essentially involved in the growth and development of an insect (e.g., coleopteran or hemipteran) pest. Other target genes for use in the present invention may include, for example, those that play important roles in pest viability, movement, migration, growth, development, infectivity, and establishment of feeding sites. A target gene may therefore be a housekeeping gene or a transcription factor. Additionally, a native insect pest polynucleotide for use in the present invention may also be derived from a homolog (e.g., an ortholog), of a plant, viral, bacterial or insect gene, the function of which is known to those of skill in the art, and the polynucleotide of which is specifically hybridizable with a target gene in the genome of the target pest. Methods of identifying a homolog of a gene with a known nucleotide sequence by hybridization are known to those of skill in the art.

In some embodiments, the invention provides methods for obtaining a nucleic acid molecule comprising a polynucleotide for producing an iRNA (e.g., dsRNA, siRNA, miRNA, shRNA, and hpRNA) molecule. One such embodiment comprises: (a) analyzing one or more target gene(s) for their expression, function, and phenotype upon dsRNA-mediated gene suppression in an insect (e.g., coleopteran or hemipteran) pest; (b) probing a cDNA or gDNA library with a probe comprising all or a portion of a polynucleotide or a homolog thereof from a targeted pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA or a homolog thereof; and (f) chemically synthesizing all or a substantial portion of a gene, or an siRNA, miRNA, hpRNA, mRNA, shRNA, or dsRNA.

In further embodiments, a method for obtaining a nucleic acid fragment comprising a polynucleotide for producing a substantial portion of an iRNA (e.g., dsRNA, siRNA, miRNA, shRNA, and hpRNA) molecule includes: (a) synthesizing first and second oligonucleotide primers specifically complementary to a portion of a native polynucleotide from a targeted insect (e.g., coleopteran or hemipteran) pest; and (b) amplifying a cDNA or gDNA insert present in a cloning vector using the first and second oligonucleotide primers of step (a), wherein the amplified nucleic acid molecule comprises a substantial portion of a siRNA, miRNA, hpRNA, mRNA, shRNA, or dsRNA molecule.

Nucleic acids can be isolated, amplified, or produced by a number of approaches. For example, an iRNA (e.g., dsRNA, siRNA, miRNA, shRNA, and hpRNA) molecule may be obtained by PCR amplification of a target polynucleotide (e.g., a target gene or a target transcribed non-coding polynucleotide) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present invention may be produced chemically or enzymatically by one skilled in the art through manual or automated reactions, or in vivo in a cell comprising a nucleic acid molecule comprising a polynucleotide encoding the RNA, dsRNA, siRNA, miRNA, shRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of polynucleotides are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in an insect pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a polynucleotide that, upon expression to RNA and ingestion by an insect (e.g., coleopteran and/or hemipteran) pest, achieves suppression of a target gene in a cell, tissue, or organ of the pest. Thus, some embodiments provide a recombinant nucleic acid molecule comprising a polynucleotide capable of being expressed as an iRNA (e.g., dsRNA, siRNA, miRNA, shRNA, and hpRNA) molecule in a plant cell to inhibit target gene expression in an insect pest. In order to initiate or enhance expression, such recombinant nucleic acid molecules may comprise one or more regulatory elements, which regulatory elements may be operably linked to the polynucleotide capable of being expressed as an iRNA. Methods to express a gene suppression molecule in plants are known, and may be used to express a polynucleotide of the present invention. See, e.g., International PCT Publication No. WO06/073727; and U.S. Patent Publication No. 2006/0200878 A1)

In specific embodiments, a recombinant DNA molecule of the invention may comprise a polynucleotide encoding an RNA that may form a dsRNA molecule. Such recombinant DNA molecules may encode RNAs that may form dsRNA molecules capable of inhibiting the expression of endogenous target gene(s) in an insect (e.g., coleopteran and/or hemipteran) pest cell upon ingestion. In many embodiments, a transcribed RNA may form a dsRNA molecule that may be provided in a stabilized form; e.g., as a hairpin and stem and loop structure.

In some embodiments, one strand of a dsRNA molecule may be formed by transcription from a polynucleotide which is substantially homologous to a polynucleotide selected from the group consisting of SEQ ID NOs:1, 3, 76, and 78; the complement or reverse complement of any of SEQ ID NOs:1, 3, 76, and 78; a fragment of at least 15 contiguous nucleotides of any of SEQ ID NOs:1, 3, 76, and 78 (e.g., SEQ ID NOs:5-8, 80, and 81); the complement or reverse complement of a fragment of at least 15 contiguous nucleotides of any of SEQ ID NOs:1, 3, 76, and 78; a native coding polynucleotide of a *Diabrotica* organism (e.g., WCR) comprising any of SEQ ID NOs:5-8; the complement or reverse complement of a native coding polynucleotide of a *Diabrotica* organism comprising any of SEQ ID NOs:5-8; a fragment of at least 15 contiguous nucleotides of a native coding polynucleotide of a *Diabrotica* organism comprising any of SEQ ID NOs:5-8; the complement or reverse complement of a fragment of at least 15 contiguous nucleotides of a native coding polynucleotide of a *Diabrotica* organism comprising any of SEQ ID NOs:5-8; a native coding polynucleotide of a hemipteran organism (e.g., BSB) comprising either of SEQ ID NOs:80 and 81; the complement or reverse complement of a native coding polynucleotide of a hemipteran organism comprising either of SEQ ID NOs:80 and 81; a fragment of at least 15 contiguous nucleotides of a native coding polynucleotide of a hemipteran organism comprising either of SEQ ID NOs:80 and 81; and the complement or reverse complement of a fragment of at least 15 contiguous nucleotides of a native coding polynucleotide of a hemipteran organism comprising either of SEQ ID NOs:80 and 81.

In some embodiments, one strand of a dsRNA molecule may be formed by transcription from a polynucleotide that is substantially homologous to a polynucleotide selected from the group consisting of SEQ ID NOs:5-8, 80, and 81; the complement or reverse compliment of any of SEQ ID NOs:5-8, 80, and 81; a fragment of at least 15 contiguous nucleotides of any of SEQ ID NOs:1, 3, 76, and 78; and the complement or reverse compliment of a fragment of at least 15 contiguous nucleotides of any of SEQ ID NOs:1, 3, 76, and 78.

In particular embodiments, a recombinant DNA molecule encoding an RNA that may form a dsRNA molecule may comprise a coding region wherein at least two polynucleotides are arranged such that one polynucleotide is in a sense orientation, and the other polynucleotide is in an antisense orientation, relative to at least one promoter, wherein the sense polynucleotide and the antisense polynucleotide are linked or connected by a spacer of, for example, from about five (~5) to about one thousand (~1000) nucleotides. The spacer may form a loop between the sense and antisense polynucleotides. The sense polynucleotide or the antisense polynucleotide may be substantially homologous to a target gene (e.g., an fsh gene comprising any of SEQ ID NOs:1, 3, 5-8, 76, 78, 80, and 81) or a fragment comprising at least 15 contiguous nucleotides thereof. In some embodiments, however, a recombinant DNA molecule may encode an RNA that may form a dsRNA molecule without a spacer. In embodiments, a sense coding polynucleotide and an antisense coding polynucleotide may be different lengths.

Polynucleotides identified as having a deleterious effect on an insect pest or a plant-protective effect with regard to the pest may be readily incorporated into expressed dsRNA molecules through the creation of appropriate expression cassettes in a recombinant nucleic acid molecule of the invention. For example, such polynucleotides may be expressed as a hairpin with stem and loop structure by taking a first segment corresponding to a target gene polynucleotide (e.g., an fsh gene comprising any of SEQ ID NOs:1, 3, 5-8, 76, 78, 80, and 81, and a fragment comprising at least 15 contiguous nucleotides of any of the foregoing); linking this polynucleotide to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms comprising the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native insect (e.g., coleopteran and/or hemipteran) pest polynucleotide is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Some embodiments of the invention include introduction of a recombinant nucleic acid molecule of the present invention into a plant (i.e., transformation) to achieve insect (e.g., coleopteran and/or hemipteran) pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acids of the invention can, for example, be suitably inserted into a vector under the control of a suitable promoter that functions in one or more hosts to drive expression of a linked coding polynucleotide or other DNA element. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart protection from an insect (e.g., coleopteran and/or hemipteran) pest to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a polynucleotide that is substantially homologous and specifically hybridizable to a corresponding transcribed polynucleotide within an insect pest that may cause damage to the host plant species. The pest may contact the iRNA molecule that is transcribed in cells of the transgenic host plant, for example, by ingesting cells or fluids of the transgenic host plant that comprise the iRNA molecule. Thus, in particular examples, expression of a target gene is suppressed by the iRNA molecule within coleopteran and/or hemipteran pests that infest the transgenic host plant. In some embodiments, suppression of expression of the target gene in a target coleopteran and/or hemipteran pest may result in the plant being protected against attack by the pest.

In order to enable delivery of iRNA molecules to an insect pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a polynucleotide of the invention operably linked to one or more regulatory elements, such as a heterologous promoter element that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a root-specific promoter. Root-specific promoters drive expression of operably-linked coding polynucleotides exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a polynucleotide or fragment for coleopteran pest control according to the invention may be cloned between two root-specific promoters oriented in opposite transcriptional directions relative to the polynucleotide or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by an insect pest so that suppression of target gene expression is achieved.

Additional regulatory elements that may optionally be operably linked to a nucleic acid include 5'UTRs located between a promoter element and a coding polynucleotide that function as a translation leader element. The translation leader element is present in fully-processed mRNA, and it may affect processing of the primary transcript, and/or RNA stability. Examples of translation leader elements include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAntl; TEV (Carrington and Freed (1990) J. Virol. 64:1590-7); and AGRtunos (GenBank™ Accession No. V00087; and Bevan et al. (1983) Nature 304:184-7).

Additional regulatory elements that may optionally be operably linked to a nucleic acid also include 3' non-translated elements, 3' transcription termination regions, or polyadenylation regions. These are genetic elements located downstream of a polynucleotide, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation element can be derived from a variety of plant genes, or from T-DNA genes. A non-limiting example of a 3' transcription termination region is the nopaline synthase 3' region (nos 3; Fraley et al. (1983) Proc. Natl. Acad. Sci. USA 80:4803-7). An example of the use of different 3' non-translated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory elements operatively linked to one or more polynucleotides of the present invention. When expressed, the one or more polynucleotides result in one or more iRNA molecule(s) comprising a polynucleotide that is specifically complementary to all or part of a native RNA molecule in an insect (e.g., coleopteran and/or hemipteran) pest. Thus, the polynucleotide(s) may comprise a segment encoding all or part of a polyribonucleotide present within a targeted coleopteran and/or hemipteran pest RNA transcript, and may comprise inverted repeats of all or a part of a targeted pest transcript. A plant transformation vector may contain polynucleotides specifically complementary to more than one target polynucleotide, thus allowing production of more than one dsRNA for inhibiting expression of two or more genes in cells of one or more populations or species of target insect pests. Segments of polynucleotides specifically complementary to polynucleotides present in different genes can be combined into a single composite nucleic acid molecule for expression in a transgenic plant. Such segments may be contiguous or separated by a spacer.

In other embodiments, a plasmid of the present invention already containing at least one polynucleotide(s) of the invention can be modified by the sequential insertion of additional polynucleotide(s) in the same plasmid, wherein the additional polynucleotide(s) are operably linked to the same regulatory elements as the original at least one polynucleotide(s). In some embodiments, a nucleic acid molecule may be designed for the inhibition of multiple target genes. In some embodiments, the multiple genes to be inhibited can be obtained from the same insect (e.g., coleopteran or hemipteran) pest species, which may enhance the effectiveness of the nucleic acid molecule. In other embodiments, the genes can be derived from different insect pests, which may broaden the range of pests against which the agent(s) is/are effective. When multiple genes are targeted for suppression or a combination of expression and suppression, a polycistronic DNA element can be engineered.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide tolerance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate tolerance; a nitrilase gene which confers resistance to bromoxynil; a mutant acetolactate synthase (ALS) gene which confers imidazolinone or sulfonylurea tolerance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ Stadler Genetics Symposium, P. Gustafson and R. Appels, eds. (New York: Plenum), pp. 263-82; a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to insect (e.g., coleopteran and/or hemipteran) pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by Agrobacterium-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acids encoding one or more iRNA molecules in the genome of the transgenic plant.

The most widely utilized method for introducing an expression vector into plants is based on the natural transformation system of Agrobacterium. A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border elements. The T-region may also contain a selectable marker for efficient recovery of transgenic cells and plants, and a multiple cloning site for inserting polynucleotides for transfer such as a dsRNA encoding nucleic acid.

In particular embodiments, a plant transformation vector is derived from a Ti plasmid of A. tumefaciens (See, e.g., U.S. Pat. Nos. 4,536,475, 4,693,977, 4,886,937, and 5,501, 967; and European Patent No. EP 0 122 791) or a Ri plasmid of A. rhizogenes. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as Sinorhizobium, Rhizobium, and Mesorhizo-

*bium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA encoding one or more iRNA molecules that inhibit target gene expression in a coleopteran and/or hemipteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of gDNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to gDNA derived from any plant species (e.g., *Z. mays*) or tissue type, including cell cultures.

A transgenic plant formed using *Agrobacterium*-dependent transformation methods typically contains a single recombinant DNA inserted into one chromosome. The polynucleotide of the single recombinant DNA is referred to as a "transgenic event" or "integration event". Such transgenic plants are heterozygous for the inserted exogenous polynucleotide. In some embodiments, a transgenic plant homozygous with respect to a transgene may be obtained by sexually mating (selfing) an independent segregant transgenic plant that contains a single exogenous gene to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have an insect (e.g., coleopteran and/or hemipteran) pest-inhibitory effect. The iRNA molecules (e.g., dsRNA molecules) may be expressed from multiple nucleic acids introduced in different transformation events, or from a single nucleic acid introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple polynucleotides that are each homologous to different loci within one or more insect pests (for example, the loci defined by SEQ ID NOs:1, 3, 76, and 78), both in different populations of the same species of insect pest, or in different species of insect pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a polynucleotide that encodes an iRNA molecule may be introduced into a first plant line that is amenable to transformation to produce a transgenic plant, which transgenic plant may be crossed with a second plant line to introgress the polynucleotide that encodes the iRNA molecule into the second plant line.

In some aspects, seeds and commodity products produced by transgenic plants derived from transformed plant cells are included, wherein the seeds or commodity products comprise a detectable amount of a nucleic acid of the invention. In some embodiments, such commodity products may be produced, for example, by obtaining transgenic plants and preparing food or feed from them. Commodity products comprising one or more of the polynucleotides of the invention includes, for example and without limitation: meals, oils, crushed or whole grains or seeds of a plant, and any food product comprising any meal, oil, or crushed or whole grain of a recombinant plant or seed comprising one or more of the nucleic acids of the invention. The detection of one or more of the polynucleotides of the invention in one or more commodity or commodity products is de facto evidence that the commodity or commodity product is produced from a transgenic plant designed to express one or more of the iRNA molecules of the invention for the purpose of controlling insect (e.g., coleopteran and/or hemipteran) pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran or hemipteran pest other than the one defined by SEQ ID NO:1, SEQ ID NO:3, SEQ ID NO:76, and SEQ ID NO:78, such as, for example, one or more loci selected from the group consisting of Caf1-180 (U.S. Patent Application Publication No. 2012/0174258), VatpaseC (U.S. Patent Application Publication No. 2012/0174259), Rho1 (U.S.

Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), ROP RNAi targets, as described in U.S. patent application Ser. No. 14/577,811, RNA polymerase II RNAi targets, as described in U.S. Patent Application No. 62/133,214, RNA polymerase 11140 RNAi targets, as described in U.S. patent application Ser. No. 14/577,854, RNA polymerase 11215 RNAi targets, as described in U.S. Patent Application No. 62/133,202, RNA polymerase 1133 RNAi targets, as described in U.S. Patent Application No. 62/133,210, ncm RNAi targets, as described in U.S. Patent Application No. 62/095487, Dre4 RNAi targets, as described in U.S. patent application Ser. No. 14/705,807, transcription elongation factor spt5 RNAi targets, as described in U.S. Patent Application No. 62/168613, and histone chaperone spt6 RNAi targets, as described in U.S. Patent Application No. 62/168606; a transgenic event from which is transcribed an iRNA molecule targeting a gene in an organism other than a coleopteran and/or hemipteran pest (e.g., a plant-parasitic nematode); a gene encoding an insecticidal protein (e.g., a *Bacillus thuringiensis* insecticidal protein, a PIP-1 polypeptide, and an AflP polypeptide); a herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility. In particular embodiments, polynucleotides encoding iRNA molecules of the invention may be combined with other insect control and disease traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in an Insect Pest

A. Overview

In some embodiments of the invention, at least one nucleic acid molecule useful for the control of insect (e.g., coleopteran and/or hemipteran) pests may be provided to an insect pest, wherein the nucleic acid molecule leads to RNAi-mediated gene silencing in the pest. In particular embodiments, an iRNA molecule (e.g., dsRNA, siRNA, miRNA, shRNA, and hpRNA) may be provided to a coleopteran and/or hemipteran pest. In some embodiments, a nucleic acid molecule useful for the control of insect pests may be provided to a pest by contacting the nucleic acid molecule with the pest. In these and further embodiments, a nucleic acid molecule useful for the control of insect pests may be provided in a feeding substrate of the pest, for example, a nutritional composition. In these and further embodiments, a nucleic acid molecule useful for the control of an insect pest may be provided through ingestion of plant material comprising the nucleic acid molecule that is ingested by the pest. In certain embodiments, the nucleic acid molecule is present in plant material through expression of a recombinant nucleic acid introduced into the plant material, for example, by transformation of a plant cell with a vector comprising the recombinant nucleic acid and regeneration of a plant material or whole plant from the transformed plant cell.

B. RNAi-mediated Target Gene Suppression

In some embodiments, the invention provides iRNA molecules (e.g., dsRNA, siRNA, miRNA, shRNA, and hpRNA) that may be designed to target essential native polynucleotides (e.g., essential genes) in the transcriptome of an insect pest (for example, a coleopteran (e.g., WCR, NCR, and SCR) or hemipteran (e.g., BSB) pest), for example by designing an iRNA molecule that comprises at least one strand comprising a polynucleotide that is specifically complementary to the target polynucleotide. The sequence of an iRNA molecule so designed may be identical to that of the target polynucleotide, or may incorporate mismatches that do not prevent specific hybridization between the iRNA molecule and its target polynucleotide.

iRNA molecules of the invention may be used in methods for gene suppression in an insect (e.g., coleopteran and/or hemipteran) pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding polynucleotide including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In some embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand." The passenger strand may be degraded, and the guide strand may be incorporated into RISC. Post-transcriptional inhibition occurs by specific hybridization of the guide strand with a specifically complementary polynucleotide of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a polynucleotide, which polynucleotide may be expressed in vitro to produce an iRNA molecule that is substantially homologous to a nucleic acid molecule encoded by a polynucleotide within the genome of an insect (e.g., coleopteran and/or hemipteran) pest. In certain embodiments, the in vitro transcribed iRNA molecule may be a stabilized dsRNA molecule that comprises a stem-loop structure. After an insect pest contacts the in vitro transcribed iRNA molecule, post-transcriptional inhibition of a target gene in the pest (for example, an essential gene) may occur.

In some embodiments of the invention, expression of a nucleic acid molecule comprising at least 15 contiguous nucleotides (e.g., at least 19 contiguous nucleotides) of a polynucleotide are used in a method for post-transcriptional inhibition of a target gene in an insect (e.g., coleopteran and/or hemipteran) pest, wherein the polynucleotide is selected from the group consisting of: SEQ ID NO:89; the complement or reverse complement of SEQ ID NO:89; SEQ ID NO:90; the complement or reverse complement of SEQ ID NO:90; SEQ ID NO:91; the complement or reverse complement of SEQ ID NO:91; SEQ ID NO:92; the complement or reverse complement of SEQ ID NO:92; SEQ ID NO:93; the complement or reverse complement of SEQ ID NO:93; SEQ ID NO:94; the complement or reverse complement of SEQ ID NO:94; SEQ ID NO:95; the complement or reverse complement of SEQ ID NO:95; SEQ ID NO:96; the complement or reverse complement of SEQ ID NO:96; SEQ ID NO:97; the complement or reverse complement of SEQ ID NO:97; SEQ ID NO:98; the complement or reverse complement of SEQ ID NO:98; an RNA expressed from a native coding polynucleotide of a *Diabrotica* organism comprising SEQ ID NO:1; the complement or reverse complement of an RNA expressed from a native coding polynucleotide of a *Diabrotica* organism comprising SEQ ID NO:1; an RNA expressed from a native coding polynucleotide of a *Diabrotica* organism comprising SEQ ID NO:3; the complement or reverse complement of an RNA expressed from a native coding polynucleotide of a *Diabrotica* organism comprising SEQ ID NO:3; an RNA expressed from a native coding polynucleotide of a *Diabrotica* organism comprising SEQ ID NO:5; the complement or reverse complement of an RNA expressed from a native coding polynucleotide of a *Diabrotica* organism comprising SEQ ID NO:5; an RNA expressed from a native coding polynucleotide of a *Diabrotica* organism comprising SEQ ID NO:6; the complement or reverse complement of an RNA expressed from a native coding polynucleotide of a *Diabrotica* organism comprising SEQ ID NO:6; an RNA expressed from a native coding polynucleotide of a *Diabrotica* organism comprising SEQ ID NO:7; the complement or reverse complement of an RNA expressed from a native coding polynucleotide of a *Diabrotica* organism comprising SEQ ID NO:7; an RNA expressed from a native coding polynucleotide of a *Diabrotica* organism comprising SEQ ID NO:8; the complement or reverse complement of an RNA expressed from a native coding polynucleotide of a *Diabrotica* organism comprising SEQ ID NO:8; an RNA expressed from a native coding polynucleotide of a *Euschistus heros* organism comprising SEQ ID NO:76; the complement or reverse complement of an RNA expressed from a native coding polynucleotide of a *E. heros* organism comprising SEQ ID NO:76; an RNA expressed from a native coding polynucleotide of a *Euschistus heros* organism comprising SEQ ID NO:78; the complement or reverse complement of an RNA expressed from a native coding polynucleotide of a *E. heros* organism comprising SEQ ID NO:78; an RNA expressed from a native coding polynucleotide of a *Euschistus heros* organism comprising SEQ ID NO:80; the complement or reverse complement of an RNA expressed from a native coding polynucleotide of a *E. heros* organism comprising SEQ ID NO:80; an RNA expressed from a native coding polynucleotide of a *Euschistus heros* organism comprising SEQ ID NO:81; the complement or reverse complement of an RNA expressed from a native coding polynucleotide of a *E. heros* organism comprising SEQ ID NO:81; and RNA molecules comprising at least 15 contiguous nucleotides of any of the foregoing. In certain embodiments, expression of a nucleic acid molecule that is at least about 80% identical (e.g., 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of an insect (e.g., coleopteran and/or hemipteran) pest.

In some embodiments, an iRNA molecule is provided in a nutritional composition referred to herein as an "RNAi bait." An RNAi bait may be formed in particular embodiments when an iRNA molecule (e.g., a dsRNA) is mixed with a food of the target insect, an attractant of the insect, or both. When the insect eats an RNAi bait, the insect may consume the iRNA molecule. An RNAi bait may be, for example and without limitation, a granule, gel, flowable powder, liquid, or solid. In particular embodiments, an iRNA molecule may be incorporated into a bait formulation such as that described in U.S. Pat. No. 8,530,440, the contents of which are incorporated in their entirety herein by this reference. In some examples, an RNAi bait is placed in or around the environment of an insect pest, such that, for example, the pest can come into contact with and/or be attracted to the RNAi bait.

It is an important feature of some embodiments herein that the RNAi post-transcriptional inhibition system is able to tolerate sequence variations among target genes that might be expected due to genetic mutation, strain polymorphism, or evolutionary divergence. The introduced product or a fully-processed mRNA of a target gene, so long as the introduced nuclic acid molecule is specifically hybridizable to either a primary transcription product or a fully-processed mRNA of the target gene. Moreover, the introduced nucleic acid molecule may not need to be full-length, relative to either a primary tranecription product or a fully processed mRNA of the target gene.

Inhibition of a target gene using the iRNA technology of the present invention is sequence-specific; i.e., polynucleotides substantially homologous to the iRNA molecule(s) are targeted for genetic inhibition. In some embodiments, an RNA molecule comprising a polynucleotide with a nucleotide sequence that is identical to that of a portion of a target gene may be used for inhibition. In these and further embodiments, an RNA molecule comprising a polynucleotide with one or more insertion, deletion, and/or point mutations relative to a target polynucleotide may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length polynucleotide exhibiting a greater homology compensates for a longer, less homologous polynucleotide. The length of the polynucleotide of a duplex region of a dsRNA molecule that is identical to a portion of a target gene transcript may be at least about 25, 50, 100, 200, 300, 400, 500, or at least about 1000 bases. Thus, the duplex region of a dsRNA molecule targeting the fsh gene of SEQ ID NO:1 or SEQ ID NO:3 may comprise, for example, about 25 (e.g., 21, 22, 23, 24, 25,26, 27, 28, and 29), about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, or about 1000 contiguous nucleotides of the transcript of any of SEQ ID NO:1, SEQ ID NO: 3, SEQ ID NO:5, SEQ ID NO:6, SEQ ID NO:7, and SEQ ID NO:8, and the complements and reverse complements thereof. In some embodiments, a polynucleotide of 20-100 nucleotides may be used. In particular embodiments, a polynucleotide of 200-300 nucleotides may be used. In particular embodiments, a polynucleotide of 500-1000 nucleotides may be used, depending on the size of the target gene.

In certain embodiments, expression of a target gene in a pest (e.g., coleopteran or hemipteran) may be inhibited by at least 10%; at least 33%; at least 50%; or at least 80% within a cell of the pest, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although, in certain embodiments of the invention, inhibition occurs in substantially all cells of the pest, in other embodiments, inhibition occurs only in a subset of cells expressing the target gene.

In some embodiments, transcriptional suppression is mediated by the presence in a cell of a dsRNA molecule exhibiting substantial sequence identity to a promoter DNA or the complement thereof to effect what is referred to as "promoter trans suppression." Gene suppression may be effective against target genes in an insect pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary polynucleotides in the cells of the insect pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of IRNA Molecules Provided to an Insect Pest

Expression of iRNA molecules for RNAi-mediated gene inhibition in an insect (e.g., coleopteran and/or hemipteran) pest may be carried out in any one of many in vitro or in vivo formats. The iRNA molecules may then be provided to an insect pest, for example, by contacting the iRNA molecules with the pest, or by causing the pest to ingest or otherwise internalize the iRNA molecules. Some embodiments include transformed host plants of a coleopteran and/or hemipteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by an insect pest during feeding, the pest may ingest iRNA molecules expressed in the transgenic plants or cells. The polynucleotides of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in an insect (e.g., coleopteran and/or hemipteran) pest comprises providing in the tissue of the host of the pest a gene-suppressive amount of at least one dsRNA molecule formed following transcription of a polynucleotide as described herein, at least one segment of which is complementary to a mRNA within the cells of the insect pest. A dsRNA molecule, including its modified form such as a siRNA, miRNA, shRNA, or hpRNA molecule, ingested by an insect pest may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from anfsh DNA molecule, for example, comprising a polynucleotide selected from the group consisting of SEQ ID NOs:1, 3, 5-8, 76, 78, 80, and 81. Isolated and substantially purified nucleic acid molecules including, but not limited to, non-naturally occurring polynucleotides and recombinant DNA constructs for providing dsRNA molecules are therefore provided, which suppress or inhibit the expression of an endogenous coding polynucleotide or a target coding polynucleotide in an insect pest when introduced thereto.

Particular embodiments provide a delivery system for the delivery of iRNA molecules for the post-transcriptional inhibition of one or more target gene(s) in an insect (e.g., coleopteran and/or hemipteran) plant pest and control of a population of the plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acids encoding a particular iRNA molecule may be produced by employing recombinant DNA technologies (which basic technologies are well-known in the art) to construct a plant transformation vector comprising a polynucleotide encoding an iRNA molecule of the invention (e.g., a stabilized dsRNA molecule); to transform a plant cell or plant; and to generate the transgenic plant cell or the transgenic plant that contains the transcribed iRNA molecule.

To impart insect (e.g., coleopteran and/or hemipteran) pest protection to a transgenic plant, a recombinant DNA molecule may, for example, be transcribed into an iRNA molecule, such as a dsRNA molecule, a siRNA molecule, a miRNA molecule, a shRNA molecule, or a hpRNA molecule. In some embodiments, an RNA molecule transcribed from a recombinant DNA molecule may form a dsRNA molecule within the tissues or fluids of the recombinant plant. Such a dsRNA molecule may be comprised in part of a polynucleotide that is identical to a corresponding polynucleotide transcribed from a DNA within an insect pest of a type that may infest the host plant. Expression of a target gene within the pest is suppressed by the dsRNA molecule, and the suppression of expression of the target gene in the pest results in the transgenic plant being protected against the pest. The modulatory effects of dsRNA molecules have been shown to be applicable to a variety of genes expressed in pests, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a polynucleotide for use in producing iRNA molecules may be operably linked to one or more promoter elements functional in a plant host cell. The promoter may be an endogenous promoter, normally resident in the host genome. The polynucleotide of the present invention, under the control of an operably linked promoter element, may further be flanked by additional elements that advantageously affect its transcription and/or the stability of a resulting transcript. Such elements may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn plant) caused by an insect (e.g., coleopteran and/or hemipteran) pest that feeds on the plant, wherein the method comprises providing in the host plant a transformed plant cell expressing at least one nucleic acid molecule of the invention, wherein the nucleic acid molecule(s) functions upon being taken up by the pest(s) to inhibit the expression of a target polynucleotide within the pest(s), which inhibition of expression results in mortality and/or reduced growth of the pest(s), thereby reducing the damage to the host plant caused by the pest(s). In some embodiments, the nucleic acid molecule(s) comprise dsRNA molecules. In these and further embodiments, the nucleic acid molecule(s) comprise dsRNA molecules that each comprise more than one polynucleotide that is specifically hybridizable to a nucleic acid molecule expressed in a coleopteran and/or hemipteran pest cell. In some embodiments, the nucleic acid molecule(s) consist of one polynucleotide that is specifically hybridizable to a nucleic acid molecule expressed in an insect pest cell.

In some embodiments, a method for increasing the yield of a corn crop is provided, wherein the method comprises introducing into a corn plant at least one nucleic acid molecule of the invention; cultivating the corn plant to allow the expression of an iRNA molecule comprising the nucleic acid, wherein expression of an iRNA molecule comprising the nucleic acid inhibits insect (e.g., coleopteran and/or hemipteran) pest damage and/or growth, thereby reducing or eliminating a loss of yield due to pest infestation. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in an insect pest cell. In some examples, the nucleic acid molecule(s) comprises a polynucleotide that is specifically hybridizable to a nucleic acid molecule expressed in a coleopteran and/or hemipteran pest cell.

In some embodiments, a method for modulating the expression of a target gene in an insect (e.g., coleopteran and/or hemipteran) pest is provided, the method comprising: transforming a plant cell with a vector comprising a polynucleotide encoding at least one iRNA molecule of the invention, wherein the polynucleotide is operatively-linked to a promoter and a transcription termination element; culturing the transformed plant cell under conditions sufficient to allow for development of a plant cell culture including a plurality of transformed plant cells; selecting for transformed plant cells that have integrated the polynucleotide into their genomes; screening the transformed plant cells for expression of an iRNA molecule encoded by the integrated polynucleotide; selecting a transgenic plant cell that expresses the iRNA molecule; and feeding the selected transgenic plant cell to the insect pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in an insect pest cell. In some examples, the nucleic acid molecule(s) comprises a polynucleotide that is specifically hybridizable to a nucleic acid molecule expressed in a coleopteran and/or hemipteran pest cell.

iRNA molecules of the invention can be incorporated within the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to insect (e.g., coleopteran and/or hemipteran) pests. For example, the iRNA molecules of the invention may be directly introduced into the cells of a pest(s). Methods for introduction may include direct mixing of iRNA with plant tissue from a host for the insect pest(s), as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the insect pests known to infest the plant. iRNA molecules produced by chemical or enzymatic synthesis may also be formulated in a manner consistent with common agricultural practices, and used as spray-on or bait products for controlling plant damage by an insect pest. The formulations may include the appropriate stickers and wetters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from the pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1

Materials and Methods

Sample preparation and bioassays

A number of dsRNA molecules (including those corresponding to fsh-1 reg1 (SEQ ID NO:5), fsh-2 reg1 (SEQ ID NO:6), fsh-1 v I (SEQ ID NO:7), and fsh-1 v2 (SEQ ID NO:8) were synthesized and purified using a MEGASCRIPT® T7 RNAi kit (LIFE TECHNOLOGIES, Carlsbad, CA) or T7 Quick High Yield RNA Synthesis Kit (NEW ENGLAND BIOLABS, Whitby, Ontario). The purified dsRNA molecules were prepared in TE buffer, and all bioassays contained a control treatment consisting of this buffer, which served as a background check for mortality or growth inhibition of WCR (*Diabrotica virgifera virgifera* LeConte). The concentrations of dsRNA molecules in the bioassay buffer were measured using a NANODROP™ 8000 spectrophotometer (THERMO SCIENTIFIC, Wilmington, Del.).

Samples were tested for insect activity in bioassays conducted with neonate insect larvae on artificial insect diet. WCR eggs were obtained from CROP CHARACTERISTICS, INC. (Farmington, Minn.).

The bioassays were conducted in 128-well plastic trays specifically designed for insect bioassays (C-D INTERNATIONAL, Pitman, N.J.). Each well contained approximately 1.0 mL of an artificial diet designed for growth of coleopteran insects. A 60 μL aliquot of dsRNA sample was delivered by pipette onto the surface of the diet of each well (40 μL/$cm^2$). dsRNA sample concentrations were calculated as the amount of dsRNA per square centimeter (ng/$cm^2$) of surface area (1.5 $cm^2$) in the well. The treated trays were held in a fume hood until the liquid on the diet surface evaporated or were absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light:Dark)) for 9 days, after which time the total number of insects exposed to each sample, the number of dead insects, and the weight of surviving insects were recorded. Average percent mortality and average growth inhibition were calculated for each treatment. Growth inhibition (GI) was calculated as follows:

$$GI=[1-(TWIT/TNIT)/(TWIBC/TNIBC)],$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

The statistical analysis was done using JMP™ software (SAS, Cary, N.C.).

The $LC_{50}$ (Lethal Concentration) is defined as the dosage at which 50% of the test insects are killed. The $GI_{50}$ (Growth Inhibition) is defined as the dosage at which the mean growth (e.g. live weight) of the test insects is 50% of the mean value seen in Background Check samples.

Replicated bioassays demonstrated that ingestion of particular samples resulted in a surprising and unexpected mortality and growth inhibition of corn rootworm larvae.

Example 2

Identification of Candidate Target Genes

Insects from multiple stages of WCR (*Diabrotica virgifera virgifera* LeConte) development were selected for pooled transcriptome analysis to provide candidate target gene sequences for control by RNAi transgenic plant insect protection technology.

In one exemplification, total RNA was isolated from about 0.9 gm whole first-instar WCR larvae; (4 to 5 days post-hatch; held at 16° C.), and purified using the following phenol/TRI REAGENT®-based method (MOLECULAR RESEARCH CENTER, Cincinnati, Ohio):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 μL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 gm of larvae yielded over 1 mg of total RNA, with an $A_{260}/A_{280}$ ratio of 1.9. The RNA thus extracted was stored at −80° C. until further processed.

RNA quality was determined by running an aliquot through a 1% agarose gel. The agarose gel solution was made using autoclaved 10× TAE buffer (Tris-acetate EDTA;

1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1× TAE was used as the running buffer. Before use, the electrophoresis tank and the well-forming comb were cleaned with RNaseAway™ (INVITROGEN INC., Carlsbad, Calif.). Two μL of RNA sample were mixed with 8 μL of TE buffer (10 mM Tris HCl pH 7.0; 1 mM EDTA) and 10 μL of RNA sample buffer (NOVAGEN® Catalog No 70606; EMD4 Bioscience, Gibbstown, N.J.). The sample was heated at 70° C. for 3 min, cooled to room temperature, and 5 μL (containing 1 μg to 2 μg RNA) were loaded per well. Commercially available RNA molecular weight markers were simultaneously run in separate wells for molecular size comparison. The gel was run at 60 volts for 2 hrs.

A normalized cDNA library was prepared from the larval total RNA by a commercial service provider (EUROFINS MWG Operon, Huntsville, Ala.), using random priming. The normalized larval cDNA library was sequenced at ½plate scale by GS FLX 454 Titanium™ series chemistry at EUROFINS MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for RNAi targeting were hypothesized to be essential for survival and growth in pest insects. Selected target gene homologs were identified in the transcriptome sequence database, as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit to the non-*Diabrotica* candidate gene sequence present in the *Diabrotica* sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, Sequencher™ v4.9 (GENE CODES CORPORATION, Ann Arbor, Mich.) was used to assemble the sequences into longer contigs.

Several candidate target genes encoding *Diabrotica* fsh (SEQ ID NOs:1 and 3) were identified as genes that may lead to coleopteran pest mortality, inhibition of growth, inhibition of development, and/or inhibition of feeding in WCR.

The fsh gene is a chromatin-binding protein that is involved in activation of homeotic genes.

The sequences SEQ ID NO:1 and 3 are novel. The sequences are not provided in public databases, and are not disclosed in PCT International Patent Publication No. WO/2011/025860; U.S. Patent Application No. 20070124836; U.S. Patent Application No. 20090306189; U.S. Patent Application No. US20070050860; U.S. Patent Application No. 20100192265; U.S. Pat. No. 7,612,194; or U.S. Patent Application No. 2013192256. WCR fsh-1 (SEQ ID NO:1) is somewhat related to a fragment of a sequence from *Orussus abietinus* (GENBANK Accession No. XM_012423491.1). WCR fsh-2 (SEQ ID NO:3) is somewhat related to a fragment of a sequence from *Orussus abietinus* (GENBANK Accession No. XM 012423491.1). The closest homolog of the WCR FSH-1 amino acid sequence (SEQ ID NO:2) is a *Tribolium castaneum* protein having GENBANK Accession No. XP_008198642.1 (79% similar; 73% identical over the homology region). The closest homolog of the WCR F SH-2 amino acid sequence (SEQ ID NO:4) is a *Tribolium castaneum* protein having GENBANK Accession No. XP_008198642.1 (71% similar; 62% identical over the homology region).

Fsh dsRNA transgenes can be combined with other dsRNA molecules, for example, to provide redundant RNAi targeting and RNAi effects. Transgenic corn events expressing dsRNA that targets fsh are useful for preventing root feeding damage by corn rootworm. Fsh dsRNA transgenes represent new modes of action for combining with *Bacillus thuringiensis*, PIP, and/or AflP insecticidal protein technology in Insect Resistance Management gene pyramids to mitigate the development of rootworm populations resistant to either of these rootworm control technologies.

Example 3

Amplification of Target Genes to Produce dsRNA

Full-length or partial clones of sequences of a *Diabrotica* fsh candidate genes were used to generate PCR amplicons for dsRNA synthesis. Primers were designed to amplify portions of coding regions of each target gene by PCR. See Table 1. Where appropriate, a T7 phage promoter sequence (TTAATACGACTCACTATAGGGAGA; SEQ ID NO:9) was incorporated into the 5' ends of the amplified sense or antisense strands. See Table 1. Total RNA was extracted from WCR using TRIzol® (Life Technologies, Grand Island, N.Y.), and was then used to make first-strand cDNA with SuperScriptIII® First-Strand Synthesis System and manufacturers Oligo dT primed instructions (Life Technologies, Grand Island, N.Y.). First-strand cDNA was used as template for PCR reactions using opposing primers positioned to amplify all or part of the native target gene sequence. dsRNA was also amplified from a DNA clone comprising the coding region for a yellow fluorescent protein (YFP) (SEQ ID NO:10; Shagin et al. (2004) Mol. Biol. Evol. 21(5):841-50).

TABLE 1

Primers and Primer Pairs used to amplify portions of coding regions of exemplary fsh target gene and YFP negative control gene.

| Gene ID | Primer ID | Sequence |
|---|---|---|
| Pair 1 fsh-1 | Dvv-fsh-1_For | TTAATACGACTCACTATAGGGAGATCTTCCGTGT CGCTAGAAGAATC (SEQ ID NO: 11) |
| | Dvv-fsh-1_Rev | TTAATACGACTCACTATAGGGAGACAAAAGAAAA ACTACCAGAATCACTG (SEQ ID NO: 12) |
| Pair 2 fsh-2 | Dvv-fsh-2_For | TTAATACGACTCACTATAGGGAGAACTTCCTCGC CATAGCAACC (SEQ ID NO: 13) |
| | Dvv-fsh-2_Rev | TTAATACGACTCACTATAGGGAGAGGTAAAAAAG GGCGTGAAAAGAAAG (SEQ ID NO: 14) |
| Pair 3 fsh-1 v1 | Dvv-fsh-1_v1_For | TTAATACGACTCACTATAGGGAGAGTTCATCGGG AATCTTTGC (SEQ ID NO: 15) |
| | Dvv-fsh-1_v1_Rev | TTAATACGACTCACTATAGGGAGACACTCCTCAA GACTTTGC (SEQ ID NO: 16) |
| Pair 4 fsh-1 v2 | Dvv-fsh-1_v2_For | TTAATACGACTCACTATAGGGAGAACTTCCTCGC CATAGCAACC (SEQ ID NO: 17) |
| | Dvv-fsh-1_v2_Rev | TTAATACGACTCACTATAGGGAGACGACATCATA AAGAAACCGATGGAT (SEQ ID NO: 18) |
| Pair 5 YFP | YFP-F_T7 | TTAATACGACTCACTATAGGGAGACACCATGGGC TCCAGCGGCGCCC (sEQ ID NO: 26) |
| | YFP-R_T7 | TTAATACGACTCACTATAGGGAGAAGATCTTGAA GGCGCTCTTCAGG (SEQ ID NO: 29) |

Example 4

RNAi Constructs

Template preparation by PCR and dsRNA synthesis

Figure 2:
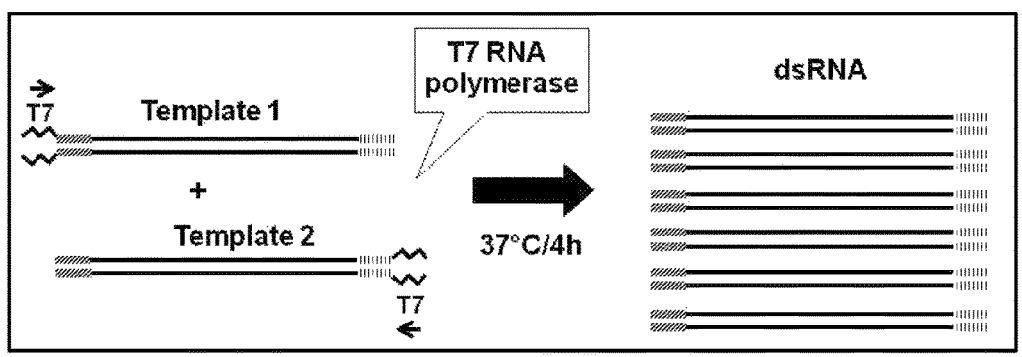
FIG. 2 includes a depiction of a strategy used to generate dsRNA from two transcription templates.

The strategies used to provide specific templates for fsh dsRNA and YFP dsRNA production are shown in FIG. 1 and FIG. 2. Template DNAs intended for use in dsRNA synthesis were prepared by PCR using the primer pairs in Table 1 and (as PCR template) first-strand cDNA prepared from total RNA isolated from WCR eggs, first-instar larvae, or adults. For each selectedlth and YFP target gene region, PCR amplifications introduced a T7 promoter sequence at the 5' ends of the amplified sense and antisense strands (the YFP segment was amplified from a DNA clone of the YFP coding region). The two PCR amplified fragments for each region of the target genes were then mixed in approximately equal amounts, and the mixture was used as transcription template for dsRNA production. See FIG. 1. The sequences of the dsRNA templates amplified with the particular primer pairs were: SEQ ID NO:5 (fsh-1 reg 1), SEQ ID NO:6 (fsh-2 reg 1), SEQ ID NO:7 (fsh-1 v1), SEQ ID NO:8 (fsh-1 v2), and SEQ ID NO:10 (YFP). Double-stranded RNA for insect bioassay was synthesized and purified using an AMBION® MEGASCRIPT® RNAi kit following the manufacturer's instructions (INVITROGEN) or Hi Scribe® T7 In Vitro Transcription Kit following the manufacturer's instructions (New England Biolabs, Ipswich, MA). The concentrations of dsRNAs were measured using a NANODROP™ 8000 spectrophotometer (THERMO SCIENTIFIC, Wilmington, Del.).

Construction of plant transformation vectors

Entry vectors harboring a target gene construct for hairpin formation comprising segments offsh (SEQ ID NOs:1 and 3) were assembled using a combination of chemically synthesized fragments (DNA2.0, Menlo Park, Calif.) and standard molecular cloning methods. Intramolecular hairpin formation by RNA primary transcripts was facilitated by arranging (within a single transcription unit) two copies of thefth target gene segment in opposite orientation to one another, the two segments being separated by a linker polynucleotide (for example and without limitation, a loop (e.g., SEQ ID NO:100), or an ST-LS1 intron (Vancanneyt et al. (1990) Mol. Gen. Genet. 220(2):245-50)). Thus, the primary mRNA transcript contains the twofth gene segment sequences as large inverted repeats of one another, separated by the linker sequence. A copy of a maize ubiquitin 1 promoter (U.S. Pat. No. 5,510,474) was used to drive production of the primary mRNA hairpin transcript, and a fragment comprising a 3' untranslated region from the potato pinII gene (StPinII) was used to terminate transcription of the hairpin-RNA-expressing gene.

The binary destination vector comprised an herbicide tolerance gene (aryloxyalknoate dioxygenase; AAD-1 v3; U.S. Pat. No. 7,838,733(B2), and Wright et al. (2010) Proc. Natl. Acad. Sci. U.S.A. 107:20240-5) under the regulation of a maize ubiquitin 1 promoter (U.S. Pat. No. 5,510,474). A 5'UTR sequence and linker were positioned between the 3' end of the SCBV promoter segment and the start codon of the AAD-1 coding region. A fragment comprising a 3' untranslated region from a maize lipase gene (ZmLip 3'UTR; U.S. Pat. No. 7,179,902) was used to terminate transcription of the AAD-1 mRNA.

A negative control binary vector, which comprises a gene that expresses a YFP protein, is constructed by means of standard GATEWAY® recombination reactions with a typical binary destination vector and entry vector. The binary destination vector comprises a herbicide tolerance gene (aryloxyalknoate dioxygenase; AAD-1 v3) (as above) under the expression regulation of a maize ubiquitin 1 promoter (as above) and a fragment comprising a 3' untranslated region from a maize lipase gene (ZmLip 3'UTR; as above). The entry vector comprises a YFP coding region (SEQ ID NO:19) under the expression control of a maize ubiquitin 1 promoter (as above) and a fragment comprising a 3' untranslated region from a maize peroxidase 5 gene (as above).

Example 5

Screening of Candidate Target Genes

Synthetic dsRNA designed to inhibit target gene sequences identified in EXAMPLE 2 caused mortality and growth inhibition when administered to WCR in diet-based assays.

Replicated bioassays demonstrated that ingestion of dsRNA preparations derived from fsh-1 reg1, fsh-2 reg1, fsh-1 vl, and fsh-1 v2 resulted in mortality and growth inhibition of western corn rootworm larvae. Table 2 shows the results of diet-based feeding bioassays of WCR larvae following 9-day exposure to fsh-1 reg1, fsh-2 reg1, fsh-1 vl, and fsh-1 v2 dsRNA, as well as the results obtained with a negative control sample of dsRNA prepared from a yellow fluorescent protein (YFP) coding region (SEQ ID NO:10). Table 3 shows the LC$_{50}$ and GI$_{50}$ results of exposure to fsh-1 vl and fsh-1 v2 dsRNA.

TABLE 2

Results of fsh dsRNA diet feeding assays obtained with western corn rootworm larvae after 9 days of feeding. ANOVA analysis found significance differences in Mean % Mortality and Mean % Growth Inhibition (GI). Means were separated using the Tukey-Kramer test.

| Gene Name | Dose (ng/cm$^2$) | N | Mean (% Mortality) ± SEM* | Mean (GI) ± SEM |
|---|---|---|---|---|
| fsh-1 Reg1 | 500 | 8 | 68.66 ± 5.34 (A) | 0.75 ± 0.08 (A) |
| fsh-2 Reg1 | 500 | 8 | 69.71 ± 7.24 (A) | 0.81 ± 0.07 (A) |
| fsh-1 vl | 500 | 20 | 67.58 ± 3.42 (A) | 0.83 ± 0.02 (A) |
| fsh-1 v2 | 500 | 20 | 73.84 ± 3.89 (A) | 0.89 ± 0.02 (A) |
| TE** | 0 | 28 | 15.47 ± 2.58 (B) | 0.07 ± 0.04 (B) |
| WATER | 0 | 23 | 13.39 ± 2.09 (B) | −0.03 ± 0.05 (B) |
| YFP*** | 500 | 24 | 11.05 ± 1.80 (B) | 0.03 ± 0.03 (B) |

*SEM = Standard Error of the Mean. Letters in parentheses designate statistical levels. Levels not connected by same letter are significantly different (P < 0.05).
**TE = Tris HCl (1 mM) plus EDTA (0.1 mM) buffer, pH 7.2.
***YFP = Yellow Fluorescent Protein

TABLE 3

Summary of oral potency of fsh dsRNA on WCR larvae (ng/cm$^2$).

| Gene Name | LC$_{50}$ | Range | GI$_{50}$ | Range |
|---|---|---|---|---|
| fsh-1 vl | 107.2 | 78.73-149.14 | 17.51 | 12.22-25.10 |
| fsh-1 v2 | 56.82 | 42.32-76.72 | 9.85 | 6.83-14.20 |

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,612,194, which discloses 9,112 sequences. However, it was determined that many genes suggested to have utility for RNAi-mediated insect control are not efficacious in controlling *Diabrotica*. It was also determined that sequence fsh-1 reg1, reg1, fsh-1 vl, and fsh-1 v2 dsRNA provide surprising and unexpected superior control of *Diabrotica*, compared to other genes suggested to have utility for RNAi-mediated insect control.

For example, annexin, beta spectrin 2, and mtRP-L4 were each suggested in U.S. Pat. No. 7,612,194 to be efficacious in RNAi-mediated insect control. SEQ ID NO:20 is the DNA sequence of annexin region 1 (Reg 1) and SEQ ID NO:21 is the DNA sequence of annexin region 2 (Reg 2). SEQ ID NO:22 is the DNA sequence of beta spectrin 2 region 1 (Reg 1) and SEQ ID NO:23 is the DNA sequence of beta spectrin 2 region 2 (Reg2). SEQ ID NO:24 is the DNA sequence of mtRP-L4 region 1 (Reg 1) and SEQ ID NO:25 is the DNA sequence of mtRP-L4 region 2 (Reg 2). A YFP sequence (SEQ ID NO:10) was also used to produce dsRNA as a negative control.

Each of the aforementioned sequences was used to produce dsRNA by the methods of EXAMPLE 3. The strategy used to provide specific templates for dsRNA production is shown in FIG. 2. Template DNAs intended for use in dsRNA synthesis were prepared by PCR using the primer pairs in Table 4 and (as PCR template) first-strand cDNA prepared from total RNA isolated from WCR first-instar larvae. (YFP was amplified from a DNA clone.) For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. See FIG. 2. Double-stranded RNA was synthesized and purified using an AMBION® MEGAscript® RNAi kit following the manufacturer's instructions (INVITROGEN). The concentrations of dsRNAs were measured using a NANODROP™ 8000 spectrophotometer (THERMO SCIENTIFIC, Wilmington, Del.) and the dsRNAs were each tested by the same diet-based bioassay methods described above. Table 4 lists the sequences of the primers used to produce the annexin Reg1, annexin Reg2, beta spectrin 2 Reg1, beta spectrin 2 Reg2, mtRP-L4 Reg1, mtRP-L4 Reg2, and YFP dsRNA molecules. Table 5 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, water, or YFP protein.

TABLE 4

Primers and Primer Pairs used to amplify portions of coding regions of genes.

| | Gene (Region) | Primer ID | Sequence |
|---|---|---|---|
| Pair 6 | YFP | YFP-F_T7 | TTAATACGACTCACTATAGGGAGACACCATGGGCTC CAGCGGCGCCC (SEQ ID NO: 26) |
| | YFP | YFP-R | AGATCTTGAAGGCGCTCTTCAGG (SEQ ID NO: 27) |
| Pair 7 | YFP | YFP-F | CACCATGGGCTCCAGCGGCGCCC (SEQ ID NO: 28) |
| | YFP | YFP-R_T7 | TTAATACGACTCACTATAGGGAGAAGATCTTGAAGG CGCTCTTCAGG (SEQ ID NO: 29) |

TABLE 4-continued

Primers and Primer Pairs used to amplify portions of coding regions of genes.

| | Gene (Region) | Primer ID | Sequence |
|---|---|---|---|
| Pair 8 | annexin (Reg 1) | Ann-F1_T7 | TTAATACGACTCACTATAGGGAGAGCTCCAACAGTG GTTCCTTATC (SEQ ID NO: 30) |
| | annexin (Reg 1) | Ann-R1 | CTAATAATTCTTTTTTAATGTTCCTGAGG (SEQ ID NO: 31) |
| Pair 9 | annexin (Reg 1) | Ann-F1 | GCTCCAACAGTGGTTCCTTATC (SEQ ID NO: 32) |
| | annexin (Reg 1) | Ann-R1_T7 | TTAATACGACTCACTATAGGGAGACTAATAATTCTT TTTTAATGTTCCTGAGG (SEQ ID NO: 33) |
| Pair 10 | annexin (Reg 2) | Ann-F2_T7 | TTAATACGACTCACTATAGGGAGATTGTTACAAGCT GGAGAACTTCTC (SEQ ID NO: 34) |
| | annexin (Reg 2) | Ann-R2 | CTTAACCAACAACGGCTAATAAGG (SEQ ID NO: 35) |
| Pair 11 | annexin (Reg 2) | Ann-F2 | TTGTTACAAGCTGGAGAACTTCTC (SEQ ID NO: 36) |
| | annexin (Reg 2) | Ann-R2T7 | TTAATACGACTCACTATAGGGAGACTTAACCAACAA CGGCTAATAAGG (SEQ ID NO: 37) |
| Pair 12 | beta-spect2 (Reg 1) | Betasp2-F1_T7 | TTAATACGACTCACTATAGGGAGAAGATGTTGGCTG CATCTAGAGAA (SEQ ID NO: 38) |
| | beta-spect2 (Reg 1) | Betasp2-R1 | GTCCATTCGTCCATCCACTGCA (SEQ ID NO: 39) |
| Pair 13 | beta-spect2 (Reg 1) | Betasp2-F1 | AGATGTTGGCTGCATCTAGAGAA (SEQ ID NO: 40) |
| | beta-spect2 (Reg 1) | Betasp2-R1_T7 | TTAATACGACTCACTATAGGGAGAGTCCATTCGTCC ATCCACTGCA (SEQ ID NO: 41) |
| Pair 14 | beta-spect2 (Reg 2) | Betasp2-F2_T7 | TTAATACGACTCACTATAGGGAGAGCAGATGAACAC CAGCGAGAAA (SEQ ID NO: 42) |
| | beta-spect2 (Reg 2) | Betasp2-R2 | CTGGGCAGCTTCTTGTTTCCTC (SEQ ID NO: 43) |
| Pair 15 | beta-spect2 (Reg 2) | Betasp2-F2 | GCAGATGAACACCAGCGAGAAA (SEQ ID NO: 44) |
| | beta-spect2 (Reg 2) | Betasp2-R2_T7 | TTAATACGACTCACTATAGGGAGACTGGGCAGCTTC TTGTTTCCTC (SEQ ID NO: 45) |
| Pair 16 | mtRP-L4 (Reg 1) | L4-F1_T7 | TTAATACGACTCACTATAGGGAGAAGTGAAATGTTA GCAAATATAACATCC (SEQ ID NO: 46) |
| | mtRP-L4 (Reg 1) | L4-R1 | ACCTCTCACTTCAAATCTTGACTTTG (SEQ ID NO: 47) |
| Pair 17 | mtRP-L4 (Reg 1) | L4-F1 | AGTGAAATGTTAGCAAATATAACATCC (SEQ ID NO: 48) |
| | mtRP-L4 (Reg 1) | L4-R1_T7 | TTAATACGACTCACTATAGGGAGAACCTCTCACTTC AAATCTTGACTTTG (SEQ ID NO: 49) |
| Pair 18 | mtRP-L4 (Reg 2) | L4-F2_T7 | TTAATACGACTCACTATAGGGAGACAAAGTCAAGAT TTGAAGTGAGAGGT (SEQ ID NO: 50) |
| | mtRP-L4 (Reg 2) | L4-R2 | CTACAAATAAAACAAGAAGGACCCC (SEQ ID NO: 51) |
| Pair 19 | mtRP-L4 (Reg 2) | L4-F2 | CAAAGTCAAGATTTGAAGTGAGAGGT (SEQ ID NO: 52) |
| | mtRP-L4 (Reg 2) | L4-R2_T7 | TTAATACGACTCACTATAGGGAGACTACAAATAAAA CAAGAAGGACCCC (SEQ ID NO: 53) |

TABLE 5

Results of diet feeding assays obtained with western corn rootworm larvae after 9 days.

| Gene Name | Dose (ng/cm$^2$) | Mean Live Larval Weight (mg) | Mean % Mortality | Mean Growth Inhibition |
|---|---|---|---|---|
| annexin-Reg 1 | 1000 | 0.545 | 0 | −0.262 |
| annexin-Reg 2 | 1000 | 0.565 | 0 | −0.301 |
| beta spectrin2 Reg 1 | 1000 | 0.340 | 12 | −0.014 |
| beta spectrin2 Reg 2 | 1000 | 0.465 | 18 | −0.367 |
| mtRP-L4 Reg 1 | 1000 | 0.305 | 4 | −0.168 |
| mtRP-L4 Reg 2 | 1000 | 0.305 | 7 | −0.180 |
| TE buffer* | 0 | 0.430 | 13 | 0.000 |
| Water | 0 | 0.535 | 12 | 0.000 |
| YFP** | 1000 | 0.480 | 9 | −0.386 |

*TE = Tris HCl (10 mM) plus EDTA (1 mM) buffer, pH 8.
**YFP = Yellow Fluorescent Protein Example 6

Production of Transgenic Maize Tissues Comprising Insecticidal dsRNAs

*Agrobacterium*-mediated Transformation. Transgenic maize cells, tissues, and plants that produce one or more insecticidal dsRNA molecules (for example, at least one dsRNA molecule including a dsRNA molecule targeting a gene comprising fsh (e.g., SEQ ID NOs:1 and 3)) through expression of a chimeric gene stably-integrated into the plant genome were produced following *Agrobacterium*-mediated transformation. Maize transformation methods employing superbinary or binary transformation vectors are known in the art, as described, for example, in U.S. Pat. No. 8,304,604, which is herein incorporated by reference in its entirety. Transformed tissues were selected by their ability to grow on Haloxyfop-containing medium and were screened for dsRNA production, as appropriate. Portions of such transformed tissue cultures may be presented to neonate corn rootworm larvae for bioassay, essentially as described in EXAMPLE 1.

*Agrobacterium* Culture Initiation. Glycerol stocks of *Agrobacterium* strain DAt13192 cells (PCT International Publication No. WO 2012/016222A2) harboring a binary transformation vector described above (EXAMPLE 4) were streaked on AB minimal medium plates (Watson, et al. (1975) J. Bacteriol. 123:255-264) containing appropriate antibiotics, and were grown at 20° C. for 3 days. The cultures were then streaked onto YEP plates (gm/L: yeast extract, 10; Peptone, 10; NaCl, 5) containing the same antibiotics and were incubated at 20° C. for 1 day.

*Agrobacterium* culture. On the day of an experiment, a stock solution of Inoculation Medium and acetosyringone was prepared in a volume appropriate to the number of constructs in the experiment and pipetted into a sterile, disposable, 250 mL flask. Inoculation Medium (Frame et al. (2011) *Genetic Transformation Using Maize Immature Zygotic Embryos*. IN Plant Embryo Culture Methods and Protocols: Methods in Molecular Biology. T. A. Thorpe and E. C. Yeung, (Eds), Springer Science and Business Media, LLC. pp 327-341) contained: 2.2 gm/L MS salts; 1X ISU Modified MS Vitamins (Frame et al., ibid.) 68.4 gm/L sucrose; 36 gm/L glucose; 115 mg/L L-proline; and 100 mg/L myo-inositol; at pH 5.4.) Acetosyringone was added to the flask containing Inoculation Medium to a final concentration of 200 µM from a 1 M stock solution in 100% dimethyl sulfoxide, and the solution was thoroughly mixed.

For each construct, 1 or 2 inoculating loops-full of *Agrobacterium* from the YEP plate were suspended in 15 mL Inoculation Medium/acetosyringone stock solution in a sterile, disposable, 50 mL centrifuge tube, and the optical density of the solution at 550 nm (OD$_{550}$) was measured in a spectrophotometer. The suspension was then diluted to OD$_{550}$ of 0.3 to 0.4 using additional Inoculation Medium/acetosyringone mixtures. The tube of *Agrobacterium* suspension was then placed horizontally on a platform shaker set at about 75 rpm at room temperature and shaken for 1 to 4 hours while embryo dissection was performed.

Ear sterilization and embryo isolation. Maize immature embryos were obtained from plants of *Zea mays* inbred line B104 (Hallauer et al. (1997) Crop Science 37:1405-1406), grown in the greenhouse and self- or sib-pollinated to produce ears. The ears were harvested approximately 10 to 12 days post-pollination. On the experimental day, de-husked ears were surface-sterilized by immersion in a 20% solution of commercial bleach (ULTRA CLOROX® Germicidal Bleach, 6.15% sodium hypochlorite; with two drops of TWEEN 20) and shaken for 20 to 30 min, followed by three rinses in sterile deionized water in a laminar flow hood. Immature zygotic embryos (1.8 to 2.2 mm long) were aseptically dissected from each ear and randomly distributed into microcentrifuge tubes containing 2.0 mL of a suspension of appropriate *Agrobacterium* cells in liquid Inoculation Medium with 200 µM acetosyringone, into which 2 µL of 10% BREAK-THRU® 5233 surfactant (EVONIK INDUSTRIES; Essen, Germany) was added. For a given set of experiments, embryos from pooled ears were used for each transformation.

*Agrobacterium* co-cultivation. Following isolation, the embryos were placed on a rocker platform for 5 minutes. The contents of the tube were then poured onto a plate of Co-cultivation Medium, which contained 4.33 gm/L MS salts; 1X ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L AgNO$_3$; 200 µM acetosyringone in DMSO; and 3 gm/L GELZAN™, at pH 5.8. The liquid *Agrobacterium* suspension was removed with a sterile, disposable, transfer pipette. The embryos were then oriented with the scutellum facing up using sterile forceps with the aid of a microscope. The plate was closed, sealed with 3M™ MICROPORE™ medical tape, and placed in an incubator at 25° C. with continuous light at approximately 60 µmol m$^{-2}$s$^{-1}$ of Photosynthetically Active Radiation (PAR).

Callus Selection and Regeneration of Transgenic Events. Following the Co-Cultivation period, embryos were transferred to Resting Medium, which was composed of 4.33 gm/L MS salts; 1X ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L AgNO$_3$; 0.5 gm/L MES (2-(N-morpholino) ethanesulfonic acid monohydrate; PHYTOTECHNOLOGIES LABR.; Lenexa, Kans.); 250 mg/L Carbenicillin; and 2.3 gm/L GELZAN™; at pH 5.8. No more than 36 embryos were moved to each plate. The plates were placed in a clear plastic box and incubated at 27° C. with continuous light at approximately 50 µmol m$^{-2}$s$^{-1}$ PAR for 7 to 10 days. Callused embryos were then transferred (<18/plate) onto Selection Medium I, which was comprised of Resting Medium (above) with 100 nM R-Haloxyfop acid (0.0362 mg/L; for selection of calli harboring the AAD-1 gene). The plates were returned to clear boxes and incubated at 27° C. with continuous light at approximately 50 µmol m$^{-2}$s$^{-1}$ PAR for 7 days. Callused embryos were then transferred (<12/plate) to Selection Medium II, which was comprised of Resting Medium (above) with 500 nM R-Haloxyfop acid (0.181 mg/L). The plates were returned to clear boxes and incubated at 27° C. with continuous light at approximately 50 µmol m$^{-2}$s$^{-1}$ PAR for 14 days. This selection step allowed transgenic callus to further proliferate and differentiate.

Proliferating, embryogenic calli were transferred (<9/plate) to Pre-Regeneration medium. Pre-Regeneration Medium contained 4.33 gm/L MS salts; 1X ISU Modified MS Vitamins; 45 gm/L sucrose; 350 mg/L L-proline; 100 mg/L myo-inositol; 50 mg/L Casein Enzymatic Hydrolysate; 1.0 mg/L AgNO$_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 0.181 mg/L Haloxyfop acid; at pH 5.8. The plates were stored in clear boxes and incubated at 27° C. with continuous light at approximately 50 µmol m$^{-2}$s$^{-1}$ PAR for 7 days. Regenerating calli were then transferred (<6/plate) to Regeneration Medium in PHYTATRAYS™ (SIGMA-ALDRICH) and incubated at 28° C. with 16 hours light/8 hours dark per day (at approximately 160 µmol m$^{-2}$s$^{-1}$ PAR) for 14 days or until shoots and roots developed. Regeneration Medium contained 4.33 gm/L MS salts; 1X ISU Modified MS Vitamins; 60 gm/L sucrose; 100 mg/L myo-inositol; 125 mg/L Carbenicillin; 3 gm/L GELLAN™ gum; and 0.181 mg/L R-Haloxyfop acid; at pH 5.8. Small shoots with primary roots were then isolated and transferred to Elongation Medium without selection. Elongation Medium contained 4.33 gm/L MS salts; 1X ISU Modified MS Vitamins; 30 gm/L sucrose; and 3.5 gm/L GELRITE™: at pH 5.8.

Transformed plant shoots selected by their ability to grow on medium containing Haloxyfop were transplanted from PHYTATRAYS™ to small pots filled with growing medium (PROMIX BX; PREMIER TECH HORTICULTURE), covered with cups or HUMI-DOMES (ARCO PLASTICS), and then hardened-off in a CONVIRON growth chamber (27° C. day/24° C. night, 16-hour photoperiod, 50-70% RH, 200 µmol m$^{-2}$5$^{-1}$ PAR). In some instances, putative transgenic plantlets were analyzed for transgene relative copy number by quantitative real-time PCR assays using primers designed to detect the AAD 1 herbicide tolerance gene integrated into the maize genome. Further, qPCR assays were used to detect the presence of the linker and/or target sequence in putative transformants. Selected transformed plantlets were then moved into a greenhouse for further growth and testing.

Transfer and establishment of T$_0$ plants in the greenhouse for bioassay and seed production. When plants reached the V3-V4 stage, they were transplanted into IE CUSTOM BLEND (PROFILE/METRO MIX 160) soil mixture and grown to flowering in the greenhouse (Light Exposure Type: Photo or Assimilation; High Light Limit: 1200 PAR; 16-hour day length; 27° C. day/24° C. night).

Plants to be used for insect bioassays were transplanted from small pots to TINUS™ 350-4 ROOTRAINERS® (SPENCER-LEMAIRE INDUSTRIES, Acheson, Alberta, Canada) (one plant per event per)ROOTRAINER®. Approximately four days after transplanting to ROOTRAINERS®, plants were infested for bioassay.

Plants of the T$_1$ generation are obtained by pollinating the silks of To transgenic plants with pollen collected from plants of non-transgenic elite inbred line B104 or other appropriate pollen donors, and planting the resultant seeds. Reciprocal crosses are performed when possible.

Example 7

Molecular Analyses of Transgenic Maize Tissues

Molecular analyses (e.g. RT-qPCR) of maize tissues were performed on samples from leaves collected from greenhouse grown plants on the same days that root feeding damage was assessed.

Results of RT-qPCR assays for the target were used to validate expression of the transgenes. Results of RT-qPCR assays for the linker polynucleotide in expressed RNAs were used to validate the presence of the transcripts. Transgene RNA expression levels were measured relative to the RNA levels of an endogenous maize gene.

DNA qPCR analyses to detect a portion of the AAD1 coding region in gDNA were used to estimate transgene insertion copy number. Samples for these analyses were collected from plants grown in environmental chambers. Results were compared to DNA qPCR results of assays designed to detect a portion of a single-copy native gene, and simple events (having one or two copies offsh transgenes) were advanced for further studies in the greenhouse.

Additionally, qPCR assays designed to detect a portion of the spectinomycin-resistance gene (SpecR; harbored on the binary vector plasmids outside of the T-DNA) were used to determine if the transgenic plants contain extraneous integrated plasmid backbone sequences.

RNA transcript expression level: target qPCR. Callus cell events or transgenic plants were analyzed by real time quantitative PCR (qPCR) of the target sequence to determine the relative expression level of the full length hairpin transcript, as compared to the transcript level of an internal maize gene (for example, GENBANK Accession No. BT069734), which encodes a TIP41-like protein (i.e. a maize homolog of GENBANK Accession No. AT4G34270; having a tBLASTX score of 74% identity; SEQ ID NO:54). RNA was isolated using an NORGEN BioTek® Total RNA Isolation Kit (NORGEN, Thorold, ON). The total RNA was subjected to an On Column DNaseI treatment according to the kit's suggested protocol. The RNA was then quantified on a NANODROP 8000 spectrophotometer (THERMO SCIENTIFIC) and the concentration was normalized to 50 ng/µL. First strand cDNA was prepared using a HIGH CAPACITY cDNA SYNTHESIS KIT (INVITROGEN) in a 10 µL reaction volume with 5µL denatured RNA, substantially according to the manufacturer's recommended protocol. The protocol was modified slightly to include the addition of 10 µL of 100 µM T2OVN oligonucleotide (IDT) (TTTTTTTTTTTTTTTTTTTTVN, where V is A, C, or G, and N is A, C, G, or T; SEQ ID NO:55) into the 1 mL tube of random primer stock mix, in order to prepare a working stock of combined random primers and oligo dT.

Following cDNA synthesis, samples were diluted 1:3 with nuclease-free water, and stored at −20° C. until assayed.

Separate real-time PCR assays for the target gene and TIP41-like transcript were performed on a LIGHTCYCLER™ 480 (ROCHE DIAGNOSTICS, Indianapolis, IN) in 10 reaction volumes. For the target gene assay, reactions were run with Primers Fsh-2v1 (F) (SEQ ID NO:56) and Fsh-2v1 (R) (SEQ ID NO:57), and an IDT Custom Oligo probe Fsh-2v1 PRB Setl (SEQ ID NO:99), labeled with FAM and double quenched with Zen and Iowa Black quenchers. For the TIP41-like reference gene assay, primers TIPmxF (SEQ ID NO:58) and TIPmxR (SEQ ID NO:59), and Probe HXTIP (SEQ ID NO:60) labeled with HEX (hexachlorofluorescein) were used.

All assays included negative controls of no-template (mix only). For the standard curves, a blank (water in source well) was also included in the source plate to check for sample cross-contamination. Primer and probe sequences are set forth in Table 6. Reaction components recipes for detection of the various transcripts are disclosed in Table 7, and PCR reactions conditions are summarized in Table 8. The FAM (6-Carboxy Fluorescein Amidite) fluorescent moiety was excited at 465 nm and fluorescence was measured at 510 nm; the corresponding values for the HEX (hexachlorofluorescein) fluorescent moiety were 533 nm and 580 nm.

with the base value of 2 being selected under the assumption that, for optimized PCR reactions, the product doubles every cycle.

Transcript size and integrity: Northern Blot Assay. In some instances, additional molecular characterization of the transgenic plants is obtained by the use of Northern Blot (RNA blot) analysis to determine the molecular size of the fsh hairpin dsRNA in transgenic plants expressing an fsh dsRNA.

All materials and equipment are treated with RNaseZAP (AMBION/INVITROGEN) before use. Tissue samples (100 mg to 500 mg) are collected in 2 mL SAFELOCK EPPENDORF tubes, disrupted with a KLECKO™ tissue pulverizer (GARCIA MANUFACTURING, Visalia, Calif.) with three tungsten beads in 1 mL TRIZOL (INVITROGEN) for 5 min, then incubated at room temperature (RT) for 10 min. Optionally, the samples are centrifuged for 10 min at 4° C. at 11,000 rpm and the supernatant is transferred into a fresh 2 mL SAFELOCK EPPENDORF tube. After 200 µL chloroform are added to the homogenate, the tube is mixed by inversion for 2 to 5 min, incubated at RT for 10 minutes, and centrifuged at 12,000×g for 15 min at 4° C. The top phase is transferred into a sterile 1.5 mL EPPENDORF tube, 600 µL of 100% isopropanol are added, followed by incubation at RT for 10 min to 2 hr, and then centrifuged at 12,000×g for 10 min at 4° C. to 25° C. The supernatant is discarded and the RNA pellet is washed twice with 1 mL 70% ethanol, with centrifugation at 7,500×g for 10 min at 4° C. to 25° C. between washes. The ethanol is discarded and the pellet is briefly air dried for 3 to 5 min before resuspending in 50 µL of nuclease-free water.

Total RNA is quantified using the NANODROP 8000® (THERMO-FISHER) and samples are normalized to 5 µg/10 µL. 10 µL of glyoxal (AMBION/INVITROGEN) are then added to each sample. Five to 14 ng of DIG RNA standard marker mix (ROCHE APPLIED SCIENCE, Indianapolis, IN) are dispensed and added to an equal volume of glyoxal. Samples and marker RNAs are denatured at 50° C. for 45 min and stored on ice until loading on a 1.25% SEAKEM GOLD agarose (LONZA, Allendale, N.J.) gel in NORTHERNMAX 10×glyoxal running buffer (AMBION/INVITROGEN). RNAs are separated by electrophoresis at 65 volts/30 mA for 2 hours and 15 minutes.

Following electrophoresis, the gel is rinsed in 2×SSC for 5 min and imaged on a GEL DOC station (BIORAD, Hercules, Calif.), then the RNA is passively transferred to a nylon membrane (MILLIPORE) overnight at RT, using

TABLE 6

Oligonucleotide sequences used for molecular analyses of transcript levels in transgenic maize.

| Target | Oligonucleotide | Sequence |
|---|---|---|
| Fsh | Fsh-2v1 (F) | GTGGTCAGAAGGGTTGTACTT (SEQ ID NO: 56) |
| Fsh | Fsh-2v1 (R) | GAGTATCGCACTCCTCAAGAC (SEQ ID NO: 57) |
| Fsh | Fsh-2v1 PRB Set1 | /56-FAM/AATCAGTCT/ZEN/AACGTCGGCGGCAAA/3IABkFQ/ (SEQ ID NO: 99) |
| TIP41 | TIPmxF | TGAGGGTAATGCCAACTGGTT (SEQ ID NO: 58) |
| TIP41 | TIPmxR | GCAATGTAACCGAGTGTCTCTCAA (SEQ ID NO: 59) |
| TIP41 | HXTIP (HEX-Probe) | TTTTTGGCTTAGAGTTGATGGTGTACTGATGA (SEQ ID NO: 60) |

*TIP41-like protein.

TABLE 7

PCR reaction recipes for transcript detection.

| Component | Target Gene Final Concentration | TIP-like Gene Final Concentration |
|---|---|---|
| Roche Buffer | 1X | 1X |
| Fsh-2v1 (F) | 0.4 µM | 0 |
| Fsh-2v1 (R) | 0.4 µM | 0 |
| Fsh-2v1 PRB Set1 | 0.2 µM | 0 |
| HEXtipZM F | 0 | 0.4 µM |
| HEXtipZM R | 0 | 0.4 µM |
| HEXtipZMP (HEX) | 0 | 0.2 µM |
| cDNA (2.0 µL) | NA | NA |
| Water | To 10 µL | To 10 µL |

TABLE 8

Thermocycler conditions for RNA qPCR.
Target Gene and TIP41-like Gene Detection

| Process | Temp. | Time | No. Cycles |
|---|---|---|---|
| Target Activation | 95° C. | 10 min | 1 |
| Denature | 95° C. | 10 sec | 40 |
| Extend | 60° C. | 40 sec | |
| Acquire FAM or HEX | 72° C. | 1 sec | |
| Cool | 40° C. | 10 sec | 1 |

Data were analyzed using LIGHTCYCLER™ Software v1.5 by relative quantification using a second derivative max algorithm for calculation of Cq values according to the supplier's recommendations. For expression analyses, expression values were calculated using the ΔΔCt method (i.e., 2-(Cq TARGET-Cq REF)), which relies on the comparison of differences of Cq values between two targets, 10×SSC as the transfer buffer (20×SSC consists of 3 sodium chloride and 300 mM trisodium citrate, pH 7.0). Following the transfer, the membrane is rinsed in 2×SSC for 5 minutes, the RNA is UV-crosslinked to the membrane (AGILENT/STRATAGENE), and the membrane is allowed to dry at room temperature for up to 2 days.

The membrane is pre-hybridized in ULTRAHYB™ buffer (AMBION/INVITROGEN) for 1 to 2 hr. The probe consists of a PCR amplified product containing the sequence of interest, (for example, the antisense sequence portion of SEQ ID NOs:5-8, as appropriate) labeled with digoxygenin by means of a ROCHE APPLIED SCIENCE DIG procedure. Hybridization in recommended buffer is overnight at a temperature of 60° C. in hybridization tubes. Following hybridization, the blot is subjected to DIG washes, wrapped, exposed to film for 1 to 30 minutes, then the film is developed, all by methods recommended by the supplier of the DIG kit.

Transgene copy number determination. Maize leaf pieces approximately equivalent to 2 leaf punches were collected in 96-well collection plates (QIAGEN). Tissue disruption was performed with a KLECKO™ tissue pulverizer (GARCIA MANUFACTURING, Visalia, Calif.) in BIOSPRINT96 API lysis buffer (supplied with a BIOSPRINT96 PLANT KIT; QIAGEN) with one stainless steel bead. Following tissue maceration, gDNA was isolated in high throughput format using a BIOSPRINT96 PLANT KIT and a BIOSPRINT96 extraction robot. gDNA was diluted 1:3 DNA:water prior to setting up the qPCR reaction.

qPCR analysis. Transgene detection by hydrolysis probe assay was performed by real-time PCR using a LIGHTCYCLER® 480 system. Oligonucleotides used in hydrolysis probe assays to detect the target gene, the linker sequence (e.g., the loop), or to detect a portion of the SpecR gene (i.e. the spectinomycin resistance gene borne on the binary vector plasmids; SEQ ID NO:61; SPC1 oligonucleotides in Table 9), were designed using LIGHTCYCLER® PROBE DESIGN SOFTWARE 2.0. Further, oligonucleotides used in hydrolysis probe assays to detect a segment of the AAD-1 herbicide tolerance gene (SEQ ID NO:62; GAAD1 oligonucleotides in Table 9) were designed using PRIMER EXPRESS software (APPLIED BIOSYSTEMS). Table 9 shows the sequences of the primers and probes. Assays were multiplexed with reagents for an endogenous maize chromosomal gene (Invertase (SEQ ID NO:63; GENBANK Accession No: U16123; referred to herein as IVR1), which served as an internal reference sequence to ensure gDNA was present in each assay. For amplification, LIGHTCYCLER®480 PROBES MASTER mix (ROCHE APPLIED SCIENCE) was prepared at 1×final concentration in a 10 µL volume multiplex reaction containing 0.4 µM of each primer and 0.2 µM of each probe (Table 10). A two-step amplification reaction was performed as outlined in Table 11. Fluorophore activation and emission for the FAM- and HEX-labeled probes were as described above; CY5 conjugates were excited maximally at 650 nm and fluoresce maximally at 670 nm.

Cp scores (the point at which the fluorescence signal crosses the background threshold) were determined from the real time PCR data using the fit points algorithm (LIGHTCYCLER® SOFTWARE release 1.5) and the Relative Quant module (based on the ΔΔCt method). Data were handled as described previously (above; qPCR).

TABLE 9

Sequences of primers and probes (with fluorescent conjugate) used for gene copy number determinations and binary vector plasmid backbone detection.

| Name | Sequence |
|---|---|
| GAAD1-F | TGTTCGGTTCCCTCTACCAA (SEQ ID NO: 64) |
| GAAD1-R | CAACATCCATCACCTTGACTGA (SEQ ID NO: 65) |
| GAAD1-P (FAM) | CACAGAACCGTCGCTTCAGCAACA (SEQ ID NO: 66) |
| IVR1-F | TGGCGGACGACGACTTGT (SEQ ID NO: 67) |
| IVR1-R | AAAGTTTGGAGGCTGCCGT (SEQ ID NO: 68) |
| IVR1-P (HEX) | CGAGCAGACCGCCGTGTACTTCTACC (SEQ ID NO: 69) |
| SPC1A | CTTAGCTGGATAACGCCAC (SEQ ID NO: 70) |
| SPC1S | GACCGTAAGGCTTGATGAA (SEQ ID NO: 71) |
| TQSPEC (CY5*) | CGAGATTCTCCGCGCTGTAGA (SEQ ID NO: 72) |
| Loop-F | GGAACGAGCTGCTTGCGTAT (SEQ ID NO: 73) |
| Loop-R | CACGGTGCAGCTGATTGATG (SEQ ID NO: 74) |
| Loop-P (FAM) | TCCCTTCCGTAGTCAGAG (SEQ ID NO: 75) |

*CY5 = Cyanine-5

TABLE 10

Reaction components for gene copy number analyses and plasmid backbone detection.

| Component | Amt. (µL) | Stock | Final Conc'n |
|---|---|---|---|
| 2x Buffer | 5.0 | 2x | 1x |
| Appropriate Forward Primer | 0.4 | 10 µM | 0.4 |
| Appropriate Reverse Primer | 0.4 | 10 µM | 0.4 |
| Appropriate Probe | 0.4 | 5 µM | 0.2 |
| IVR1-Forward Primer | 0.4 | 10 µM | 0.4 |
| IVR1-Reverse Primer | 0.4 | 10 µM | 0.4 |
| IVR1-Probe | 0.4 | 5 µM | 0.2 |
| H₂O | 0.6 | NA* | NA |
| gDNA | 2.0 | ND** | ND |
| Total | 10.0 | | |

*NA = Not Applicable
**ND = Not Determined

TABLE 11

Thermocycler conditions for DNA qPCR. Genomic copy number analyses

| Process | Temp. | Time | No. Cycles |
|---|---|---|---|
| Target Activation | 95° C. | 10 min | 1 |
| Denature | 95° C. | 10 sec | 40 |

TABLE 11-continued

Thermocycler conditions for DNA qPCR.
Genomic copy number analyses

| Process | Temp. | Time | No. Cycles |
|---|---|---|---|
| Extend & Acquire FAM, HEX, or CY5 | 60° C. | 40 sec |  |
| Cool | 40° C. | 10 sec | 1 |

Example 8

Transgenic *Zea mays* Comprising Coleopteran Pest Sequences 10-20 transgenic $T_0$ *Zea mays* plants are generated as described in EXAMPLE 6. A further 10-20 $T_1$ *Zea mays* independent lines expressing hairpin dsRNA for an RNAi construct are obtained for corn rootworm challenge. Hairpin dsRNA comprise a portion of SEQ ID NOs:1 and/or 3. Additional hairpin dsRNAs are derived, for example, from coleopteran pest sequences such as, for example, Cafl-180 (U.S. Patent Application Publication No. 2012/0174258), VatpaseC (U.S. Patent Application Publication No. 2012/0174259), Rhol (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), ROP, as described in U.S. patent application Ser. No. 14/577,811, RNA polymerase 11140, as described in U.S. patent application Ser. No. 14/577,854, RNA polymerase 11, as described in U.S. Patent Application No. 62/133,214, RNA polymerase 11-215, as described in U.S. Patent Application No. 62/133,202, RNA polymerase 33, as described in U.S. Patent Application No. 62/133,210, ncm, as described in U.S. Patent Application No. 62/095487, Dre4, as described in U.S. patent application Ser. No. 14/705,807, transcription elongation factor spt5, as described in U.S. Patent Application No. 62/168613, and spt6, as described in U.S. Patent Application No. 62/168606. These are confirmed through RT-PCR or other molecular analysis methods.

Total RNA preparations from selected independent $T_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, and viability of feeding coleopteran pests.

In planta delivery of dsRNA, siRNA, or miRNA corresponding to target genes and the subsequent uptake by coleopteran pests through feeding results in down-regulation of the target genes in the coleopteran pest through RNA-mediated gene silencing. When the function of a target gene is important at one or more stages of development, the growth and/or development of the coleopteran pest is affected, and in the case of at least one of WCR, NCR, SCR, MCR, *D. balteata* LeConte, *D. speciosa* Germar, *D. u. tenella*, and *D. u. undecimpunctata* Mannerheim, leads to failure to successfully infest, feed, and/or develop, or leads to death of the coleopteran pest. The choice of target genes and the successful application of RNAi are then used to control coleopteran pests.

Phenotypic comparison of transgenic RNAi lines and nontransformed *Zea mays*. Target coleopteran pest genes or sequences selected for creating hairpin dsRNA have no similarity to any known plant gene sequence. Hence, it is not expected that the production or the activation of (systemic) RNAi by constructs targeting these coleopteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 9

Transgenic *Zea mays* Comprising a Coleopteran Pest Sequence and Additional RNAi Constructs A transgenic *Zea mays* plant comprising a heterologous coding sequence in its genome that is transcribed into an iRNA molecule that targets an organism other than a coleopteran pest is secondarily transformed via *Agrobacterium* or WHISKERS™ methodologies (see Petolino and Arnold (2009) Methods Mol. Biol. 526:59-67) to produce one or more insecticidal dsRNA molecules (for example, at least one dsRNA molecule including a dsRNA molecule targeting a gene comprising SEQ ID NO:1 or SEQ ID NO:3). Plant transformation plasmid vectors prepared essentially as described in EXAMPLE 4 are delivered via *Agrobacterium* or WHISKERS™-mediated transformation methods into maize suspension cells or immature maize embryos obtained from a transgenic Hi II or B104 *Zea mays* plant comprising a heterologous coding sequence in its genome that is transcribed into an iRNA molecule that targets an organism other than a coleopteran pest.

Example 10

Transgenic *Zea mays* Comprising an RNAi Construct and Additional Coleopteran Pest Control Sequences A transgenic *Zea mays* plant comprising a heterologous coding sequence in its genome that is transcribed into an iRNA molecule that targets a coleopteran pest organism (for example, at least one dsRNA molecule including a dsRNA molecule targeting a gene comprising SEQ ID NO:1 or SEQ ID NO:3) is secondarily transformed via *Agrobacterium* or WHISKERS™ methodologies (see Petolino and Arnold (2009) Methods Mol. Biol. 526:59-67) to produce one or more insecticidal protein molecules, for example, Cry3, Cry34 and Cry35 insecticidal proteins. Plant transformation plasmid vectors prepared essentially as described in EXAMPLE 4 are delivered via *Agrobacterium* or WHISKERS™-mediated transformation methods into maize suspension cells or immature maize embryos obtained from a transgenic B104 *Zea mays* plant comprising a heterologous coding sequence in its genome that is transcribed into an iRNA molecule that targets a coleopteran pest organism. Doubly-transformed plants are obtained that produce iRNA molecules and insecticidal proteins for control of coleopteran pests.

Example 11

Screening of Candidate Target Genes in Neotropical Brown Stink Bug (*Euschistus heros*)

Neotropical Brown Stink Bug (BSB; *Euschistus heros*) colony. BSB were reared in a 27° C. incubator, at 65% relative humidity, with 16: 8 hour light: dark cycle. One gram of eggs collected over 2-3 days were seeded in 5L containers with filter paper discs at the bottom, and the containers were covered with #18 mesh for ventilation. Each rearing container yielded approximately 300-400 adult BSB. At all stages, the insects were fed fresh green beans three times per week, a sachet of seed mixture that contained sunflower seeds, soybeans, and peanuts (3:1:1 by weight ratio) was replaced once a week. Water was supplemented in vials with cotton plugs as wicks. After the initial two weeks, insects were transferred into a new container once a week.

BSB artificial diet. A BSB artificial diet was prepared as follows. Lyophilized green beans were blended to a fine powder in a MAGIC BULLET® blender, while raw (organic) peanuts were blended in a separate MAGIC BULLET® blender. Blended dry ingredients were combined (weight percentages: green beans, 35%; peanuts, 35%; sucrose, 5%; Vitamin complex (e.g., Vanderzant Vitamin Mixture for insects, SIGMA-ALDRICH, Catalog No. V1007), 0.9%); in a large MAGIC BULLET® blender, which was capped and shaken well to mix the ingredients. The mixed dry ingredients were then added to a mixing bowl. In a separate container, water and benomyl anti-fungal agent (50 ppm; 25 µL of a 20,000 ppm solution/50 mL diet solution) were mixed well, and then added to the dry ingredient mixture. All ingredients were mixed by hand until the solution was fully blended. The diet was shaped into desired sizes, wrapped loosely in aluminum foil, heated for 4 hours at 60° C., and then cooled and stored at 4° C. The artificial diet was used within two weeks of preparation.

BSB transcriptome assembly. Six stages of BSB development were selected for mRNA library preparation. Total RNA was extracted from insects frozen at −70° C., and homogenized in 10 volumes of Lysis/Binding buffer in Lysing MATRIX A 2 mL tubes (MP BIOMEDICALS, Santa Ana, Calif.) on a FastPrep®-24 Instrument (MP BIOMEDICALS). Total mRNA was extracted using a mirVana™ miRNA Isolation Kit (AMBION; INVITROGEN) according to the manufacturer's protocol. RNA sequencing using an illumina® HiSeq™ system (San Diego, Calif.) provided candidate target gene sequences for use in RNAi insect control technology. Hi Seq™ generated a total of about 378 million reads for the six samples. The reads were assembled individually for each sample using TRINITY™ assembler software (Grabherr et al. (2011) Nature Biotech. 29:644-652). The assembled transcripts were combined to generate a pooled transcriptome. This BSB pooled transcriptome contained 378,457 sequences.

BSB fsh ortholog identification. A tBLASTn search of the BSB pooled transcriptome was performed using as query, *Drosophila* fsh protein isoforms (GENBANK Accession Nos. NP_511078, NP_727228, NP_996368, NP_996369, NP_996370, NP_001162699, NP_001259321, NP_001259322, and NP_001259323). BSB fsh-1 (SEQ ID NO:76) and BSBfsh-2 (SEQ ID NO:78), were identified as *Euschistus heros* candidate targetfsh genes, the product of which have the predicted amino acid sequences of SEQ ID NO:77 and SEQ ID NO:79.

Template preparation and dsRNA synthesis. cDNA was prepared from total BSB RNA extracted from a single young adult insect (about 90 mg) using TRIzol® Reagent (LIFE TECHNOLOGIES). The insect was homogenized at room temperature in a 1.5 mL microcentrifuge tube with 200 µL TRIzol® using a pellet pestle (FISHERBRAND Catalog No. 12-141-363) and Pestle Motor Mixer (COLE-PARMER, Vernon Hills, Ill.). Following homogenization, an additional 800 µL TRIzol® was added, the homogenate was vortexed, and then incubated at room temperature for five minutes. Cell debris was removed by centrifugation, and the supernatant was transferred to a new tube. Following manufacturer-recommended TRIzol® extraction protocol for 1 mL TRIzol®, the RNA pellet was dried at room temperature and resuspended in 200 µL Tris Buffer from a GFX PCR DNA and GEL EXTRACTION KIT (illustra™; GE HEALTHCARE LIFE SCIENCES) using Elution Buffer Type 4 (i.e., 10 mM Tris-HCl; pH8.0). The RNA concentration was determined using a NANODROP™ 8000 spectrophotometer (THERMO SCIENTIFIC, Wilmington, Del.).

cDNA amplification. cDNA was reverse-transcribed from 5 µg BSB total RNA template and oligo dT primer, using a SUPERSCRIPT III FIRST-STRAND SYNTHESIS SYSTEM™ for RT-PCR (INVITROGEN), following the supplier's recommended protocol. The final volume of the transcription reaction was brought to 100 µL with nuclease-free water.

Primers as shown in Table 13 were used to amplify BSB_fsh-1 reg1. The DNA template was amplified by touch-down PCR (annealing temperature lowered from 60° C. to 50° C., in a 1° C./cycle decrease) with 1 µL cDNA (above) as the template. Fragments comprising a 367 bp segment of BSB_fsh-1 reg 1 (SEQ ID NO:80) and a 430 bp segment of BSB_fsh-2 reg1 (SEQ ID NO:81), were generated during 35 cycles of PCR. The above procedure was also used to amplify a 301 bp negative control template YFPv2 (SEQ ID NO:86), using YFPv2-F (SEQ ID NO:87) and YFPv2-R (SEQ ID NO:88) primers. The BSB_fsh-1 reg1, BSB_fsh-2 reg 1, and YFPv2 primers contained a T7 phage promoter sequence (SEQ ID NO:9) at their 5' ends, and thus enabled the use of YFPv2 and BSB_fsh DNA fragments for dsRNA transcription.

TABLE 13

Primers and Primer Pairs used to amplify portions of coding regions of exemplary fsh target genes and a YFP negative control gene.

| Gene ID | Primer ID | Sequence |
|---|---|---|
| Pair 20 fsh-1 reg1 | BSB_fsh-1_For | TTAATACGACTCACTATAGGGAGAGCCCCTGGAAGGGCACC AGGAAAAACCAATTC (SEQ ID NO: 82) |
| | BSB_fsh-1_Rev | TTAATACGACTCACTATAGGGAGACTGATACATTTTTCTTA TGTGGCTTTTTCCTGAG (SEQ ID NO: 83) |
| Pair 21 fsh-2 reg1 | BSB_fsh-2_For | TTAATACGACTCACTATAGGGAGAACAGTCAGACGATGGTA TGCCATTTTCTC (SEQ ID NO: 84) |
| | BSB_fsh-2_Rev | TTAATACGACTCACTATAGGGAGAGTCTTCAGGTACTTGAG CGAATCTCACTTC (SEQ ID NO: 85) |
| Pair 22 YFP | YFPv2-F | TTAATACGACTCACTATAGGGAGAGCATCTGGAGCACTTCT CTTTCA (SEQ ID NO: 87) |
| | YFPv2-R | TTAATACGACTCACTATAGGGAGACCATCTCCTTCAAAGGT GATTG (SEQ ID NO: 88) | dsRNA synthesis. dsRNA was synthesized using 2 μL PCR product (above) as the template with a MEGAscript™ T7 RNAi kit (AMBION) used according to the manufacturer's instructions. See FIG. 1. dsRNA was quantified on a NANODROP™ 8000 spectrophotometer, and diluted to 500 ng/μL in nuclease-free 0.1× TE buffer (1 mM Tris HCL, 0.1 mM EDTA, pH 7.4).

Injection of dsRNA into BSB hemocoel. BSB were reared on a green bean and seed diet, as the colony, in a 27° C. incubator at 65% relative humidity and 16:8 hour light: dark photoperiod. Second instar nymphs (each weighing 1 to 1.5 mg) were gently handled with a small brush to prevent injury, and were placed in a Petri dish on ice to chill and immobilize the insects. Each insect was injected with 55.2 nL 500 ng/μL dsRNA solution (i.e., 27.6 ng dsRNA; dosage of 18.4 to 27.6 μg/g body weight). Injections were performed using a NANOJECT™ II injector (DRUMMOND SCIENTIFIC, Broomhall, Pa.), equipped with an injection needle pulled from a Drummond 3.5 inch #3-000-203-G/X glass capillary. The needle tip was broken, and the capillary was backfilled with light mineral oil and then filled with 2 to 3 μL dsRNA. dsRNA was injected into the abdomen of the nymphs (10 insects injected per dsRNA per trial), and the trials were repeated on three different days. Injected insects (5 per well) were transferred into 32-well trays (Bio-RT-32 Rearing Tray; BIO-SERV, Frenchtown, N.J.) containing a pellet of artificial BSB diet, and covered with Pull-N- Peel™ tabs (BIO-CV-4; BIO-SERV). Moisture was supplied by means of 1.25 mL water in a 1.5 mL microcentrifuge tube with a cotton wick. The trays were incubated at 26.5° C., 60% humidity, and 16:8 hour light: dark photoperiod. Viability counts and weights were taken on day 7 after the injections.

BSB fsh is a lethal dsRNA target. As summarized in Table 14, in each replicate, at least ten $2^{nd}$ instar BSB nymphs (1-1.5 mg each) were injected into the hemocoel with 55.2 nL BSB_fsh-1 reg 1 or BSB_fsh-2 regi dsRNA (500 ng/μL), for an approximate final concentration of 18.4-27.6 μg dsRNA/g insect. The mortality determined for BSB_fsh-1 reg1 and dsRNA was higher than that observed with the same amount of injected YFPv2 dsRNA (negative control).

TABLE 14

Results of BSB fsh dsRNA injection into the hemocoel of $2^{nd}$ instar Neotropical Brown Stink Bug nymphs seven days after injection.

| Treatment* | N Trials | Mean % Mortality ± SEM** | p value t-test |
|---|---|---|---|
| BSB fsh-1 reg1 | 3 | 37 ± 6.7 | 0.0158[†] |
| BSB fsh-2 reg1 | 3 | 40 ± 20 | 0.176 |
| Not injected | 3 | 17 ± 8.8 | 0.349 |
| YFPv2 | 3 | 6.7 ± 3.3 | |

*Ten insects injected per trial for each dsRNA.
**Standard error of the mean
[†]indicates significant difference from the YFPv2 dsRNA control using a Student's t-test p ≤ 0.05.

Example 12

Transgenic *Zea mays* Comprising Hemipteran Pest Sequences

Ten to 20 transgenic $T_0$ *Zea mays* plants harboring expression vectors for nucleic acids comprising any portion of SEQ ID NO:76 or SEQ ID NO:78 (e.g., SEQ ID NO:80 and SEQ ID NO:81) are generated as described in EXAMPLE 4. A further 10-20 $T_1$ *Zea mays* independent lines expressing hairpin dsRNA for an RNAi construct are obtained for BSB challenge. Hairpin dsRNA are derived comprising a portion of SEQ ID NO:76 or SEQ ID NO:78 or segments thereof (e.g., SEQ ID NO:80 and SEQ ID NO:81). These are confirmed through RT-PCR or other molecular analysis methods. Total RNA preparations from selected independent $T_1$ lines are optionally used for RT-PCR with primers designed to bind in the linker intron of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect hemipterans in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, and viability of feeding hemipteran pests.

In planta delivery of dsRNA, siRNA, shRNA, hpRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and/or survival of the hemipteran pest is affected, and in the case of at least one of *Euschistus heros, E. serous, Nezara viridula, Piezodorus guildinii, Halyomorpha halys, Chinavia hilare, C. marginatum, Dichelops melacanthus, D. furcatus; Edessa meditabunda, Thyanta perditor, Horcias nobilellus, Taedia stigmosa, Dysdercus peruvianus, Neomegalotomus parvus, Leptoglossus zonatus, Niesthrea sidae, Lygus hesperus,* and *L. lineolaris* leads to failure to successfully infest, feed, develop, and/or leads to death of the hemipteran pest. The choice of target genes and the successful application of RNAi is then used to control hemipteran pests.

Phenotypic comparison of transgenic RNAi lines and non-transformed *Zea mays*. Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 13

Transgenic *Glycine max* Comprising Hemipteran Pest Sequences

Ten to 20 transgenic $T_0$ *Glycine max* plants harboring expression vectors for nucleic acids comprising a portion of SEQ ID NO:76, SEQ ID NO:78, and/or segments thereof (e.g., SEQ ID NO:80 and SEQ ID NO:81) are generated as is known in the art, including for example by *Agrobacterium*-mediated transformation, as follows. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_0O$ for sixteen hours in the dark using a black box at 24° C.

Preparation of split-seed soybeans. The split soybean seed comprising a portion of an embryonic axis protocol requires preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of *Agrobacterium tumefaciens* (e.g., strain EHA 101 or EHA 105) containing a binary plasmid comprising SEQ ID NO:76, SEQ ID NO:78, and/or segments thereof (e.g., SEQ ID NO:80 and SEQ ID NO:81). The *A. tumefaciens* solution is diluted to a final concentration of $\lambda$=0.6 $OD_{650}$ before immersing the cotyledons comprising the embryo axis.

Co-cultivation. Following inoculation, the split soybean seed is allowed to co-cultivate with the *Agrobacterium tumefaciens* strain for 5 days on co-cultivation medium (*Agrobacterium* Protocols, vol. 2, $2^{nd}$ Ed., Wang, K. (Ed.) Humana Press, New Jersey, 2006) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, and 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate)(LIBERTY®.

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2EDTA$, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, and 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 μmol/m²sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2EDTA$, 20 g/L sucrose and 0.59 g/L IVIES, 50 mg/L asparagine, 100 mg/L L-pyroglutamic acid 7 g/L Noble agar, pH 5.6) in phyta trays.

Cultivation. Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/m²sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

A further 10-20 $T_1$ *Glycine max* independent lines expressing hairpin dsRNA for an RNAi construct are obtained for BSB challenge. Hairpin dsRNA may be derived comprising any of SEQ ID NO:76, SEQ ID NO:78, and segments thereof (e.g., SEQ ID NO:80 and SEQ ID NO:81). These are confirmed through RT-PCR or other molecular analysis methods as known in the art. Total RNA preparations from selected independent $T_1$ lines are optionally used for RT-PCR with primers designed to bind in the linker intron of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Glycine max* plant. Processing of the dsRNA hairpin of the target genes into siRNA is subsequently optionally confirmed in independent transgenic lines using RNA blot hybridizations.

RNAi molecules having mismatch sequences with more than 80% sequence identity to target genes affect BSB in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, and viability of feeding hemipteran pests.

In planta delivery of dsRNA, siRNA, shRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and viability of feeding of the hemipteran pest is affected, and in the case of at least one of *Euchistus heros, Piezodorus guildinii, Halyomorpha halys, Nezara viridula, Chinavia hilare, Euschistus serous, Dichelops melacanthus, Dichelops furcatus, Edessa meditabunda, Thyanta perditor, Chinavia marginatum, Horcias nobilellus, Taedia stigmosa, Dysdercus peruvianus, Neomegalotomus parvus, Leptoglossus zonatus, Niesthrea sidae*, and *Lygus lineolaris* leads to failure to successfully infest, feed, develop, and/or leads to death of the hemipteran pest. The choice of target genes and the successful application of RNAi is then used to control hemipteran pests.

Phenotypic comparison of transgenic RNAi lines and non-transformed *Glycine max*. Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage, and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 14

*E. heros* Bioassays on Artificial Diet.

In dsRNA feeding assays on artificial diet, 32-well trays are set up with an ~18 mg pellet of artificial diet and water, as for injection experiments (See EXAMPLE 12). dsRNA at a concentration of 200 ng/μL is added to the food pellet and water sample; 100 μL to each of two wells. Five $2^{nd}$ instar *E. heros* nymphs are introduced into each well. Water samples and dsRNA that targets a YFP transcript are used as negative controls. The experiments are repeated on three different days. Surviving insects are weighed, and the mortality rates are determined after 8 days of treatment. Mortality and/or growth inhibition is observed in the wells provided with BSB fsh dsRNA, compared to the control wells.

Example 15

Transgenic *Arabidopsis thaliana* Comprising Hemipteran Pest Sequences

*Arabidopsis* transformation vectors containing a target gene construct for hairpin formation comprising segments of fsh (e.g., SEQ ID NOs:76 and 78) are generated using standard molecular methods similar to EXAMPLE 4. *Arabidopsis* transformation is performed using standard *Agrobacterium*-based procedure. Ti seeds are selected with glufosinate tolerance selectable marker. Transgenic $T_1$ *Arabidopsis* plants are generated and homozygous simple-copy $T_2$ transgenic plants are generated for insect studies. Bioassays are performed on growing *Arabidopsis* plants with inflorescences. Five to ten insects are placed on each plant and monitored for survival within 14 days.

Construction of *Arabidopsis* transformation vectors. Entry clones based on an entry vector harboring a target gene construct for hairpin formation comprising a segment of SEQ ID NOs:76 or SEQ ID NO:78 are assembled using a combination of chemically synthesized fragments (DNA2.0, Menlo Park, CA) and standard molecular cloning methods. Intramolecular hairpin formation by RNA primary transcripts is facilitated by arranging (within a single transcription unit) two copies of a target gene segment in opposite orientations, the two segments being separated by an linker sequence (for example and without limitation, an intervening "loop" polynucleotide (e.g., SEQ ID NO:100) or an ST-LS1 intron; Vancanneyt et al. (1990) Mol. Gen. Genet. 220(2):245-50). Thus, the primary mRNA transcript contains the two fsh gene segment sequences as large inverted repeats of one another, separated by the linker sequence. A copy of a promoter (e.g. *Arabidopsis thaliana* ubiquitin 10 promoter (Callis et al. (1990) J. Biological Chem. 265: 12486-12493)) is used to drive production of the primary mRNA hairpin transcript, and a fragment comprising a 3' untranslated region from Open Reading Frame 23 of *Agrobacterium tumefaciens* (AtuORF23 3' UTR v1; U.S. Pat. No. 5,428,147) is used to terminate transcription of the hairpin-RNA-expressing gene.

The hairpin clones within entry vectors are used in standard GATEWAY® recombination reactions with a typical binary destination vector to produce hairpin RNA expression transformation vectors for *Agrobacterium*-mediated *Arabidopsis* transformation.

A binary destination vector comprises a herbicide tolerance gene, DSM-2v2 (U.S. Patent Publication No. 2011/0107455), under the regulation of a Cassava vein mosaic virus promoter (CsVMV Promoter v2, U.S. Pat. No. 7,601,885; Verdaguer et al. (1996) Plant Mol. Biol. 31:1129-39). A fragment comprising a 3' untranslated region from Open Reading Frame 1 of *Agrobacterium tumefaciens* (AtuORF1 3' UTR v6; Huang et al. (1990) J. Bacteriol. 172:1814-22) is used to terminate transcription of the D SM2v2 mRNA.

A negative control binary construct which comprises a gene that expresses a YFP hairpin RNA, is constructed by means of standard GATEWAY® recombination reactions with a typical binary destination vector and entry vector. The entry construct comprises a YFP hairpin sequence under the expression control of an *Arabidopsis* Ubiquitin 10 promoter (as above) and a fragment comprising an ORF23 3' untranslated region from *Agrobacterium tumefaciens* (as above).

Production of transgenic Arabidopsis comprising insecticidal RNAs: *Agrobacterium*-mediated transformation. Binary plasmids containing hairpin dsRNA sequences are electroporated into *Agrobacterium* strain GV3101 (pMP9ORK). The recombinant *Agrobacterium* clones are confirmed by restriction analysis of plasmids preparations of the recombinant *Agrobacterium* colonies. A Qiagen Plasmid Max Kit (Qiagen, Cat # 12162) is used to extract plasmids from *Agrobacterium* cultures following the manufacture recommended protocol.

*Arabidopsis* transformation and $T_1$ Selection. Twelve to fifteen *Arabidopsis* plants (c.v. Columbia) are grown in 4" pots in the green house with light intensity of 250 µmol/m$^2$, 25° C., and 18:6 hours of light: dark conditions. Primary flower stems are trimmed one week before transformation. Agrobacterium inoculums are prepared by incubating 10 µL recombinant *Agrobacterium* glycerol stock in 100 mL LB broth (Sigma L3022) +100 mg/L Spectinomycin +50 mg/L Kanamycin at 28° C. and shaking at 225 rpm for 72 hours. *Agrobacterium* cells are harvested and suspended into 5% sucrose +0.04% Silwet-L77 (Lehle Seeds Cat # VIS-02)+10 µg/L benzamino purine (BA) solution to OD$_{600}$ 0.8~1.0 before floral dipping. The above-ground parts of the plant are dipped into the *Agrobacterium* solution for 5-10 minutes, with gentle agitation. The plants are then transferred to the greenhouse for normal growth with regular watering and fertilizing until seed set.

Example 16

Growth and Bioassays of Transgenic *Arabidopsis*

Selection of $T_1$ *Arabidopsis* transformed with dsRNA constructs. Up to 200 mg of $T_1$ seeds from each transformation are stratified in 0.1% agarose solution. The seeds are planted in germination trays (10.5"×21"×1"; T.O. Plastics Inc., Clearwater, Minn.) with #5 sunshine media. Transformants are selected for tolerance to Ignite® (glufosinate) at 280 g/ha at 6 and 9 days post planting. Selected events are transplanted into 4" diameter pots. Insertion copy analysis is performed within a week of transplanting via hydrolysis quantitative Real-Time PCR (qPCR) using Roche LightCycler480™. The PCR primers and hydrolysis probes are designed against DSM2v2 selectable marker using LightCycler™ Probe Design Software 2.0 (Roche). Plants are maintained at 24° C., with a 16:8 hour light: dark photoperiod under fluorescent and incandescent lights at intensity of 100-150 mE/m$^2$s.

*E. heros* plant feeding bioassay. At least four low copy (1-2 insertions), four medium copy (2-3 insertions), and four high copy (>4 insertions) events are selected for each construct. Plants are grown to a reproductive stage (plants containing flowers and siliques). The surface of soil is covered with ~50 mL volume of white sand for easy insect identification. Five to ten 2nd instar *E. heros* nymphs are introduced onto each plant. The plants are covered with plastic tubes that are 3" in diameter, 16" tall, and with wall thickness of 0.03" (Item No. 484485, Visipack Fenton Mo.); the tubes are covered with nylon mesh to isolate the insects. The plants are kept under normal temperature, light, and watering conditions in a conviron. In 14 days, the insects are collected and weighed; percent mortality as well as growth inhibition (1-weight treatment/weight control) are calculated. YFP hairpin-expressing plants are used as controls.

$T_2$ *Arabidopsis* seed generation and $T_2$ bioassays. $T_2$ seed is produced from selected low copy (1-2 insertions) events for each construct. Plants (homozygous and/or heterozygous) are subjected to *E. heros* feeding bioassay, as described above. $T_3$ seed is harvested from homozygotes and stored for future analysis.

Example 17

Transformation of Additional Crop Species

Cotton is Transformed with an fsh dsRNA Transgene to Provide Control of Hemipteran insects by utilizing a method known to those of skill in the art, for example, substantially the same techniques previously described in EXAMPLE 14 of U.S. Pat. No. 7,838,733, or Example 12 of PCT International Patent Publication No. WO 2007/053482.

Example 18 fsh dsRNA in Insect Management

Fsh dsRNA transgenes are combined with other dsRNA molecules in transgenic plants to provide redundant insect control and RNAi effects. Transgenic plants including, for example and without limitation, corn, soybean, and cotton expressing dsRNA that targets fsh are useful for preventing feeding damage by coleopteran and hemipteran insects. Fsh dsRNA transgenes are also combined in plants with *Bacillus thuringiensis*, PIP-1, and/or AflP insecticidal protein technology to represent new modes of action in Insect Resistance Management gene pyramids. When combined with other dsRNA molecules that target insect pests and/or with insecticidal proteins in transgenic plants, an increased insecticidal effect is observed that also mitigates the development of resistant insect populations.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

Particular, non-limiting examples of representative embodiments are set forth below:

Embodiment 1: An isolated nucleic acid molecule comprising at least one polynucleotide operably linked to a heterologous promoter, wherein the polynucleotide comprises a nucleotide sequence selected from the group consisting of: SEQ ID NO:1; the complement of SEQ ID NO:1; the reverse complement of SEQ ID NO:1; a fragment of at least 15 contiguous nucleotides of SEQ ID NO:1; the complement of a fragment of at least 15 contiguous nucleotides of SEQ ID NO:1; the reverse complement of a fragment of at least 15 contiguous nucleotides of SEQ ID NO:1; a native coding sequence of a *Diabrotica* organism comprising SEQ ID NO:5 and/or SEQ ID NO:7; the complement of a native coding sequence of a *Diabrotica* organism comprising SEQ ID NO:5 and/or SEQ ID NO:7; the reverse complement of a native coding sequence of a *Diabrotica* organism comprising SEQ ID NO:5 and/or SEQ ID NO:7; a fragment of at least 15 contiguous nucleotides of a native coding sequence of a *Diabrotica* organism comprising SEQ ID NO:5 and/or SEQ ID NO:7; the complement of a fragment of at least 15 contiguous nucleotides of a native coding sequence of a *Diabrotica* organism comprising SEQ ID NO:5 and/or SEQ ID NO:7; the reverse complement of a fragment of at least 15 contiguous nucleotides of a native coding sequence of a *Diabrotica* organism comprising SEQ ID NO:5 and/or SEQ ID NO:7; SEQ ID NO:3; the complement of SEQ ID NO:3; the reverse complement of SEQ ID NO:3; a fragment of at least 15 contiguous nucleotides of SEQ ID NO:3; the complement of a fragment of at least 15 contiguous nucleotides of SEQ ID NO:3; the reverse complement of a fragment of at least 15 contiguous nucleotides of SEQ ID NO:3; a native coding sequence of a *Diabrotica* organism comprising SEQ ID NO:6 and/or SEQ ID NO:8; the complement of a native coding sequence of a *Diabrotica* organism comprising SEQ ID NO:6 and/or SEQ ID NO:8; the reverse complement of a native coding sequence of a *Diabrotica* organism comprising SEQ ID NO:6 and/or SEQ ID NO:8; a fragment of at least 15 contiguous nucleotides of a native coding sequence of a *Diabrotica* organism comprising SEQ ID NO:6 and/or SEQ ID NO:8; the complement of a fragment of at least 15 contiguous nucleotides of a native coding sequence of a *Diabrotica* organism comprising SEQ ID NO:6 and/or SEQ ID NO:8; the reverse complement of a fragment of at least 15 contiguous nucleotides of a native coding sequence of a *Diabrotica* organism comprising SEQ ID NO:6 and/or SEQ ID NO:8; SEQ ID NO:76; the complement of SEQ ID NO:76; the reverse complement of SEQ ID NO:76; a fragment of at least 15 contiguous nucleotides of SEQ ID NO:76; the complement of a fragment of at least 15 contiguous nucleotides of SEQ ID NO:76; the reverse complement of a fragment of at least 15 contiguous nucleotides of SEQ ID NO:76; a native coding sequence of a *Euschistus* organism comprising SEQ ID NO:80; the complement of a native coding sequence of a *Euschistus* organism comprising SEQ ID NO:80; the reverse complement of a native coding sequence of a *Euschistus* organism comprising SEQ ID NO:80; a fragment of at least 15 contiguous nucleotides of a native coding sequence of a *Euschistus* organism comprising SEQ ID NO:80; the complement of a fragment of at least 15 contiguous nucleotides of a native coding sequence of a *Euschistus* organism comprising SEQ ID NO:80; the reverse complement of a fragment of at least 15 contiguous nucleotides of a native coding sequence of a *Euschistus* organism comprising SEQ ID NO:80; SEQ ID NO:78; the complement of SEQ ID NO:78; the reverse complement of SEQ ID NO:78; a fragment of at least 15 contiguous nucleotides of SEQ ID NO:78; the complement of a fragment of at least 15 contiguous nucleotides of SEQ ID NO:78; the reverse complement of a fragment of at least 15 contiguous nucleotides of SEQ ID NO:78; a native coding sequence of a *Euschistus* organism comprising SEQ ID NO:81; the complement of a native coding sequence of a *Euschistus* organism comprising SEQ ID NO:81; the reverse complement of a native coding sequence of a *Euschistus* organism comprising SEQ ID NO:81; a fragment of at least 15 contiguous nucleotides of a native coding sequence of a *Euschistus* organism comprising SEQ ID NO:81; the complement of a fragment of at least 15 contiguous nucleotides of a native coding sequence of a *Euschistus* organism comprising SEQ ID NO:81; and the reverse complement of a fragment of at least 15 contiguous nucleotides of a native coding sequence of a *Euschistus* organism comprising SEQ ID NO:81.

Embodiment 2: The nucleic acid molecule of Embodiment 1, wherein the polynucleotide is selected from the group consisting of: SEQ ID NO:1; the complement of SEQ ID NO:1; the reverse complement of SEQ ID NO:1; a fragment of at least 15 contiguous nucleotides of SEQ ID NO:1; the complement of a fragment of at least 15 contiguous nucleotides of SEQ ID NO:1; the reverse complement of a fragment of at least 15 contiguous nucleotides of SEQ ID NO:1; a native coding sequence of a *Diabrotica* organism comprising SEQ ID NO:5 and/or SEQ ID NO:7; the complement of a native coding sequence of a *Diabrotica* organism comprising SEQ ID NO:5 and/or SEQ ID NO:7; the reverse complement of a native coding sequence of a *Diabrotica* organism comprising SEQ ID NO:5 and/or SEQ ID NO:7; a fragment of at least 15 contiguous nucleotides of a native coding sequence of a *Diabrotica* organism comprising SEQ ID NO:5 and/or SEQ ID NO:7; the complement of a fragment of at least 15 contiguous nucleotides of a native coding sequence of a *Diabrotica* organism comprising SEQ ID NO:5 and/or SEQ ID NO:7; the reverse complement of a fragment of at least 15 contiguous nucleotides of a native coding sequence of a *Diabrotica* organism comprising SEQ ID NO:5 and/or SEQ ID NO:7; SEQ ID NO:3; the complement of SEQ ID NO:3; the reverse complement of SEQ ID NO:3; a fragment of at least 15 contiguous nucleotides of SEQ ID NO:3; the complement of a fragment of at least 15 contiguous nucleotides of SEQ ID NO:3; the reverse complement of a fragment of at least 15 contiguous nucleotides of SEQ ID NO:3; a native coding sequence of a *Diabrotica* organism comprising SEQ ID NO:6 and/or SEQ ID NO:8; the complement of a native coding sequence of a *Diabrotica* organism comprising SEQ ID NO:6 and/or SEQ ID NO:8; the reverse complement of a native coding sequence of a *Diabrotica* organism comprising SEQ ID NO:6 and/or SEQ ID NO:8; a fragment of at least 15 contiguous nucleotides of a native coding sequence of a *Diabrotica* organism comprising SEQ ID NO:6 and/or SEQ ID NO:8; the complement of a fragment of at least 15 contiguous nucleotides of a native coding sequence of a *Diabrotica* organism comprising SEQ ID NO:6 and/or SEQ ID NO:8; and the reverse complement of a fragment of at least 15 contiguous nucleotides of a native coding sequence of a *Diabrotica* organism comprising SEQ ID NO:6 and/or SEQ ID NO:8.

Embodiment 3: The nucleic acid molecule of Embodiment 1, wherein the polynucleotide is selected from the group consisting of: SEQ ID NO:76; the complement of SEQ ID NO:76; the reverse complement of SEQ ID NO:76; a fragment of at least 15 contiguous nucleotides of SEQ ID NO:76; the complement of a fragment of at least 15 contiguous nucleotides of SEQ ID NO:76; the reverse complement of a fragment of at least 15 contiguous nucleotides of SEQ ID NO:76; a native coding sequence of a *Euschistus* organism comprising SEQ ID NO:80; the complement of a native coding sequence of a *Euschistus* organism comprising SEQ ID NO:80; the reverse complement of a native coding sequence of a *Euschistus* organism comprising SEQ ID NO:80; a fragment of at least 15 contiguous nucleotides of a native coding sequence of a *Euschistus* organism comprising SEQ ID NO:80; the complement of a fragment of at least 15 contiguous nucleotides of a native coding sequence of a *Euschistus* organism comprising SEQ ID NO:80; the reverse complement of a fragment of at least 15 contiguous nucleotides of a native coding sequence of a *Euschistus* organism comprising SEQ ID NO:80; SEQ ID NO:78; the complement of SEQ ID NO:78; the reverse complement of SEQ ID NO:78; a fragment of at least 15 contiguous nucleotides of SEQ ID NO:78; the complement of a fragment of at least 15 contiguous nucleotides of SEQ ID NO:78; the reverse complement of a fragment of at least 15 contiguous nucleotides of SEQ ID NO:78; a native coding sequence of a *Euschistus* organism comprising SEQ ID NO:81; the complement of a native coding sequence of a *Euschistus* organism comprising SEQ ID NO:81; the reverse complement of a native coding sequence of a *Euschistus* organism comprising SEQ ID NO:81; a fragment of at least 15 contiguous nucleotides of a native coding sequence of a *Euschistus* organism comprising SEQ ID NO:81; the complement of a fragment of at least 15 contiguous nucleotides of a native coding sequence of a *Euschistus* organism comprising SEQ ID NO:81; and the reverse complement of a fragment of at least 15 contiguous nucleotides of a native coding sequence of a *Euschistus* organism comprising SEQ ID NO:81.

Embodiment 4: The nucleic acid molecule of Embodiment 1, wherein the nucleotide sequence is selected from the group consisting of SEQ ID NO:1, SEQ ID NO:3, SEQ ID NO:5, SEQ ID NO:6, SEQ ID NO:7, SEQ ID NO:8, SEQ ID NO:76, SEQ ID NO:78, SEQ ID NO:80, SEQ ID NO:81, the complements of the foregoing, and the reverse complements of the foregoing.

Embodiment 5: The nucleic acid molecule of any of Embodiments 1, 2, and 4, wherein the nucleotide sequence is selected from the group consisting of SEQ ID NO:1, SEQ ID NO:3, SEQ ID NO:5, SEQ ID NO:6, SEQ ID NO:7, SEQ ID NO:8, the complements of the foregoing, and the reverse complements of the foregoing.

Embodiment 6: The nucleic acid molecule of any of Embodiments 1, 3, and 4, wherein the nucleotide sequence is selected from the group consisting of SEQ ID NO:76, SEQ ID NO:78, SEQ ID NO:80, SEQ ID NO:81, the complements of the foregoing, and the reverse complements of the foregoing.

Embodiment 7: The nucleic acid molecule of any of Embodiments 1, 2, 4, and 5, wherein the organism is any organism selected from the group consisting of *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; *D. u. undecimpunctata* Mannerheim; and *D. speciosa* Germar.

Embodiment 8: The nucleic acid molecule of any of Embodiments 1, 3, 4, and 6, wherein the organism is any organism selected from the group consisting of *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

Embodiment 9: The nucleic acid molecule of any of Embodiments 1-8, wherein the heterologous promoter is any promoter selected from the group consisting of maize ubiquitin 1 (U.S. Pat. No. 5,510,474), 35S from Cauliflower Mosaic Virus (CaMV), Sugarcane bacilliform badnavirus (ScBV) promoter, promoters from rice actin genes, ubiquitin promoters, pEMU, MAS, maize H3 histone promoter, ALS promoter, phaseolin gene promoter, cab, rubisco, LAT52, Zm13, and apg.

Embodiment 10: The nucleic acid molecule of any of Embodiments 1-9, wherein the molecule is a vector.

Embodiment 11: The vector of Embodiment 10, wherein the vector comprises as a transcription terminator a fragment comprising any 3' untranslated region of a gene selected from the group consisting of a maize peroxidase 5 gene (ZmPer5 3'UTR v2; U.S. Pat. No. 6,699,984), AtUbi10, AtEfl, and StPinII.

Embodiment 12: A RNA molecule encoded by the nucleic acid molecule of any of Embodiments 1-8, wherein the RNA molecule comprises a polyribonucleotide encoded by the polynucleotide.

Embodiment 13: The RNA molecule of Embodiment 12, wherein the molecule is a dsRNA molecule.

Embodiment 14: The dsRNA molecule of Embodiment 13, wherein contacting the molecule with a coleopteran pest inhibits the expression of an endogenous nucleic acid molecule that is specifically complementary to the polyribonucleotide.

Embodiment 15: The dsRNA molecule of Embodiment 14, wherein the coleopteran pest is any pest selected from the group consisting of *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; *D. u. undecimpunctata* Mannerheim; and *D. speciosa* Germar.

Embodiment 16: The dsRNA molecule of either of Embodiments 14 and 15, wherein contacting the molecule with the coleopteran pest kills or inhibits the growth and/or feeding of the pest.

Embodiment 17: The dsRNA molecule of Embodiment 13, wherein contacting the molecule with a hemipteran pest inhibits the expression of an endogenous nucleic acid molecule that is specifically complementary to the polyribonucleotide.

Embodiment 18: The dsRNA molecule of Embodiment 17, wherein the hemipteran pest is selected from the group consisting of *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyantaperditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas),

*Niesthrea sidae* (F.), *Lygus hesperus* (Knight) (Western Tarnished Plant Bug), and *Lygus lineolaris* (Palisot de Beauvois).

Embodiment 19: The dsRNA molecule of either of Embodiments 17 and 18, wherein contacting the molecule with the hemipteran pest kills or inhibits the growth and/or feeding of the pest.

Embodiment 20: The dsRNA molecule of any of Embodiments 13-19, comprising a first, a second, and a third polyribonucleotide, wherein the first polyribonucleotide is encoded by the nucleotide sequence, wherein the third polyribonucleotide is linked to the first polyribonucleotide by the second polyribonucleotide, and wherein the third polyribonucleotide is substantially the reverse complement of the first polyribonucleotide, such that the first and the third polyribonucleotides hybridize when transcribed into a ribonucleic acid to form the dsRNA.

Embodiment 21: The dsRNA molecule of any of Embodiments 13-19, wherein the molecule comprises a single-stranded polyribonucleotide that is encoded by the polynucleotide, wherein the polyribonucleotide has a length of any of: at least about 15 nucleotides in length, at least about 25 nucleotides in length, at least about 50 nucleotides in length, at least about 100 nucleotides in length, at least about 200 nucleotides in length, at least about 300 nucleotides in length, at least about 400 nucleotides in length, at least about 500 nucleotides in length, at least about 1000 nucleotides in length, between about 15 and about 30 nucleotides in length, between about 19 and about 25 nucleotides in length, between about 20 and about 100 nucleotides in length, between about 200 and about 300 nucleotides in length, and between about 500 and about 1000 nucleotides in length.

Embodiment 22: The vector of Embodiment 10, wherein the heterologous promoter is functional in a plant cell, and wherein the vector is a plant transformation vector.

Embodiment 23: A cell comprising the nucleic acid molecule of any of Embodiments 1-22.

Embodiment 24: The cell of Embodiment 23, wherein the cell is a prokaryotic cell.

Embodiment 25: The cell of Embodiment 23, wherein the cell is a eukaryotic cell.

Embodiment 26: The cell of Embodiment 25, wherein the cell is a plant cell.

Embodiment 27: A plant part or plant cell comprising the nucleic acid molecule of any of Embodiments 1-22.

Embodiment 28: The plant part of Embodiment 27, wherein the plant part is a seed.

Embodiment 29: A transgenic plant comprising the plant part or plant cell of Embodiment 27.

Embodiment 30: A food product or commodity product produced from the plant of Embodiment 29, wherein the product comprises a detectable amount of the polynucleotide or the polyribonucleotide encoded by the polynucleotide.

Embodiment 31: The food product or commodity product of Embodiment 30, wherein the product is selected from an oil, meal, and a fiber.

Embodiment 32: The plant of Embodiment 29, wherein the polynucleotide is expressed in the plant as a dsRNA molecule.

Embodiment 33: The cell of Embodiment 27, wherein the cell is a *Zea mays, Glycine max*, or *Gossypium* sp. cell.

Embodiment 34: The cell of Embodiment 33, wherein the cell is a *Zea mays* cell.

Embodiment 35: The cell of Embodiment 33, wherein the cell is a *Glycine max* cell.

Embodiment 36: The cell of Embodiment 33, wherein the cell is a *Gossypium* sp. cell.

Embodiment 37: The plant of either of Embodiments 29 and 32, wherein the plant is *Zea mays, Glycine max*, or a *Gossypium* sp.

Embodiment 38: The plant of Embodiment 37, wherein the plant is *Zea mays*.

Embodiment 39: The plant of Embodiment 37, wherein the plant is *Glycine max*.

Embodiment 40: The plant of Embodiment 37, wherein the plant is a *Gossypium* sp.

Embodiment 41: The plant of any of Embodiments 32 and 37-40, wherein the polynucleotide is expressed in the plant as a dsRNA molecule, and the dsRNA molecule inhibits the expression of an endogenous polynucleotide that is specifically complementary to the RNA molecule when an insect pest ingests a part of the plant.

Embodiment 42: The plant of Embodiment 41, wherein the insect pest is a coleopteran pest.

Embodiment 43: The plant of Embodiment 42, wherein the coleopteran pest is any pest selected from the group consisting of *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella; D. u. undecimpunctata* Mannerheim; and *D. speciosa* Germar.

Embodiment 44: The plant of Embodiment 41, wherein the insect pest is a hemipteran pest.

Embodiment 45: The plant of Embodiment 44, wherein the hemipteran pest is any pest selected from the group consisting of *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyantaperditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

Embodiment 46: A sprayable formulation or bait composition comprising the RNA molecule of any of Embodiments 12-21.

Embodiment 47: The nucleic acid molecule of any of Embodiments 1-11, further comprising at least one additional polynucleotide operably linked to a heterologous promoter, wherein the additional polynucleotide encodes a polyribonucleotide.

Embodiment 48: The nucleic acid molecule of Embodiment 47, wherein the heterologous promoter that is operably linked to the additional polynucleotide is functional in a plant cell, and wherein the molecule is a plant transformation vector.

Embodiment 49: A method for controlling an insect pest population, the method comprising contacting an insect pest of the population with an agent comprising a dsRNA molecule that functions upon contact with the insect pest to inhibit a biological function within the pest, wherein the molecule comprises a polyribonucleotide that is specifically hybridizable with a reference polyribonucleotide selected from the group consisting of SEQ ID NOs:89-98; the complement of any of SEQ ID NOs:89-98; the reverse complement of any of SEQ ID NOs:89-98; a fragment of at least 15 contiguous nucleotides of any of SEQ ID NOs:89-98; the complement of a fragment of at least 15 contiguous nucleotides of any of SEQ ID NOs:89-98; the reverse complement of a fragment of at least 15 contiguous nucleotides of any of SEQ ID NOs:89-98; a transcript of any of SEQ ID NO:1, SEQ ID NO:3, SEQ ID NO:76, and SEQ ID NO:78; the complement of a transcript of any of SEQ ID NO:1, SEQ ID NO:3, SEQ ID NO:76, and SEQ ID NO:78; the reverse complement of a transcript of any of SEQ ID NO:1, SEQ ID NO:3, SEQ ID NO:76, and SEQ ID NO:78; a fragment of at least 15 contiguous nucleotides of a transcript of any of SEQ ID NO:1, SEQ ID NO:3, SEQ ID NO:76, and SEQ ID NO:78; the complement of a fragment of at least 15 contiguous nucleotides of a transcript of any of SEQ ID NO:1, SEQ ID NO:3, SEQ ID NO:76, and SEQ ID NO:78; and the reverse complement of a fragment of at least 15 contiguous nucleotides of a transcript of any of SEQ ID NO:1, SEQ ID NO:3, SEQ ID NO:76, and SEQ ID NO:78.

Embodiment 50: The method according to Embodiment 49, wherein the polyribonucleotide is specifically hybridizable with a reference polyribonucleotide selected from the group consisting of SEQ ID NOs:89-94; the complement of any of SEQ ID NOs:89-94; the reverse complement of any of SEQ ID NOs:89-94; a fragment of at least 15 contiguous nucleotides of any of SEQ ID NOs:89-94; the complement of a fragment of at least 15 contiguous nucleotides of any of SEQ ID NOs:89-94; the reverse complement of a fragment of at least 15 contiguous nucleotides of any of SEQ ID NOs:89-94; a transcript of SEQ ID NO:1; the complement of a transcript of SEQ ID NO:1; the reverse complement of a transcript of SEQ ID NO:1; a fragment of at least 15 contiguous nucleotides of a transcript of SEQ ID NO:1; the complement of a fragment of at least 15 contiguous nucleotides of a transcript of SEQ ID NO:1; the reverse complement of a fragment of at least 15 contiguous nucleotides of a transcript of SEQ ID NO:1; a transcript of SEQ ID NO:3; the complement of a transcript of SEQ ID NO:3; the reverse complement of a transcript of SEQ ID NO:3; a fragment of at least 15 contiguous nucleotides of a transcript of SEQ ID NO:3; the complement of a fragment of at least 15 contiguous nucleotides of a transcript of SEQ ID NO:3; and the reverse complement of a fragment of at least 15 contiguous nucleotides of a transcript of SEQ ID NO:3.

Embodiment 51: The method according to Embodiment 49, wherein the polyribonucleotide is specifically hybridizable with a reference polyribonucleotide selected from the group consisting of SEQ ID NOs:95-98; the complement of any of SEQ ID NOs:95-98; the reverse complement of any of SEQ ID NOs:95-98; a fragment of at least 15 contiguous nucleotides of any of SEQ ID NOs:95-98; the complement of a fragment of at least 15 contiguous nucleotides of any of SEQ ID NOs:95-98; the reverse complement of a fragment of at least 15 contiguous nucleotides of any of SEQ ID NOs:95-98; a transcript of SEQ ID NO:76; the complement of a transcript of SEQ ID NO:76; the reverse complement of a transcript of SEQ ID NO:76; a fragment of at least 15 contiguous nucleotides of a transcript of SEQ ID NO:76; the complement of a fragment of at least 15 contiguous nucleotides of a transcript of SEQ ID NO:76; a transcript of SEQ ID NO:78; the complement of a transcript of SEQ ID NO:78; the reverse complement of a transcript of SEQ ID NO:78; the reverse complement of a fragment of at least 15 contiguous nucleotides of a transcript of SEQ ID NO:76; a fragment of at least 15 contiguous nucleotides of a transcript of SEQ ID NO:78; the complement of a fragment of at least 15 contiguous nucleotides of a transcript of SEQ ID NO:78; and the reverse complement of a fragment of at least 15 contiguous nucleotides of a transcript of SEQ ID NO:78.

Embodiment 52: A method for controlling a coleopteran pest population, the method comprising contacting a coleopteran pest of the population with an agent comprising a dsRNA molecule comprising a first and a second polyribonucleotide, wherein the dsRNA molecule functions upon contact with the coleopteran pest to inhibit a biological function within the coleopteran pest, wherein the first polyribonucleotide comprises a nucleotide sequence having from about 90% to about 100% sequence identity to a reference polyribonucleotide consisting of from about 15 to about 30 contiguous nucleotides of SEQ ID NO:89 or SEQ ID NO:92, and wherein the first polyribonucleotide is specifically hybridized to the second polyribonucleotide.

Embodiment 53: The method according to Embodiment 52, wherein the reference polyribonucleotide is SEQ ID NO:90, SEQ ID NO:91, SEQ ID NO:93, or SEQ ID NO:94.

Embodiment 54: A method for controlling a hemipteran pest population, the method comprising contacting a hemipteran pest of the population with an agent comprising a dsRNA molecule comprising a first and a second polyribonucleotide that functions upon contact with the coleopteran pest to inhibit a biological function within the coleopteran pest, wherein the first polyribonucleotide comprises a nucleotide sequence having from about 90% to about 100% sequence identity to a reference polyribonucleotide consisting of from about 15 to about 30 contiguous nucleotides of SEQ ID NO:95 or SEQ ID NO:97, and wherein the first polyribonucleotide is specifically hybridized to the second polyribonucleotide.

Embodiment 55: The method according to Embodiment 54, wherein the reference polyribonucleotide is SEQ ID NO:96 or SEQ ID NO:98.

Embodiment 56: The method according to any of Embodiments 49-55, wherein contacting the pest with the agent comprises contacting the pest with a sprayable formulation comprising the dsRNA molecule.

Embodiment 57: The method according to any of Embodiments 49-55, wherein contacting the pest with the agent comprises feeding the pest with the agent, and the agent is a plant cell comprising the dsRNA molecule or an RNA bait comprising the dsRNA molecule.

Embodiment 58: A method for controlling an insect pest population, the method comprising providing in a host plant of an insect pest a plant cell comprising the nucleic acid molecule of any of Embodiments 1-11, wherein the polynucleotide is expressed to produce a RNA molecule that functions upon contact with an insect pest belonging to the population to inhibit the expression of a target sequence within the insect pest and results in decreased growth and/or survival of the insect pest or pest population, relative to development of the same pest species on a plant of the same host plant species that does not comprise the polynucleotide Embodiment 59: The method according to Embodiment 58, wherein the insect pest population is reduced relative to a population of the same pest species infesting a host plant of the same host plant species lacking a plant cell comprising the nucleic acid molecule.

Embodiment 60: The method according to either of Embodiments 58 and 59, wherein the insect pest is a coleopteran pest.

Embodiment 61: The method according to either of Embodiments 58 and 59, wherein the insect pest is a hemipteran pest.

Embodiment 62: A method of controlling an insect pest infestation in a plant, the method comprising providing in the diet of the insect pest an RNA molecule comprising a polyribonucleotide that is specifically hybridizable with a reference polyribonucleotide selected from the group consisting of: SEQ ID NOs:89-98; the complement of any of SEQ ID NOs:89-98; the reverse complement of any of SEQ ID NOs:89-98; a fragment of at least 15 contiguous nucleotides of any of SEQ ID NOs:89-98; the complement of a fragment of at least 15 contiguous nucleotides of any of SEQ ID NOs:89-98; the reverse complement of a fragment of at least 15 contiguous nucleotides of any of SEQ ID NOs:89-98; a transcript of any of SEQ ID NO:1, SEQ ID NO:3, SEQ ID NO:76, and SEQ ID NO:78; the complement of a transcript of any of SEQ ID NO:1, SEQ ID NO:3, SEQ ID NO:76, and SEQ ID NO:78; the reverse complement of a transcript of any of SEQ ID NO:1, SEQ ID NO:3, SEQ ID NO:76, and SEQ ID NO:78; a fragment of at least 15 contiguous nucleotides of a transcript of any of SEQ ID NO:1, SEQ ID NO:3, SEQ ID NO:76, and SEQ ID NO:78; the complement of a fragment of at least 15 contiguous nucleotides of a transcript of any of SEQ ID NO:1, SEQ ID NO:3, SEQ ID NO:76, and SEQ ID NO:78; and the reverse complement of a fragment of at least 15 contiguous nucleotides of a transcript of any of SEQ ID NO:1, SEQ ID NO:3 , SEQ ID NO:76, and SEQ ID NO:78.

Embodiment 63: The method according to Embodiment 62, wherein the diet comprises a plant cell comprising a polynucleotide that is transcribed to express the RNA molecule.

Embodiment 64: The method according to Embodiment 62 or Embodiment 63, wherein the reference polyribonucleotide is selected from the group consisting of: SEQ ID NOs:89-94; the complement of any of SEQ ID NOs:89-94; the reverse complement of any of SEQ ID NOs:89-94; a fragment of at least 15 contiguous nucleotides of either of SEQ ID NO:89 and SEQ ID NO:92; the complement of a fragment of at least 15 contiguous nucleotides of either of SEQ ID NO:89 and SEQ ID NO:92; the reverse complement of a fragment of at least 15 contiguous nucleotides of either of SEQ ID NO:89 and SEQ ID NO:92; a transcript of SEQ ID NO:1; the complement of a transcript of SEQ ID NO:1; the reverse complement of a transcript of SEQ ID NO:1; a fragment of at least 15 contiguous nucleotides of a transcript of SEQ ID NO:1; the complement of a fragment of at least 15 contiguous nucleotides of a transcript of SEQ ID NO:1; the reverse complement of a fragment of at least 15 contiguous nucleotides of a transcript of SEQ ID NO:1; a transcript of SEQ ID NO:3; the complement of a transcript of SEQ ID NO:3; the reverse complement of a transcript of SEQ ID NO:3; a fragment of at least 15 contiguous nucleotides of a transcript of SEQ ID NO:3; the complement of a fragment of at least 15 contiguous nucleotides of a transcript of SEQ ID NO:3; and the reverse complement of a fragment of at least 15 contiguous nucleotides of a transcript of SEQ ID NO:3.

Embodiment 65: The method according to Embodiment 62 or Embodiment 63, wherein the reference polyribonucleotide is selected from the group consisting of: SEQ ID NOs:95-98; the complement of any of SEQ ID NOs:95-98; the reverse complement of any oSEQ ID NOs:95-98; a fragment of at least 15 contiguous nucleotides of any of SEQ ID NOs:95-98; the complement of a fragment of at least 15 contiguous nucleotides of any of SEQ ID NOs:95-98; the reverse complement of a fragment of at least 15 contiguous nucleotides of any of SEQ ID NOs:95-98; a transcript of SEQ ID NO:76; the complement of a transcript of SEQ ID NO:76; the reverse complement of a transcript of SEQ ID NO:76; a fragment of at least 15 contiguous nucleotides of a transcript of SEQ ID NO:76; the complement of a fragment of at least 15 contiguous nucleotides of a transcript of SEQ ID NO:76; the reverse complement of a fragment of at least 15 contiguous nucleotides of a transcript of SEQ ID NO:76; a transcript of SEQ ID NO:78; the complement of a transcript of SEQ ID NO:78; the reverse complement of a transcript of SEQ ID NO:78; a fragment of at least 15 contiguous nucleotides of a transcript of SEQ ID NO:78; the complement of a fragment of at least 15 contiguous nucleotides of a transcript of SEQ ID NO:78; and the reverse complement of a fragment of at least 15 contiguous nucleotides of a transcript of SEQ ID NO:78.

Embodiment 66: A method for improving the yield of a crop, the method comprising cultivating in the crop a plant comprising the nucleic acid molecule of any of Embodiments 1-11 to allow the expression of the polynucleotide.

Embodiment 67: The method according to Embodiment 66, wherein expression of the polynucleotide produces a dsRNA molecule that suppresses at least a first target gene in an insect pest that has contacted a portion of the plant, thereby inhibiting the development or growth of the insect pest and loss of yield due to infection by the insect pest.

Embodiment 68: A method for producing a transgenic plant cell, the method comprising transforming a plant cell with the vector of Embodiment 10 or Embodiment 11; culturing the transformed plant cell under conditions sufficient to allow for development of a plant cell culture comprising a plurality of transgenic plant cells; selecting for transgenic plant cells that have integrated the polynucleotide into their genomes; screening the transgenic plant cells for expression of a dsRNA molecule encoded by the polynucleotide; and selecting a transgenic plant cell that expresses the dsRNA.

Embodiment 69: The method according to any of Embodiments 66-68, wherein the plant or plant cell is *Zea mays*, *Glycine max*, or a *Gossypium* sp.

Embodiment 70: The method according to Embodiment 69, wherein the plant or plant cell is *Zea mays*.

Embodiment 71: The method according to Embodiment 69, wherein the plant or plant cell is *Glycine max*.

Embodiment 72: The method according to Embodiment 69, wherein the plant or plant cell is a *Gossypium* sp.

Embodiment 73: A method for producing an insect pest-resistant transgenic plant, the method comprising regenerating a transgenic plant from a transgenic plant cell comprising the nucleic acid molecule of any of Embodiments 1-11, wherein expression of a dsRNA molecule encoded by the polynucleotide is sufficient to modulate the expression of a target gene in the insect pest when it contacts the RNA molecule.

Embodiment 74: The nucleic acid molecule of any of Embodiments 1-11, further comprising a polynucleotide encoding an insecticidal polypeptide from *Bacillus thuringiensis*.

Embodiment 75: The plant cell of any of Embodiments 26 and 33-37, further comprising a polynucleotide encoding an insecticidal polypeptide from *Bacillus thuringiensis, Alcaligenes* spp., or *Pseudomonas spp*.

Embodiment 76: The plant of any of Embodiments 29, 32, and 37-45, further comprising a polynucleotide encoding an insecticidal polypeptide from *Bacillus thuringiensis, Alcaligenes* spp., or *Pseudomonas* spp.

Embodiment 77: The method according to any of Embodiments 57-61 and 63-73, wherein the plant or plant cell comprises a polynucleotide encoding an insecticidal polypeptide from *Bacillus thuringiensis, Alcaligenes* spp., or *Pseudomonas* spp.

Embodiment 78: The nucleic acid molecule of Embodiment 74, the plant cell of Embodiment 75, the plant of Embodiment 76, or the method according to Embodiment 77, wherein the insecticidal polypeptide is selected from the group of B. thuringiensis insecticidal polypeptides consisting of Cry1B, Cry1I, Cry3, Cry7A, Cry8, Cry9D, Cry4, Cry18, Cry22, Cry23, Cry34, Cry35, Cry36, Cry37, Cry43, Cry55, Cyt1A, and Cyt2C.

Embodiment 79: The method according to any of Embodiments 49, 50, 56-59, 62-64, 67, 69-72, and 78 wherein the insect pest is a coleopteran pest.

Embodiment 80: The method according to any of Embodiments 52, 53, and 60, wherein the coleopteran pest is any pest selected from the group consisting of *D. v. virgifera* LeConte (western corn rootworm, "WCR"); *D. barberi* Smith and Lawrence (northern corn rootworm, "NCR"); *D. u. how ardi* Barber (southern corn rootworm, "SCR"); *D. v. zeae* Krysan and Smith (Mexican corn rootworm, "MCR"); *D. balteata* LeConte; *D. u. tenella*; *D. u. undecimpunctata* Mannerheim; and *D. speciosa* Germar.

Embodiment 81: The method according to any of Embodiments 49, 51, 56-59, 62, 63, 65, 67, 69-73, and 78, wherein the insect pest is a hemipteran pest.

Embodiment 82: The method according to any of Embodiments 54, 55, 61, and 81, wherein the hemipteran pest is any pest selected from the group consisting of *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

---

The invention claimed is:

1. An isolated nucleic acid molecule comprising a polynucleotide operably linked to a heterologous promoter, wherein the polynucleotide encodes a hairpin ribonucleic acid (hpRNA) molecule with a stem-and-loop structure that inhibits an endogenous gene in a *Diabrotica virgifera* insect when the hpRNA molecule is ingested by the insect, the polynucleotide comprising:
   a first nucleotide sequence comprising at least 410 contiguous nucleotides of SEQ ID NO:1, the complement or reverse complement of at least 410 contiguous nucleotides of SEQ ID NO:1, at least 320 contiguous nucleotides of SEQ ID NO:3, or the complement or reverse complement of at least 320 contiguous nucleotides of SEQ ID NO:3;
  - a second nucleotide sequence; and
  - a third nucleotide sequence that is reverse complement of the first nucleotide sequence,
  - wherein ribonucleotide sequences in the dsRNA molecule encoded by the first and the third nucleotide sequences are comprised in the stem structure of the hpRNA molecule when the polynucleotide is transcribed.

2. The nucleic acid molecule of claim 1, wherein the first nucleotide sequence comprises a sequence selected from the group consisting of SEQ ID NO:7, the complement and reverse complement of SEQ ID NO:7, SEQ ID NO:8, and the complements and reverse complement of SEQ ID NO:8.

3. The nucleic acid molecule of claim 1, wherein the molecule is a vector.

4. The nucleic acid molecule of claim 3, wherein the heterologous promoter is functional in a plant cell.

5. The hpRNA molecule encoded by the polynucleotide of the nucleic acid molecule of claim 1, the hpRNA comprising:
  - a first ribonucleotide sequence encoded by the first nucleotide sequence;
  - a second ribonucleotide sequence encoded by the second nucleotide sequence; and
  - a third ribonucleotide sequence encoded by the third nucleotide sequence, wherein the third ribonucleotide sequence is the reverse complement of the first ribonucleotide sequence,
  - wherein the second ribonucleotide sequence is positioned between the first and third ribonucleotide sequences in the hpRNA molecule, and
  - wherein the first and third ribonucleotides are comprised in a stem structure in the hpRNA molecule.

6. The nucleic acid molecule of claim 1, wherein the heterologous promoter is functional in a plant cell.

7. A cell comprising the nucleic acid molecule of claim 1.

8. The cell of claim 7, wherein the cell is a prokaryotic cell.

9. The cell of claim 7, wherein the cell is a eukaryotic cell.

10. A transgenic plant cell comprising the nucleic acid molecule of claim 6.

11. A transgenic plant material comprising the nucleic acid molecule of claim 6.

12. The transgenic plant material of claim 11, wherein the heterologous promoter is functional in a cell of the plant material.

13. The transgenic plant material of claim 12, wherein the plant material is a plant or seed.

14. A commodity product that comprises a detectable amount of the hpRNA molecule of claim 5.

15. The transgenic plant cell of claim 10, wherein the cell is a *Zea mays* or *Glycine max* cell.

16. The transgenic plant material of claim 12, wherein the plant material is a *Zea mays* or *Glycine max* plant material.

17. A method for controlling a *Diabrotica virgifera* insect pest population, the method comprising feeding insects of the population with an agent comprising the hpRNA molecule of claim 5.

18. The method according to claim 17, wherein the agent is a transgenic plant material expressing the hpRNA molecule.

19. The method according to claim 17, wherein the agent is a sprayable composition or RNA bait.

20. A method for improving the yield of a crop, the method comprising:
  - cultivating in the crop the transgenic plant or seed of claim 13, such that the hpRNA molecule is expressed.

21. The method according to claim 20, wherein the transgenic plant or seed is *Zea mays* or *Glycine max*.

22. A method for producing a transgenic plant cell, the method comprising:
  - transforming a plant cell with the nucleic acid molecule of claim 6;
  - culturing the transformed plant cell under conditions sufficient to allow for development of a plant cell culture comprising a plurality of transgenic plant cells; and
  - selecting a transgenic plant cell that has integrated the polynucleotide in its genome and expresses the hpRNA molecule.

23. A method for producing a transgenic plant resistant to *Diabrotica virgifera* infection, the method comprising:
  - regenerating a transgenic plant from the transgenic plant cell of claim 10.

24. The nucleic acid of claim 1, further comprising a polynucleotide encoding an insecticidal polypeptide from *Bacillus thuringiensis, Alcaligenes* spp., or *Pseudomonas* spp.

25. The nucleic acid of claim 24, wherein the insecticidal polypeptide is selected from the group consisting of Cry1B, Cry 1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

26. The transgenic plant cell of claim 10, wherein the cell comprises a polynucleotide encoding an insecticidal polypeptide from *Bacillus thuringiensis, Alcaligenes* spp., or *Pseudomonas* spp.

27. The transgenic plant cell of claim 26, wherein the insecticidal polypeptide is selected from the group consisting of Cry1B, Cry1I, Cry3, Cry7A, Cry8, Cry9D, Cry14, Cry18, Cry22, Cry23, Cry34, Cry35, Cry36, Cry37, Cry43, Cry55, Cyt1A, and Cyt2C.

28. The transgenic plant material of claim 11, wherein the plant material comprises a polynucleotide encoding an insecticidal polypeptide from *Bacillus thuringiensis, Alcaligenes* spp., or *Pseudomonas* spp.

29. The transgenic plant material of claim 28, wherein the insecticidal polypeptide is selected from the group consisting of Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

30. The method according to claim 17, further comprising feeding the insects with an insecticidal polypeptide from *Bacillus thuringiensis, Alcaligenes* spp., or *Pseudomonas* spp.

31. The method according to claim 30, wherein the insecticidal polypeptide is selected from the group consisting of Cry1B, Cry 1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

32. The transgenic plant or seed of claim 13, wherein the plant or seed is *Zea mays* or *Glycine max*.

33. An isolated nucleic acid molecule comprising a polynucleotide operably linked to a heterologous promoter, wherein the polynucleotide encodes a hairpin ribonucleic acid (hpRNA) molecule with a stem-and-loop structure that inhibits an endogenous gene in a *Diabrotica virgifera* insect when the hpRNA molecule is ingested by the insect, the polynucleotide comprising:
   a first nucleotide sequence comprising SEQ ID NO:5, the complement or reverse complement of SEQ ID NO:5, SEQ ID NO:6, or the complement or reverse complement of SEQ ID NO:6;
   a second nucleotide sequence; and
   a third nucleotide sequence that is reverse complement of the first nucleotide sequence,
   wherein ribonucleotide sequences in the hpRNA molecule encoded by the first and the third nucleotide sequences are comprised in the stem structure of the hpRNA molecule when the polynucleotide is transcribed.

* * * * *